United States Patent
Chen

(10) Patent No.: US 8,318,808 B2
(45) Date of Patent: *Nov. 27, 2012

(54) $ZN^{2+}$ CHELATING MOTIF-TETHERED SHORT-CHAIN FATTY ACIDS AS A NOVEL CLASS OF HISTONE DEACETYLASE INHIBITORS

(75) Inventor: Ching-Shih Chen, Upper Arlington, OH (US)

(73) Assignee: The Ohio State University Research Foundation, Columbus, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/361,626

(22) Filed: Jan. 29, 2009

(65) Prior Publication Data

US 2009/0137679 A1    May 28, 2009

Related U.S. Application Data

(63) Continuation of application No. 10/597,022, filed on Jun. 18, 2007.

(51) Int. Cl.
*A61K 31/19* (2006.01)
*C07C 223/00* (2006.01)

(52) U.S. Cl. ........... 514/575; 564/123
(58) Field of Classification Search ............. 514/575; 564/123
See application file for complete search history.

(56) References Cited

U.S. PATENT DOCUMENTS

| | | |
|---|---|---|
| 5,145,684 A | 9/1992 | Liversidge et al. |
| 5,536,727 A | 7/1996 | Witzel et al. |
| 5,610,162 A | 3/1997 | Witzel et al. |
| 5,776,888 A | 7/1998 | Leone-Bay |
| 5,783,593 A | 7/1998 | Baker et al. |
| 5,972,978 A | 10/1999 | Andersen et al. |
| 6,034,096 A * | 3/2000 | Bertolini et al. ............... 514/307 |
| 6,045,829 A | 4/2000 | Liversidge et al. |
| 6,174,905 B1 | 1/2001 | Suzuki et al. |
| 6,429,213 B1 | 8/2002 | Xue et al. |
| 6,743,807 B2 | 6/2004 | Duan et al. |
| 6,858,626 B2 | 2/2005 | Xue et al. |
| 6,984,648 B2 | 1/2006 | Lu et al. |
| 7,183,268 B2 | 2/2007 | Zemlicka et al. |
| 7,235,689 B2 | 6/2007 | Pinori et al. |
| 7,410,988 B2 | 8/2008 | Dickson, Jr. et al. |
| 2003/0091623 A1 | 5/2003 | Cumming et al. |
| 2003/0225054 A1 | 12/2003 | Duan |
| 2004/0092598 A1 | 5/2004 | Watkins et al. |
| 2007/0225373 A1 | 9/2007 | Chen |

FOREIGN PATENT DOCUMENTS

| | | |
|---|---|---|
| EP | 242851 | 10/1987 |
| EP | 974576 | 1/2001 |
| JP | 10152462 | 6/1998 |
| JP | 11302173 | 11/1999 |

(Continued)

OTHER PUBLICATIONS

International Search Report and Written Opinion for PCT/US04/40211, mailed Jul. 25, 2008.

(Continued)

*Primary Examiner* — Taylor Victor Oh
(74) *Attorney, Agent, or Firm* — Calfee, Halter & Griswold LLP

(57) ABSTRACT

$Zn^{2+}$-chelating motif-tethered fatty acids as histone deacetylase (HDAC) inhibitors. Compounds performed well in in vitro and in vivo tests.

38 Claims, 32 Drawing Sheets

FOREIGN PATENT DOCUMENTS

| | | |
|---|---|---|
| JP | 2003-137866 | 5/2003 |
| JP | 2003-226680 | 8/2003 |
| WO | 01/16106 | 3/2001 |
| WO | 01/34131 | 5/2001 |
| WO | WO 01/38322 | 5/2001 |
| WO | WO 01/70675 | 9/2001 |
| WO | 02/22577 | 3/2002 |
| WO | 02/26696 | 4/2002 |
| WO | WO02/26696 * | 4/2002 |
| WO | 02/074298 | 9/2002 |
| WO | 03/013493 | 2/2003 |
| WO | WO 03/070691 | 8/2003 |
| WO | 2004/052838 | 6/2004 |
| WO | 2005/055928 | 6/2005 |

OTHER PUBLICATIONS

Phiel et al. "Histone deacetylase is a direct target of valproic acid, a potent anticonvulsant, mood stabilizer, and teratogen," J. Biol. Chem., 276, p. 36734-36741 (2001).
Saito et al., "A synthetic inhibitor of histone deacetylase, MS-27-275, with marked in vivo antitumor activity against human tumors," Proc Natl Acad Sci U S A, 96, p. 4592-4597 (1999).
Komatsu et al., "Cyclic Hydroxamic-acid-containing Peptide 31, a Potent Synthetic Histone Deacetylase Inhibitor with Antitumor Activity", Cancer Research, 61, p. 4459-4466 (2001).
Massa et al, "3-(4-Aroyl-1H-pyrrol-2-yl)-N-hydroxy-2-propenamides, a New class of synthetic histone deacetylase Inhibitors", J Med Chem 44, p. 2069-2072 (2001).
Suzuki et al., "Synthesis and histone deacetylase inhibitory activity of new benzamide derivatives", J Med Chem, 42, p. 3001-3003 (1999).
Taunton et al., "A Mammalian Histone Deacetylase Related to the Yeast Transcriptional Regulator Rpd3p," Science, 272, p. 408-411 (1996).
Yoshida et al., "Potent and Specific Inhibitors of Mammalian Histone Deacetylases Both in Vivo and in Vitro by Trichostatin A," J. Biol. Chem., 265, p. 17174-17179 (1990).
Marks et al., "Histone deacetylase inhibitors: inducers of differentiation or apoptosis of transformed cells," J. Natl. Cancer Inst., 92, p. 1210-1216 (2000).
Jung, M. "Inhibitors of histone deacetylase as new anticancer agents," Curr. Med. Chem., 8, p. 1505-1511 (2001).
Han et al., "Apicidin, a histone deacetylase inhibitor, inhibits proliferation of tumor cells via induction of p21WAF1/Cip1 and gelsolin" Cancer Res., 60, p. 6068-6074 (2000).
Jung et al. "Amide analogues of trichostatin A as inhibitors of histone deacetylase and inducers of terminal cell differentiation," J. Med. Chem., 42, p. 4669-4679 (1999).
Finnin et al., "Structures of a histone deacetylase homologue bound to the TSA and SAHA inhibitors," Nature, 401, p. 188-193 (1999).
Furumai et al., "Potent histone deacetylase inhibitors built from trichostatin A and cyclic tetrapeptide antibiotics including trapoxin," Proc Natl Acad Sci U S A, 98, p. 87-92 (2001).
Lea et al., "Discordant effects of butyrate analogues on erythroleukemia cell proliferation, differentiation and histone deacetylase," Anticancer Res., 15, p. 879-883 (1995).
Kijima et al., "Trapoxin, an antitumor cyclic tetrapeptide, is an irreversible inhibitor of mammalian histone deacetylase," J. Biol. Chem., 268, p. 22429-22435 (1993).
Richon et al. "A class of hybrid polar inducers of transformed cell differentiation inhibits histone deacetylases," Proc. Natl. Acad. Sci. U S A, 95, p. 3003-3007 (1998).
Remiszewski et al., "Inhibitors of human histone deacetylase: synthesis and enzyme and cellular activity of straight chain hydroxamates," J. Med. Chem., 45, p. 753-757 (2000).
Nakajima et al., "FR901228, a potent antitumor antibiotic, is a novel histone deacetylase inhibitor," Exp Cell Res., 241, p. 126-133 (1998).
Shute et al., "Analogues of the cytostatic and antimitogenic agents chlamydocin and HC-toxin: synthesis and biological activity of chloromethyl ketone and diazomethyl ketone functionalized cyclic tetrapeptides," J. Med. Chem., 30, p. 71-78 (1987).
Sternson et al., "Synthesis of 7200 small molecules based on a substructural analysis of the histone deacetylase inhibitors trichostatin and trapoxin," Org. Lett. 3, p. 4239-4242 (2001).
Vanommeslaeghe et al., "Ab initio study of the binding of Trichostatin A (TSA) in the active site of histone deacetylase like protein (HDLP)," Org. Biomol. Chem. 1, p. 2951-2957 (2003).
Fuino et al., "Histone deacetylasse inhibitor LAQ824 down-regulates Her-2 and sensitizes human breast cancer cells to trastuzumab, taxotere, gemcitabine, and epothilone B," Mol. Cancer Ther., 2, p. 971-984 (2003).
Lu et al., "Zn2+-chelating motif-tethered short-chain fatty acids as a novel class of histone deacetylase inhibitors," J. Med. Chem., 47(2), p. 467-74 ( 2004).
Grozinger et al., "Deacetylase enzymes: biological functions and the use of small-molecule inhibitors," Chem. Biol., 9, p. 3-16 (2002).
Johnstone, R. W., "Histone-deacetylase inhibitors: novel drugs for the treatment of cancer," Nat. Rev. Drug Discov., 1, p. 287-299 (2002).
Kramer et al., "Histone deacetylase as a therapeutic target," Trends Endocrinol. Metab., 12, p. 294-300 (2001).
Office action from U.S. Appl. No. 10/597,022 dated Sep. 24, 2009.
Amendment from U.S. Appl. No. 10/597,022 dated Jan. 25, 2010.
Supplemental Amendment from U.S. Appl. No. 10/597,022 dated Feb. 24, 2010.
Office action from U.S. Appl. No. 10/597,022 dated Apr. 29, 2010.
European Search report dated Jun. 1, 2010 from EP Application No. 04812666.
Han et al., "Apicidin, a histone deacetylase inhibitor, inhibits proliferation of tumor cells via induction of p21WAF1/Cip1 and gelsolin", Cancer Res, 60, 6068-6074, 2000.
Jung et al., "Amide analogues of trichostatin A as inhibitors of histone deacetylase and inducers of terminal cell differentiation", J Med Chem 42, 4669-4679, 1999.
Kim et al., "Inhibition of histone deacetylase increases cytotoxicity to anticancer drugs targeting DNA", Cancer Res 63, 7291-7300, 2003.
Kim et al., "Synthesis and Biological Evolution of 3-(4-Substituted-phenyl)-N-hydroxy-2-propenamides, a new class of histone deacetylase inhibitors", J of Medicinal Chemistry, American Chemical Society, vol. 46, No. 26, Jan. 1, 2003, pp. 5745-5751.
Kraker et al., "Modulation of histone acetylation by [4-(acetylamino)-N-(2-amino-phenyl) benamide] in HCT-8 colon carcinoma", Mol Cancer Ther, 2, 401-408, 2003.
Lu et al., "Efficacy of a Novel Histone Deacetylase Inhibitor in Murine Models of Hepatocellular Carcinoma", Hepatology, pp. 1119-1130, Oct. 2007.
Lucas et al., "The histone deacetylase inhibitor MS-275 induces caspase-dependent apoptosis in B-cell chronic lymphocytic leukemia cells", Leukemia, 18, 1207-1214, 2004.
Maeda et al., "Potent histone deacetylase inhibitors: N-hydroxybenzamides with antitumor activities", Bioorganic & Medicinal Chemistry, vol. 12, No. 16, pp. 4351-4360, Jul. 1, 2004.
Marks et al. "Histone deacetylase inhibitors: inducers of differentiation or apoptosis of transformed cells", J Natl Cancer Inst, 92: 1210-1216, 2000.
Miller, et al., "Histone deacetylase inhibitors", J Med Chem 46, 5097-5116, 2003.
Piekarz, et al., "T-cell lymphoma as a model for the use of histone deacetylase inhibitors in cancer therapy: impact of depsipeptide on molecular markers, therapeutic targets, and mechanisms of resistance", Blood, 103, 4636-4643, 2004.
Yang et al., "A Rationally Designed Histone Deacetylase Inhibitor with Distinct Antitumor Activity against Ovarian Cancer", Neoplasia, vol. 11, No. 6, Jun. 2009, pp. 552-563.
Lucas et al., "The novel deacetylase inhibitor AR-42 Demonstrates Pre-Clinical Activity in B-Cell Malignancies In Vitro and In Vivo", PLOS ONE, vol. 5, issue 6, pp. 1-10, Jun. 2010.
Office action from Japanese Application No. 2006-542704 dated Jan. 17, 2011.
Communication from European Application No. 04812666.8 dated Dec. 9, 2011.

* cited by examiner

| | R | Compounds | IC$_{50}$ (µM) |
|---|---|---|---|
| (R-C(O)-NH-CH$_2$-C$_6$H$_4$-C(O)-NH-C$_6$H$_4$-NH$_2$) | CH$_3$CH$_2$CH$_2$- | 11 | 6.0 ± 0.5 |
| | Ph-CH$_2$- | 12 | 5.2 ± 0.4 |
| | Ph-CH$_2$CH$_2$CH$_2$- | 13 | 4.3 ± 0.3 |
| (R-C(O)-NH-CH$_2$-C$_6$H$_4$-C(O)-NHOH) | CH$_3$CH$_2$CH$_2$- | 14 | 3.6 ± 0.5 |
| | Ph-CH$_2$- | 15 | 2.5 ± 0.3 |
| | Ph-CH$_2$CH$_2$CH$_2$- | 16 | 1.2 ± 0.1 |
| (R-C(O)-NH-C$_6$H$_4$-C(O)-NHOH) | CH$_3$CH$_2$CH$_2$- | 17 | 1.5 ± 0.2 |
| | Ph-CH$_2$- | 18 | 0.11 ± 0.01 |
| | Ph-CH$_2$CH$_2$CH$_2$- | 19 (HTPB) | 0.044 ± 0.006 |
| (R-C(O)-NH-C$_6$H$_4$-CH$_2$CH$_2$-C(O)-NHOH) | CH$_3$CH$_2$CH$_2$- | 20 | 1.6 ± 0.2 |
| | Ph-CH$_2$- | 21 | 0.67 ± 0.08 |
| | Ph-CH$_2$CH$_2$CH$_2$- | 22 | 0.53 ± 0.06 |

FIGURE 3

Scheme 1[a]
A
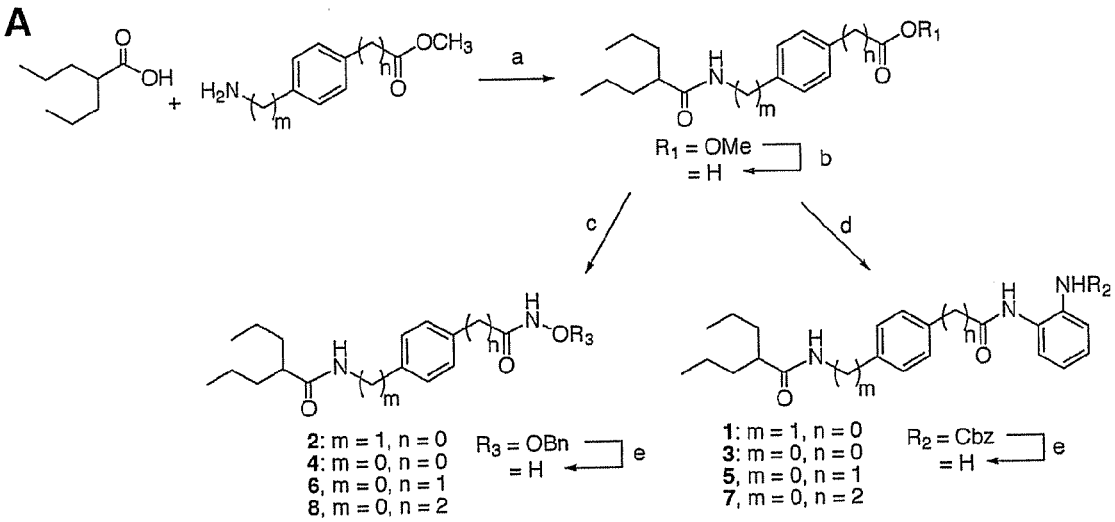
B
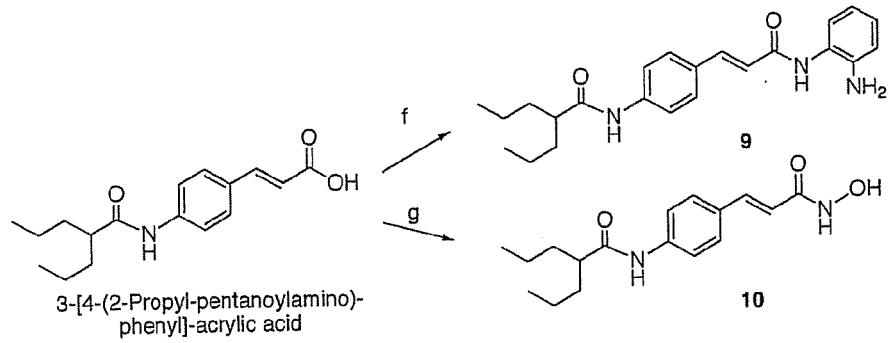
[a]Reagents: (a) EDC, THF; (b) KOH/MeOH, 80 °C; (c) NH₂OBn·HCl, BOPCl, Et₃N; (d) (2-aminopheny)carbamic acid benzyl ester, EDC, THF; (e) 10% Pd/C, H₂, MeOH/THF; (f) NH₂OH·HCl, EDC, HOBT, Et₃N; (g) o-phenylene diamine, EDC, THF.
FIGURE 6

| Compound | Structure | HDAC IC50 (uM) | Cell Viability(DU145, 10%FBS,3d)(uM) | Nomenclature |
|---|---|---|---|---|
| 1 | 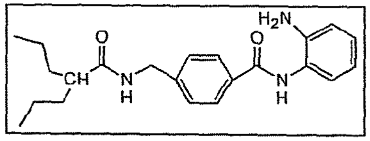 | 8 | | N-(2-Amino-phenyl)-4-{[(2-propyl-pentanoyl)amino)-methyl]-benzamide |
| 2 | 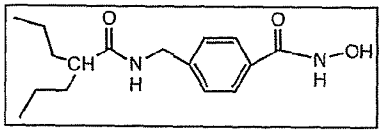 | 5 | | N-Hydroxy-4-{[(2-propyl-pentanoyl)amino)-methyl]-benzamide |
| 3 | 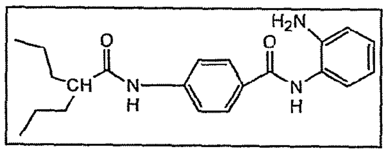 | 20 | | N-(2-Amino-phenyl)-4-(2-propyl-pentanoylamino)-benzamide |
| 4 | 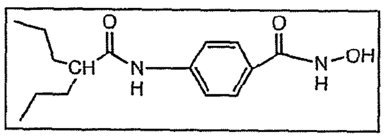 | 4 | | N-Hydroxy-4-(2-propyl-pentanoylamino)-benzamide |
| 5 | 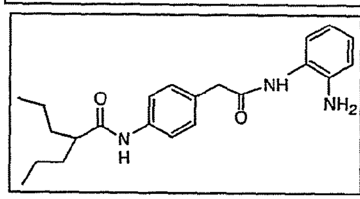 | 80 | | 2-Propyl-pentanoic acid {4-[2'-amino-phenylcarbamoyl)-methyl]-phenyl}-amide |

FIGURE 7 (Frame 1)

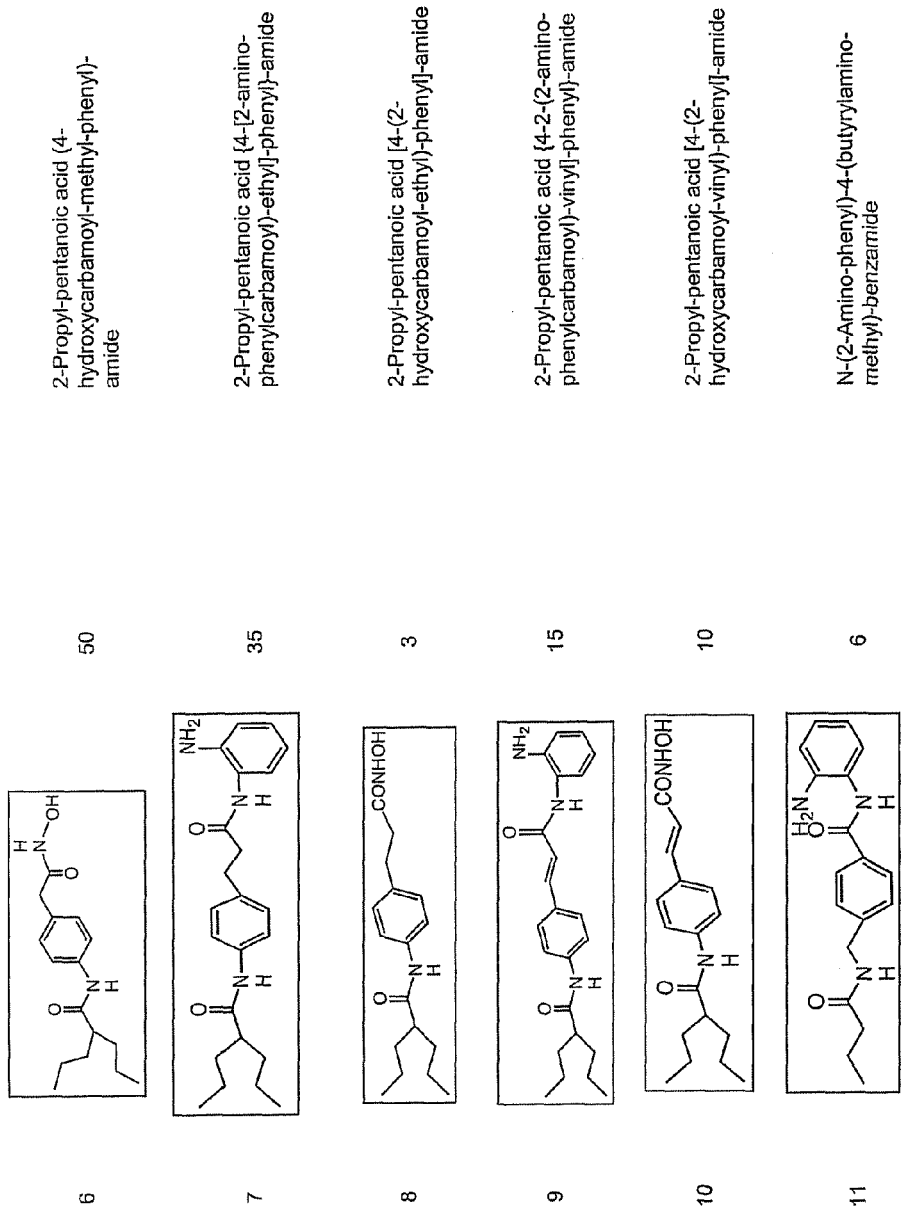
FIGURE 7 (Frame 2)

| # | Structure | Value | Name |
|---|---|---|---|
| 12 | | 5.2 | N-(2-Amino-phenyl)-4-(phenylacetylamino-methyl)-benzamide |
| 13 | | 4.3 | N-(2-Amino-phenyl)-4-[(4-phenyl-butyrylamino-methyl]-benzamide |
| 14 | | 3.6 | 4-(Butyrylamino-methyl)-N-hydroxy-benzamide |
| 15 | | 2.5 | N-hydroxy-4-(phenylacetylamino-methyl)-benzamide |
| 16 | | 1.2 | N-hydroxy-4-[(4-phenyl-butyrylamino)-methyl]-benzamide |
| 17 | | 1.5 | 4-Butyrylamino-N-hydroxy-benzamide |
| 18 | | 0.11 | N-hydroxy-4-phenylacetylamino-benzamide |

FIGURE 7 (Frame 3)

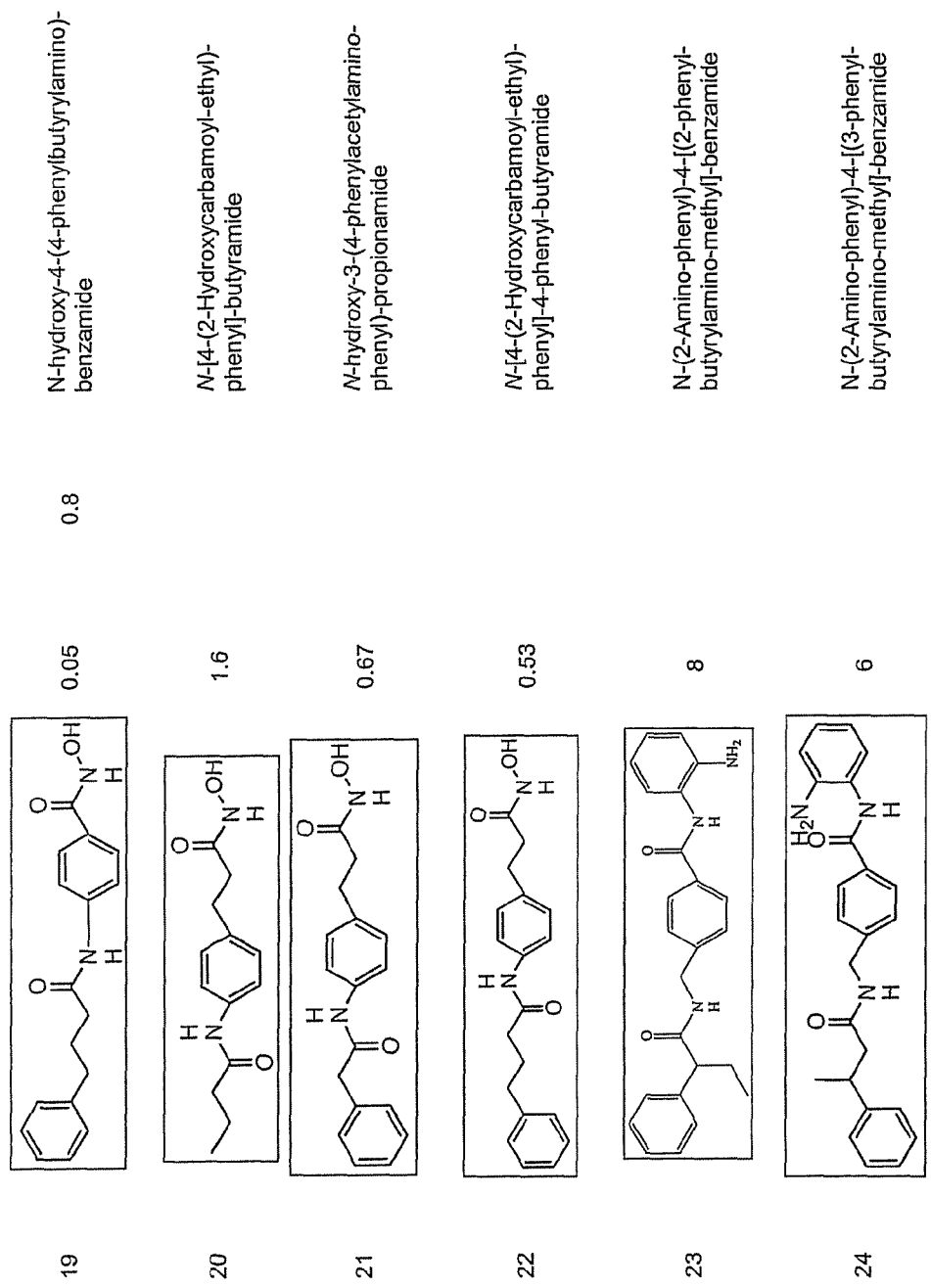
FIGURE 7 (Frame 4)

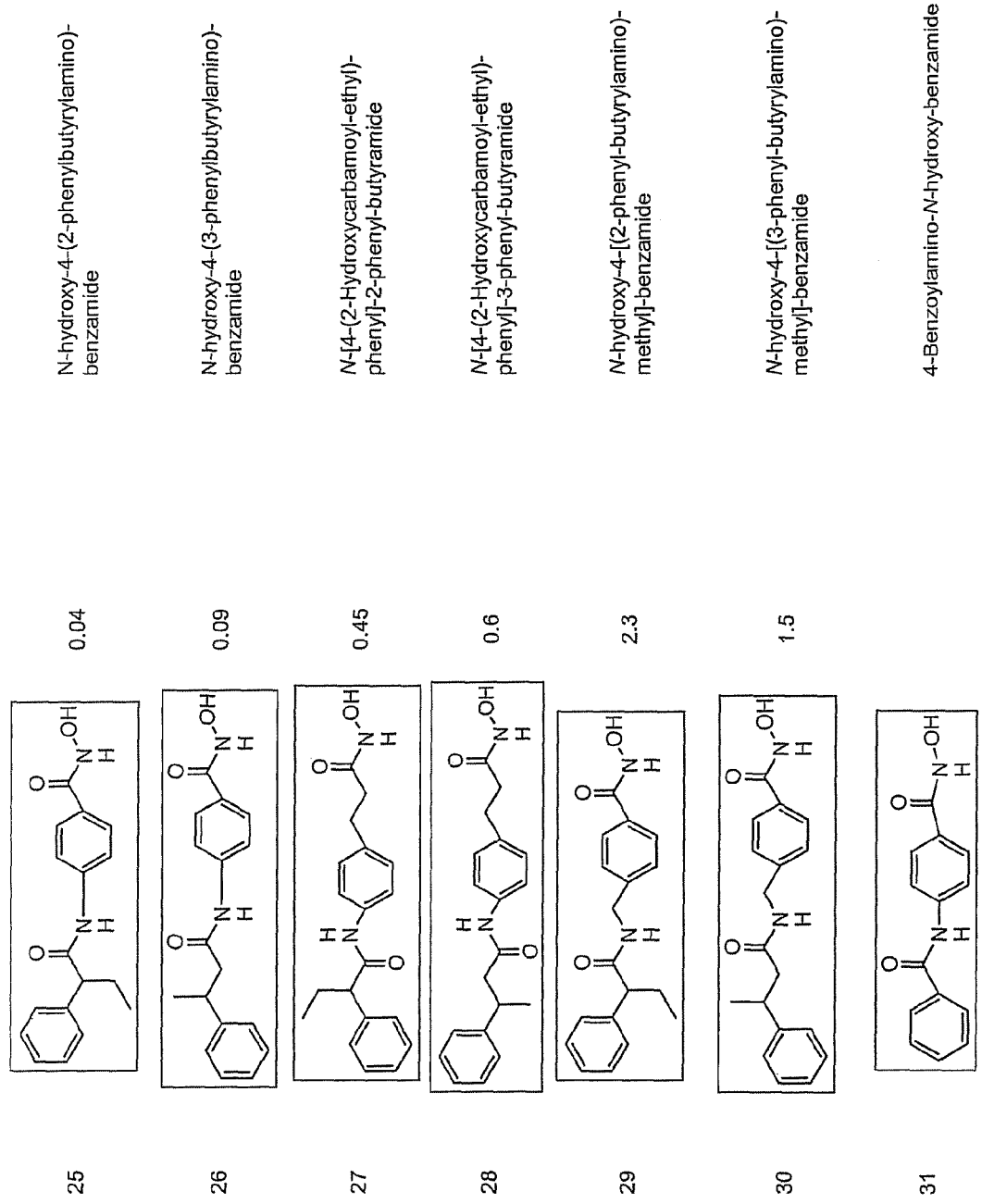
FIGURE 7 (Frame 5)

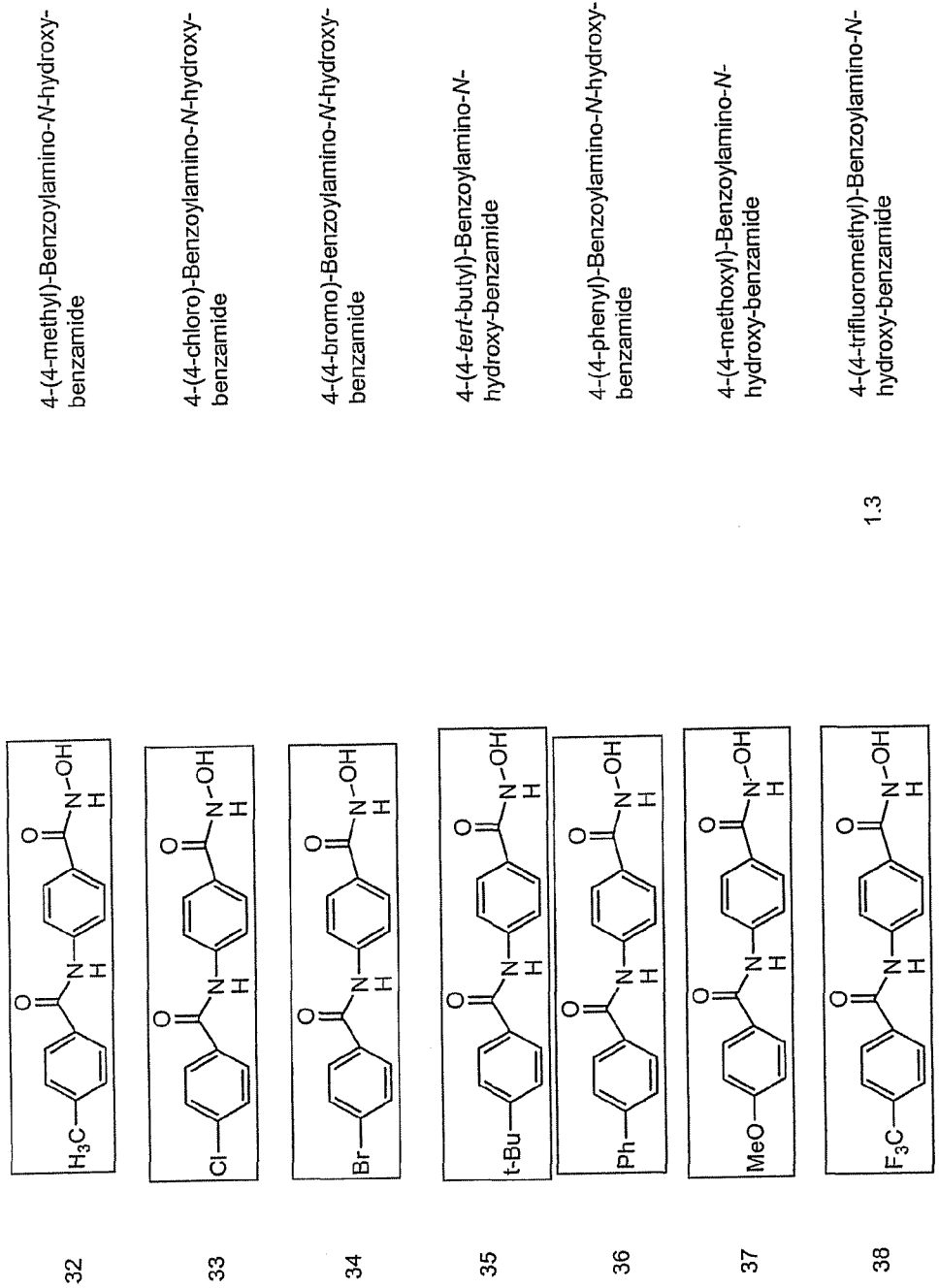
FIGURE 7 (Frame 6)

| # | Structure | IC50 (µM) | IC50 (µM) | Name |
|---|---|---|---|---|
| 39 | 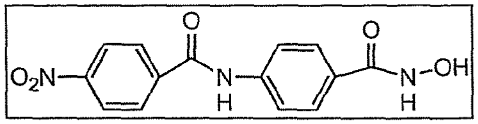 | 0.1 | | 4-(4-nitro)-Benzoylamino-N-hydroxy-benzamide |
| 40 | 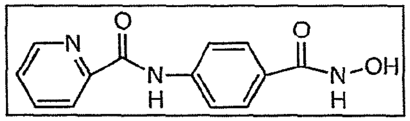 | | | Pyridine-2-carboxylic acid (4-hydroxycarbamoyl-phenyl)-amide |
| 41 | 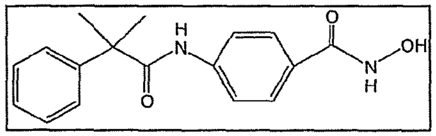 | 0.06 | 1.5 | N-hydroxy-4-(2-methyl-2-phenyl-propionylamino)-benzamide |
| 42 | 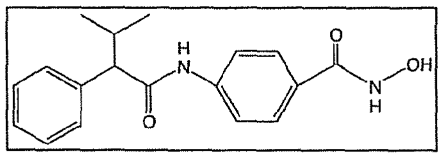 | | 0.4 | N-hydroxy-4-(3-methyl-2-phenyl-butyrylamino)-benzamide |
| 43 | 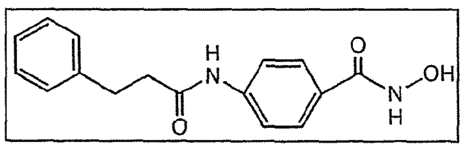 | 0.025 | 1.5 | N-hydroxy-4-(3-phenyl-propionylamino)-benzamide |
| 44 | 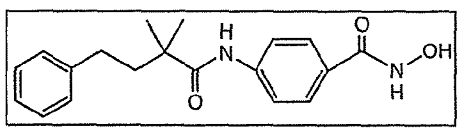 | | 0.4 | 4-(2,2-Dimethyl-4-phenyl-butyrylamino)-N-hydroxy-benzamide |
| 45 | 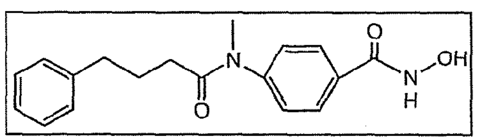 | 0.5 | | N-hydroxy-4-[methyl-(4-phenyl-butyryl)-amino]-benzamide |

FIGURE 7 (Frame 7)

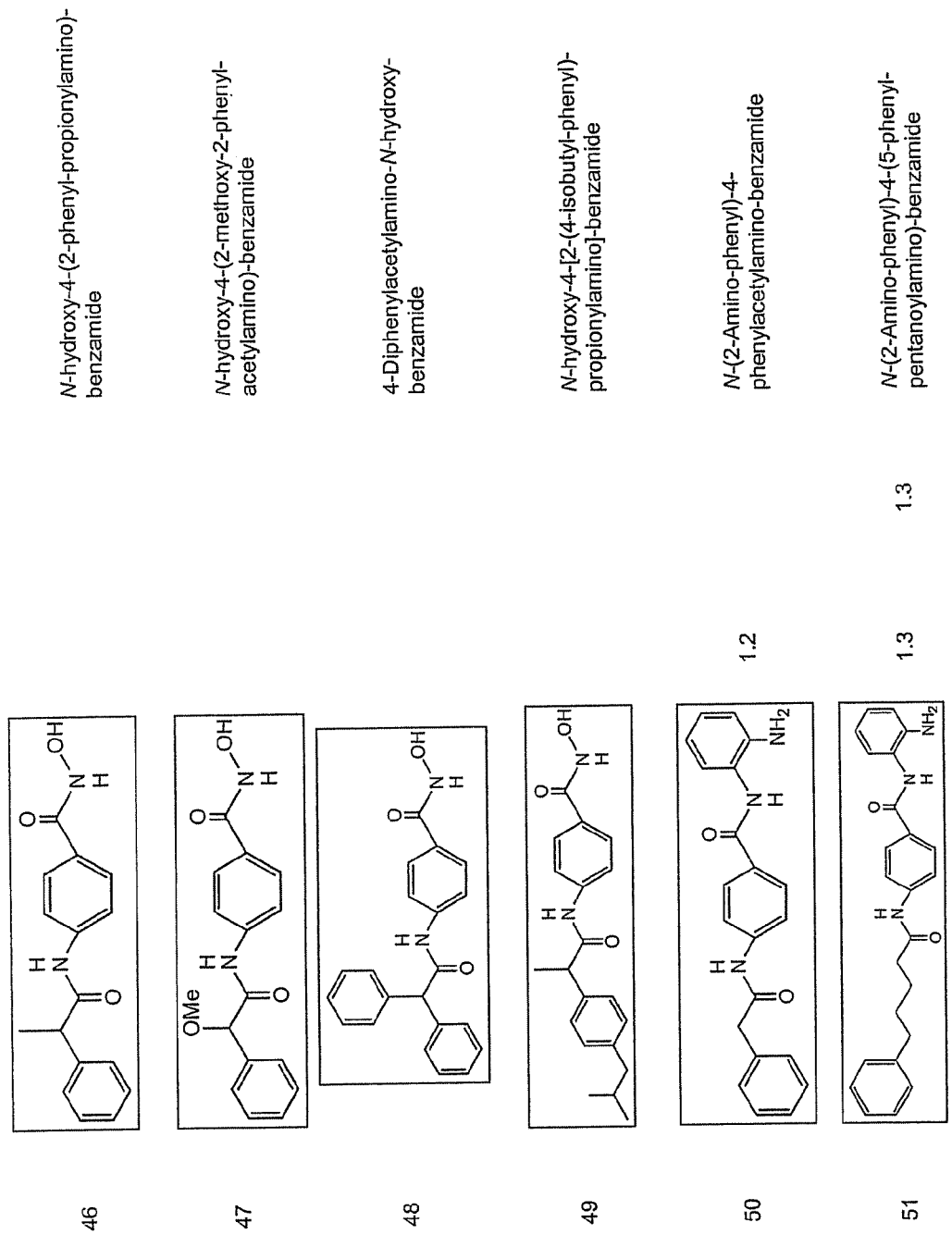
FIGURE 7 (Frame 8)

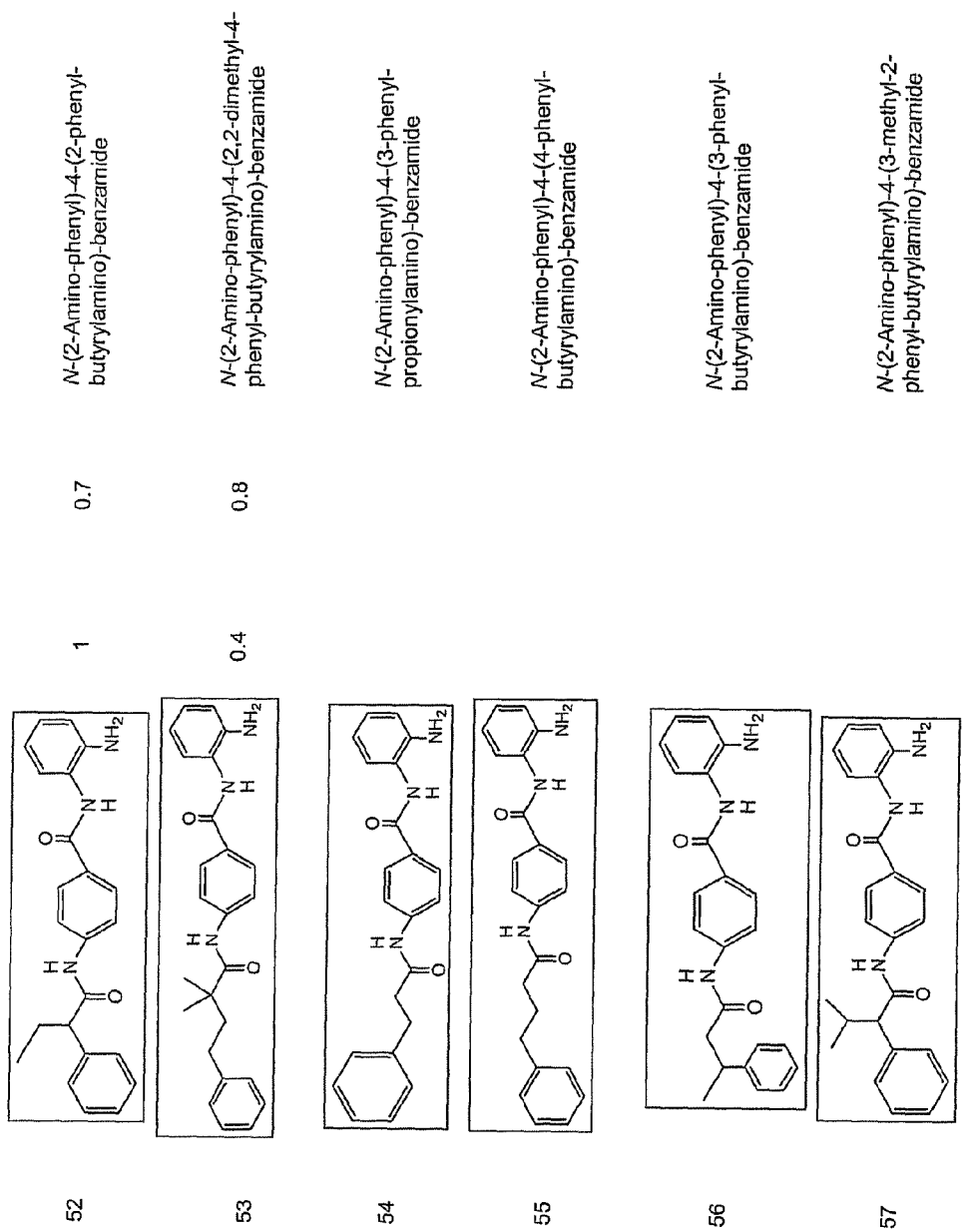
FIGURE 7 (Frame 9)

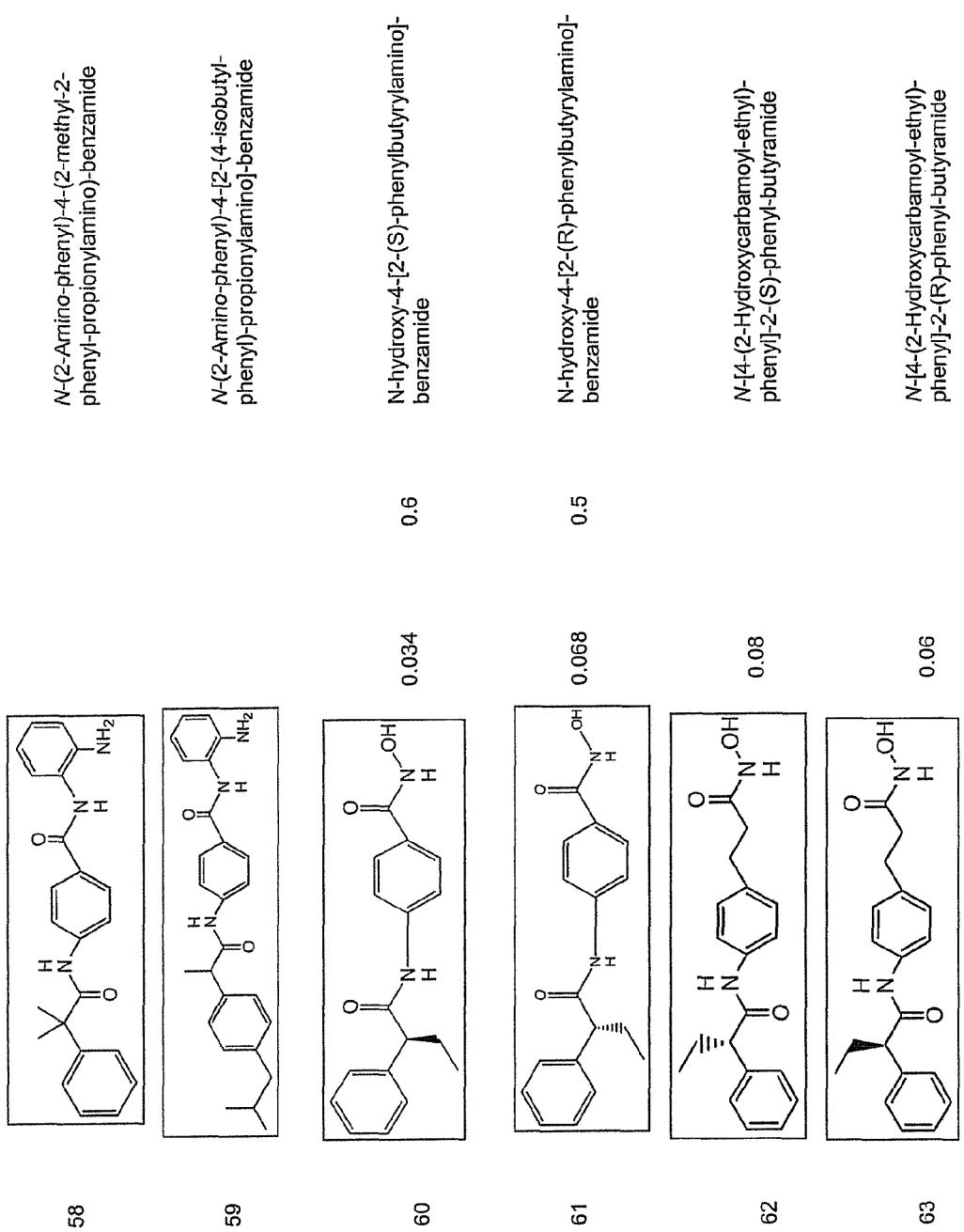
FIGURE 7 (Frame 10)

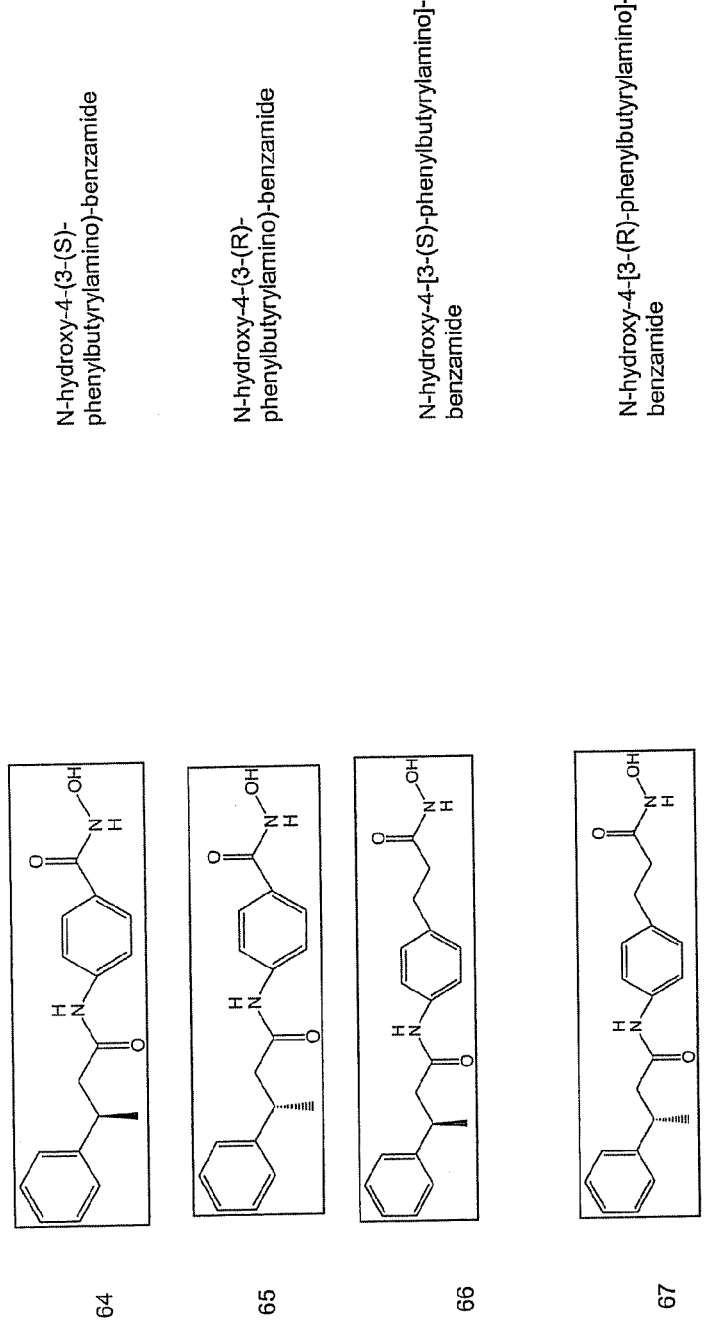
FIGURE 7 (Frame 11)

Zinc-chelating motifs:
| Structure | Name |
|---|---|
| 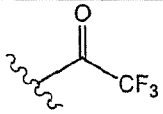 | Trifluoromethyl ketone |
| 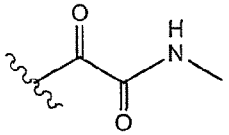 | α-keto Amide |
| 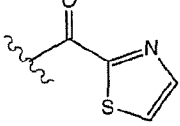 | α-keto Thiazole |
| 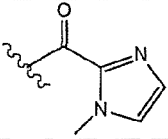 | 2-keto 1-Methyl-1*H*-imidazole |
| 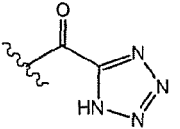 | α-keto 1*H*-Tetrazole |
| 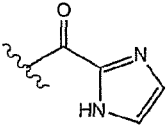 | α-keto 1*H*-Imidazole |
| 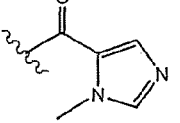 | 5-keto 1-Methyl-1*H*-imidazole |
| 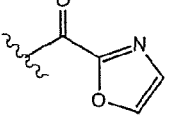 | α-keto Oxazole |
| 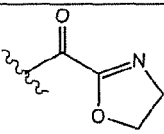 | α-keto 4,5-Dihydro-oxazole |
| 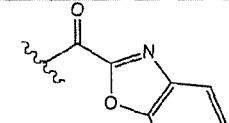 | α-keto Bezooxazole |
FIGURE 8 (Frame 1)

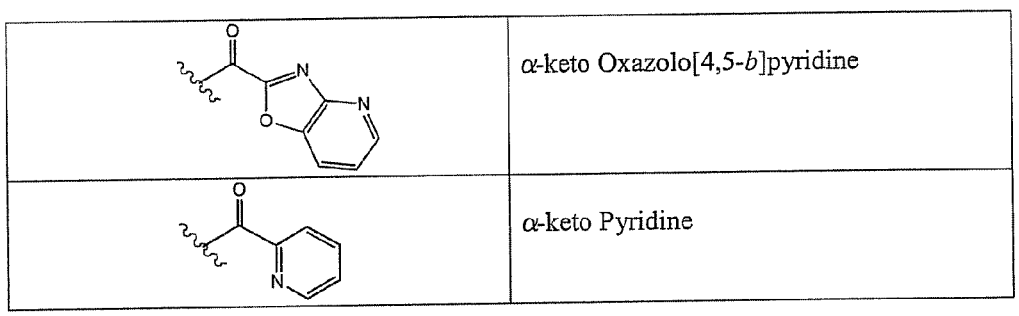
FIGURE 8 (Frame 2)

ZN²⁺ CHELATING MOTIF-TETHERED SHORT-CHAIN FATTY ACIDS AS A NOVEL CLASS OF HISTONE DEACETYLASE INHIBITORS

CONTINUING APPLICATION DATA

This application claims the benefit of U.S. patent application Ser. No. 10/597,022, filed on Jun. 18, 2007, which was a 35 USC 371 national stage submission of PCT/US04/40211, filed on Dec. 1, 2004, which claimed priority to provisional application 60/526,348, filed on Dec. 2, 2003, all of which are incorporated by reference herein.

This invention was supported by Army Grant DAMD17-02-1-0117 and National Institutes of Health Grant CA94829. The government has certain rights in this invention. This application claims priority to U.S. Provisional 60/526,348, filed Dec. 2, 2002.

FIELD OF THE INVENTION

The invention relates to histone deacetylase inhibitors, and in particular, those including $Zn^{2+}$-chelating motifs. More particularly, the invention relates to histone deacetylase inhibitors including $Zn^{2+}$-chelating motifs, based on short-chain fatty acids.

BACKGROUND OF THE INVENTION

The acetylation status of core histones plays a pivotal role in regulating gene transcription through the modulation of nucleosomal packaging of DNA (Kouzarides, "Histone acetylases and deacetylases in cell proliferation." *Curr Opin Genet Dev* 9: 40-48 (1999); Gray and Ekstrom, "The human histone deacetylase family." *Exp Cell Res* 262: 75-83 (2001); Jenuwein and Allis, "Translating the histone code." *Science* 293: 1074-1080 (2001)). In a hypoacetylated state, nucleosomes are tightly compacted, resulting in transcriptional repression due to restricted access of transcriptional factors to their targeted DNA. Conversely, histone acetylation leads to relaxed nucleosomal structures, giving rise to a transcriptionally permissive chromatin state. A dynamic balance between the activities of histone acetyltransferases (HATs) and histone deacetylases (HDACs), both of which are recruited to target genes in complexes with sequence-specific transcription activators, maintains this level of this posttranslational modification. Aberrant regulation of this epigenetic marking system has been shown to cause inappropriate gene expression, a key event in the pathogenesis of many forms of cancer (Wade, "Transcriptional control at regulatory checkpoints by histone deacetylases: molecular connections between cancer and chromatin." *Hum Mol Genet.* 10: 693-698 (2001); Cress and Seto, "Histone deacetylases, transcriptional control, and cancer." *J Cell Physiol* 184: 1-16 (2000); Marks et al., "Histone deacetylases and cancer: causes and therapies." *Nat Rev Cancer* 1: 194-202 (2001)). Moreover, evidence demonstrates that inhibition of HDAC triggers growth arrest, differentiation and/or apoptosis in many types of tumor cells by reactivating the transcription of a small number of genes (Jung, "Inhibitors of histone deacetylase as new anticancer agents." *Curr Med Chem* 8: 1505-1511 (2001); Grozinger and Schreiber, "Deacetylase enzymes: biological functions and the use of small-molecule inhibitors." *Chem Biol* 9: 3-16 (2002); Johnstone, "Histone-deacetylase inhibitors: novel drugs for the treatment of cancer." *Nat Rev Drug Discov* 1: 287-299 (2002); Kramer et al., "Histone deacetylase as a therapeutic target." *Trends Endocrinol Metab* 12: 294-300 (2001); Marks et al., "Histone deacetylase inhibitors: inducers of differentiation or apoptosis of transformed cells." *J Natl Cancer Inst* 92: 1210-1216 (2000)). Xenograft models also confirm these in vitro findings, suggesting that modulation of HDAC's function is a target for the prevention and/or therapeutic intervention of cancer.

To date, several structurally distinct classes of HDAC inhibitors have been reported (Jung, *Curr Med Chem* 8: 1505-1511 (2001); Grozinger and Schreiber, *Chem Biol* 9: 3-16 (2002); Johnstone, *Nat Rev Drug Discov* 1: 287-299 (2002); Kramer et al., *Trends Endocrinol Metab* 12: 294-300 (2001); Marks et al., *J Natl Cancer Inst* 92: 1210-1216 (2000)), including short-chain fatty acids (e.g., butyrate, valproate, phenylacetate, and phenylbutyrate) (Lea and Tuisyan, "Discordant effects of butyrate analogues on erythroleukemia cell proliferation, differentiation and histone deacetylase." *Anticancer Res* 15: 879-883 (1995); Kruh, "Effects of sodium butyrate, a new pharmacological agent, on cells in culture." *Mol Cell Biochem* 42: 65-82 (1982); Newmark and Young, "Butyrate and phenylacetate as differentiating agents: practical problems and opportunities." *J Cell Biochem Suppl* 22: 247-253 (1995); Phiel et al., "Histone deacetylase is a direct target of valproic acid, a potent anticonvulsant, mood stabilizer, and teratogen." *J Biol Chem* 276: 36734-36741 (2001)), benzamide derivatives (e.g., MS-27-275) (Suzuki et al., "Synthesis and histone deacetylase inhibitory activity of new benzamide derivatives." *J Med Chem* 42: 3001-3003 (1999); Saito et al., "A synthetic inhibitor of histone deacetylase, MS-27-275, with marked in vivo antitumor activity against human tumors. *Proc Natl Acad Sci USA* 96: 4592-4597 (1999)), trichostatin A (TSA) and analogues (Tsuji et al., "A new antifungal antibiotic, trichostatin." *J Antibiot (Tokyo)* 29: 1-6 (1976); Jung et al. "Amide analogues of trichostatin A as inhibitors of histone deacetylase and inducers of terminal cell differentiation." *J Med Chem* 42: 4669-4679 (1999); Furumai et al. "Potent histone deacetylase inhibitors built from trichostatin A and cyclic tetrapeptide antibiotics including trapoxin." *Proc Natl Acad Sci USA* 98: 87-92 (2001)), hybrid polar compounds (e.g., suberoylanilide hydroxamic acid (SAHA)) (Richon et al., "A class of hybrid polar inducers of transformed cell differentiation inhibits histone deacetylases." *Proc Natl Acad Sci USA* 95: 3003-3007 (1998); Remiszewski et al., "Inhibitors of human histone deacetylase: synthesis and enzyme and cellular activity of straight chain hydroxamates." *J Med Chem* 45: 753-757 (2002)), cyclic tetrapeptides (e.g., apicidin) (Kijima et al., "Trapoxin, an antitumor cyclic tetrapeptide, is an irreversible inhibitor of mammalian histone deacetylase." *J Biol Chem* 268: 22429-22435 (1993); Shute et al., "Analogues of the cytostatic and antimitogenic agents chlamydocin and HC-toxin: synthesis and biological activity of chloromethyl ketone and diazomethyl ketone functionalized cyclic tetrapeptides." *J Med Chem* 30: 71-78 (1987); Han et al., "Apicidin, a histone deacetylase inhibitor, inhibits proliferation of tumor cells via induction of p21WAF1/Cip1 and gelsolin." *Cancer Res* 60: 6068-6074 (2000); Nakajima et al., "FR901228, a potent antitumor antibiotic, is a novel histone deacetylase inhibitor." *Exp Cell Res* 241: 126-133 (1998)), and the depsipeptide FR901228 (Nakajima et al., *Exp Cell Res* 241: 126-133 (1998)). Among these agents, short-chain fatty acids are the least potent inhibitors with $IC_{50}$ in the mM range, as compared to that of μM or even nM for other types of HDAC inhibitors. Although the use of short-chain fatty acids in cancer treatment has been reported, their therapeutic efficacy has been limited by the low anti-proliferative activity, rapid metabolism, and non-specific mode of action.

Recently, X-ray crystallographic analysis of HDLP (histone deacetylase-like protein), a bacterial HDAC homologue, has suggested a distinctive mode of protein-ligand interactions whereby TSA and SAHA mediate enzyme inhibition (Finnin et al., "Structures of a histone deacetylase homologue bound to the TSA and SAHA inhibitors." Nature 401: 188-193 (1999)). The HDAC catalytic domain apparently consists of a narrow, tube-like pocket spanning the length equivalent to four to six-carbon straight chains. A $Zn^{2+}$ cation is positioned near the bottom of this enzyme pocket, which, in cooperation with two His-Asp charge-relay systems, is believed to facilitate the deacetylation catalysis.

Upon careful consideration of other work in the field, we realized that the weak potency of short-chain fatty acids in HDAC inhibition was, in part, attributable to their inability to access the $Zn^{2+}$ cation in the active-site pocket, which we believe plays a pivotal role in the deacetylation catalysis. Based on this realization and further study, we structurally modified short-chain fatty acids by tethering them with a $Zn^{2+}$-chelating motif via an aromatic linker. Our discoveries and study have led us to the invention of a new class of $Zn^{2+}$-chelating motif-tethered short-chain fatty acids, some of which show inhibition of HDAC activity and cancer cell proliferation in nM range, a three-orders-of-magnitude improvement over their parent compounds.

SUMMARY OF THE INVENTION

We realized that the weak potency of short-chain fatty acids as histone deacetylase (HDAC) inhibitors was, in part, attributable to their inability to access the zinc cation in the HDAC active-site pocket, which is believed to be important in deacetylation catalysis. The present invention is based on structural modification of fatty acids, including the short-chain fatty acids, e.g., valproate, butyrate, phenylacetate, and phenylbutyrate. The present invention generally includes coupling fatty acids with $Zn^{2+}$-chelating motifs (including, but not limited to, hydroxamic acid and o-phenylene diamine) through aromatic ω-amino acid linkers. This strategy has led to the present invention, which includes a novel class of $Zn^{2+}$-chelating motif-tethered short-chain fatty acids.

The efficacy of the inventive compounds in HDAC inhibition demonstrates that potent HDAC inhibitors can be designed based on the framework provided by the crystal structures of HDLP-ligand complexes. The present invention is based on a tethering strategy that allows the generation of a large library of compounds via the divergent combination of short-chain fatty acids, ω-amino acids, and a zinc-chelator, such as hydroxamate.

The present invention includes histone deacetylase inhibitors having the formula:

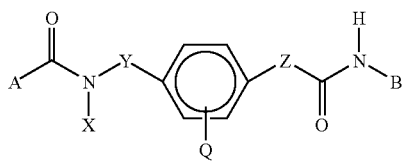

wherein:
X is chosen from H and $CH_3$;
Y is $(CH_2)_n$ wherein n is 0-2;
Z is chosen from $(CH_2)_m$ wherein m is 0-3 and $(CH_2)_2$;
A is a hydrocarbyl group;
B is o-aminophenyl or hydroxyl group; and
Q is a halogen, hydrogen, or methyl.

In one embodiment, A can comprise an aliphatic group, and the aliphatic group can be branched. A can also comprise an aromatic group, which may be substituted or unsubstituted. In the formula, B can be o-aminophenyl or hydroxyl. In some embodiments Y can be $(CH_2)_n$ wherein n is 0, A comprises an aromatic group, B is hydroxy, and Q is hydrogen.

In some specific embodiments, m is 0 and X is H. Compounds having these features include, but are not limited to,

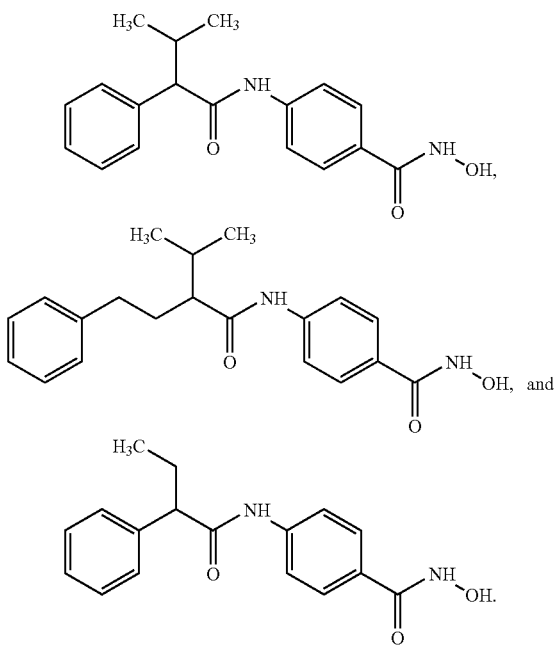

In some specific embodiments, X is H and A is chosen from:

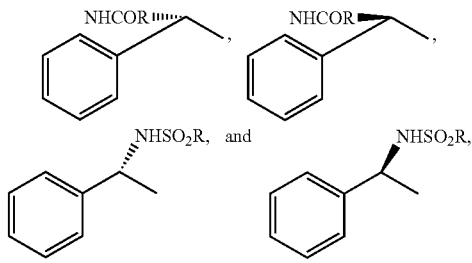

wherein R comprises a branched or unbranched, substituted or unsubstituted, saturated or unsaturated, aliphatic or aromatic group.

The present invention also includes compositions comprising the inhibitor according to the invention, wherein the composition is enriched in the S-stereoisomer as compared to the R-stereoisomer.

Specific inhibitors of the invention include N-(2-Amino-phenyl)-4-[(2-propyl-pentanoylamino)-methyl]-benzamide; N-Hydroxy-4-[(2-propyl-pentanoylamino)-methyl]-benzamide; N-(2-Amino-phenyl)-4-(2-propyl-pentanoylamino)-benzamide; N-Hydroxy-4-(2-propyl-pentanoylamino)-benzamide; 2-Propyl-pentanoic acid {4-[2-amino-phenylcarbamoyl)-methyl]-phenyl}-amide; 2-Propyl-pentanoic acid (4-hydroxycarbamoyl-methyl-phenyl)-amide; 2-Propyl-pentanoic acid {4-[2-amino-phenylcarbamoyl)-ethyl]-phenyl}-amide; 2-Propyl-pentanoic acid [4-(2-hydroxycarbamoyl-ethyl)-phenyl]- amide; 2-Propyl-pentanoic acid {4-2-(2-amino-phenylcarbamoyl)-vinyl]-phenyl}-amide; 2-Propyl-pentanoic acid [4-(2-hydroxycarbamoyl-vinyl)-phenyl]-amide; N-(2-Aminophenyl)-4-(butyrylamino-methyl)-benzamide; N-(2-Aminophenyl)-4-(phenylacetylamino-methyl)-benzamide; N-(2-Amino-phenyl)-4-[(4-phenyl-butyrylamino-methyl]-benzamide; 4-(Butyrylamino-methyl)-N-hydroxy-benzamide; N-hydroxy-4-(phenylacetylamino-methyl)-benzamide; N-hydroxy-4-[(4-phenyl-butyrylamino)-methyl]-benzamide; 4-Butyrylamino-N-hydroxy-benzamide; N-hydroxy-4-phenylacetylamino-benzamide; N-hydroxy-4-(4-phenylbutyrylamino)-benzamide; N-[4-(2-Hydroxycarbamoyl-ethyl)-phenyl]-butyramide; N-hydroxy-3-(4-phenylacetylamino-phenyl)-propionamide; N-[4-(2-Hydroxycarbamoyl-ethyl)-phenyl]-4-phenyl-butyramide; N-(2-Amino-phenyl)-4-[(2-phenyl-butyrylamino-methyl]-benzamide; N-(2-Amino-phenyl)-4-[(3-phenyl-butyrylamino-methyl]-benzamide; N-hydroxy-4-(2-phenylbutyrylamino)-benzamide; N-hydroxy-4-(3-phenylbutyrylamino)-benzamide; N-[4-(2-Hydroxycarbamoyl-ethyl)-phenyl]-2-phenyl-butyramide; N-[4-(2-Hydroxycarbamoyl-ethyl)-phenyl]-3-phenyl-butyramide; N-hydroxy-4-[(2-phenyl-butyrylamino)-methyl]-benzamide; N-hydroxy-4-[(3-phenyl-butyrylamino)-methyl]-benzamide; 4-Benzoylamino-N-hydroxy-benzamide; 4-(4-methyl)-Benzoylamino-N-hydroxy-benzamide; 4-(4-chloro)-Benzoylamino-N-hydroxy-benzamide; 4-(4-bromo)-Benzoylamino-N-hydroxy-benzamide; 4-(4-tert-butyl)-Benzoylamino-N-hydroxy-benzamide; 4-(4-phenyl)-Benzoylamino-N-hydroxy-benzamide; 4-(4-methoxyl)-Benzoylamino-N-hydroxy-benzamide; 4-(4-trifluoromethyl)-Benzoylamino-N-hydroxy-benzamide; 4-(4-nitro)-Benzoylamino-N-hydroxy-benzamide; Pyridine-2-carboxylic acid (4-hydroxycarbamoyl-phenyl)-amide; N-hydroxy-4-(2-methyl-2-phenyl-propionylamino)-benzamide; N-hydroxy-4-(3-methyl-2-phenyl-butyrylamino)-benzamide; N-hydroxy-4-(3-phenyl-propionylamino)-benzamide; 4-(2,2-Dimethyl-4-phenyl-butyrylamino)-N-hydroxy-benzamide; N-hydroxy-4-[methyl-(4-phenyl-butyryl)-amino]-benzamide; N-hydroxy-4-(2-phenyl-propionylamino)-benzamide; N-hydroxy-4-(2-methoxy-2-phenyl-acetylamino)-benzamide; 4-Diphenylacetylamino-N-hydroxy-benzamide; N-hydroxy-4-[2-(4-isobutyl-phenyl)-propionylamino]-benzamide; N-(2-Amino-phenyl)-4-phenylacetylamino-benzamide; N-(2-Amino-phenyl)-4-(5-phenyl-pentanoylamino)-benzamide; N-(2-Amino-phenyl)-4-(2-phenyl-butyrylamino)-benzamide; N-(2-Amino-phenyl)-4-(2,2-dimethyl-4-phenyl-butyrylamino)-benzamide; N-(2-Amino-phenyl)-4-(3-phenyl-propionylamino)-benzamide; N-(2-Amino-phenyl)-4-(4-phenyl-butyrylamino)-benzamide; N-(2-Amino-phenyl)-4-(3-phenyl-butyrylamino)-benzamide; N-(2-Amino-phenyl)-4-(3-methyl-2-phenyl-butyrylamino)-benzamide; N-(2-Amino-phenyl)-4-(2-methyl-2-phenyl-propionylamino)-benzamide; N-(2-Amino-phenyl)-4-[2-(4-isobutyl-phenyl)-propionylamino]-benzamide; and N-hydroxy-4-[2-(S)-phenylbutyrylamino]-benzamide; N-hydroxy-4-[2-(R)-phenylbutyrylamino]-benzamide; N-[4-(2-Hydroxycarbamoyl-ethyl)-phenyl]-2-(S)-phenyl-butyramide; N-[4-(2-Hydroxycarbamoyl-ethyl)-phenyl]-2-(R)-phenyl-butyramide; N-hydroxy-4-(3-(S)-phenylbutyrylamino)-benzamide; N-hydroxy-4-(3-(R)-phenylbutyrylamino)-benzamide; N-hydroxy-4-[3-(S)-phenylbutyrylamino]-benzamide; and N-hydroxy-4-[3-(R)-phenylbutyrylamino]-benzamide.

The present invention also includes pharmaceutical compositions comprising these inhibitors, and at least one pharmaceutically acceptable excipient. Still further, the invention includes methods of inhibiting neoplastic cell proliferation in an animal, such as a human, comprising administering a therapeutically effective amount of at least one inhibitor of the invention.

Additional features and advantages of the invention will be set forth in part in the description which follows, and in part will be obvious from the description, or may be learned by practice of the invention. The features and advantages of the invention will be realized and attained by means of the elements and combinations particularly pointed out in the appended claims.

It is to be understood that both the foregoing general description and the following detailed description are exemplary and explanatory only and are not restrictive of the invention, as claimed. The accompanying drawings, which are incorporated in and constitute a part of this specification, illustrate embodiments of the invention and together with the description, serve to explain the principles of the invention.

BRIEF DESCRIPTION OF THE DRAWINGS

FIG. 3 shows structures and HDAC inhibitory potency of compounds 11-22. Values are the means±S.D. (n=3).

FIG. 6 illustrates examples of schemes for synthesizing compounds according to the invention.

FIG. 7 (Frames 1-11) displays examples of different compounds according to the invention.

FIG. 8 (Frames 1 and 2) displays examples of zinc-chelating motifs that can be used in accordance with the invention.

DESCRIPTION OF EMBODIMENTS OF THE INVENTION

Figure 1:
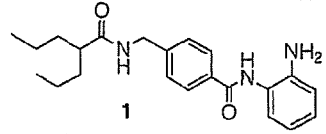
FIG. 1 shows divergent conjugations of valproic acid with five aromatic ω-amino acids and two $Zn^{2+}$-chelating moieties to generate compounds 1-10.

In general, short-chain fatty acids exhibit HDAC inhibitory and antiproliferative activities in the mM range irrespective of the structure of acyl chains (Grozinger and Schreiber, *Chem Biol* 9: 3-16 (2002); Johnstone, *Nat Rev Drug Discov* 1: 287-299 (2002); Kramer et al., *Trends Endocrinol Metab* 12: 294-300 (2001)). The present invention is based on, among other things, the discovery that these fatty acids exert HDAC inhibition through non-specific hydrophobic interactions with surface residues located at the enzyme pocket entrance and/or the hydrophobic region inside the tube-like pocket. We enhanced the HDAC inhibitory potency of these short-chain fatty acids by tethering to a $Zn^{2+}$-chelating moiety through a hydrophobic spacer.

Measurement of the enzymatic activity of a histone deacetylase can be achieved using known methodologies. For example, Yoshida et al. (*J. Biol. Chem.* 265: 17174-17179 (1990)) describe the assessment of histone deacetylase enzymatic activity by the detection of acetylated histones in trichostatin A treated cells. Taunton et al. (*Science* 272: 408-411 (1996)) similarly describes methods to measure histone deacetylase enzymatic activity using endogenous and recombinant HDAC-1. Both Yoshida et al. (J. Biol. Chem. 265: 17174-17179, 1990) and Taunton et al. (Science 272: 408-411, 1996) are incorporated herein by reference.

Throughout this disclosure, reference will be made to compounds according to the invention. Reference to such compounds, in the specification and claims, includes esters and salts of such compounds. Thus, even if not explicitly recited, such esters and salts are contemplated, and encompassed, by reference to the compounds themselves.

The fatty acids that can be used in accordance with the present invention comprise a hydrocarbyl portion and a carboxylic acid portion. As used herein, the term "hydrocarbyl" is understood to include "aliphatic," "cycloaliphatic," and "aromatic." The hydrocarbyl groups are understood to include alkyl, alkenyl, alkynyl, cycloalkyl, aryl, aralkyl, and alkaryl groups. Further, "hydrocarbyl" is understood to include both non-substituted hydrocarbyl groups, and substituted hydrocarbyl groups, with the latter referring to the hydrocarbon portion bearing additional substituents, besides carbon and hydrogen. Additionally, while "carboxylic acid" is used to refer to the compounds, salts of such acids, i.e., carboxylates, are also expressly contemplated. Moreover, carboxylic acids and carboxylates may be used interchangably herein.

In particular, fatty acids include, but are not limited to, those having chain lengths comparable to an unbranched fatty acid of from about 3 carbons to about 14 carbons in length. Thus, the chains can be, for example, from about 3, 4, 5, 6, 7, 8, 9, 10, 11, 12, or 13 carbons in length. The chains can be up to, for example, about 14, 13, 12, 11, 9, 8, 7, 6, 5, or 4 carbons in length. The fatty acids can be straight or branched and can include single, double, and/or triple bonds. Nonlimiting examples of fatty acids include valproate, butyrate, phenylacetate, and phenylbutyrate.

$Zn^{2+}$-chelating motifs contemplated in accordance with the present invention include, but are not limited to, hydroxamic acids and o-phenylene diamines. Other examples include trifluoromethyl ketone, α-keto amide, α-keto thiazole, 2-keto 1-methyl-1 H-imidazole, α-keto 1 H-tetrazole, α-keto 1 H-imidazole, 5-keto 1-methyl-1 H-imidazole, α-keto oxazole, α-keto 4,5-dihydro-oxazole, α-keto benzooxazole, α-keto oxazolo[4,5-b]pyridine, and α-keto pyridine. Structures of these motifs are shown in FIG. 8.

The spacer can be any hydrocarbyl spacer, but preferably comprises an aromatic component. Aromatic linkers are believed to possess the following advantages: 1) they enhance the structural rigidity of the conjugate, and 2) they increase van der Waals contacts with the tube-like hydrophobic region of the pocket to improve binding affinity. Examples of linkers include, but are not limited to, aromatic ω-amino acids.

The linkers can exhibit lengths equivalent to that of four to eight-carbon straight chains, e.g., equivalent to 4, 5, 6, 7, or 8-carbon straight chains. Thus, the lengths can be equivalent to 4-7 or 4-6-carbon straight chains. The length may be based on the depth of the hydrophobic region of the binding pocket. Examples of linkers of the invention include, but are not limited to, 4-(aminomethyl)benzoic acid, 4-aminobenzoic acid, (4-aminophenyl)acetic acid, 3-(4-aminophenyl)propionic acid, and 3-(4-aminophenyl)-acrylic acid. Among them, 4-(aminomethyl)benzoic acid has been used as the linker for MS-27-275 (Saito et al., *Proc Natl Acad Sci USA* 96: 4592-4597 (1999)).

The following compounds are specifically contemplated:
N-(2-Amino-phenyl)-4-[(2-propyl-pentanoylamino)-methyl]-benzamide;
N-Hydroxy-4-[(2-propyl-pentanoylamino)-methyl]-benzamide;
N-(2-Amino-phenyl)-4-(2-propyl-pentanoylamino)-benzamide;
N-Hydroxy-4-(2-propyl-pentanoylamino)-benzamide;
2-Propyl-pentanoic acid {4-[2-amino-phenylcarbamoyl)-methyl]-phenyl}-amide;
2-Propyl-pentanoic acid (4-hydroxycarbamoyl-methyl-phenyl)-amide;
2-Propyl-pentanoic acid {4-[2-amino-phenylcarbamoyl)-ethyl]-phenyl}-amide;
2-Propyl-pentanoic acid [4-(2-hydroxycarbamoyl-ethyl)-phenyl]-amide;
2-Propyl-pentanoic acid {4-2-(2-amino-phenylcarbamoyl)-vinyl]-phenyl}-amide;
2-Propyl-pentanoic acid [4-(2-hydroxycarbamoyl-vinyl)-phenyl]-amide;
N-(2-Amino-phenyl)-4-(butyrylamino-methyl)-benzamide;
N-(2-Amino-phenyl)-4-(phenylacetylamino-methyl)-benzamide;
N-(2-Amino-phenyl)-4-[(4-phenyl-butyrylamino-methyl]-benzamide;
4-(Butyrylamino-methyl)-N-hydroxy-benzamide;

N-hydroxy-4-(phenylacetylamino-methyl)-benzamide;
N-hydroxy-4-[(4-phenyl-butyrylamino)-methyl]-benzamide;
4-Butyrylamino-N-hydroxy-benzamide;
N-hydroxy-4-phenylacetylamino-benzamide;
N-hydroxy-4-(4-phenylbutyrylamino)-benzamide;
N-[4-(2-Hydroxycarbamoyl-ethyl)-phenyl]-butyramide;
N-hydroxy-3-(4-phenylacetylamino-phenyl)-propionamide;
N-[4-(2-Hydroxycarbamoyl-ethyl)-phenyl]-4-phenyl-butyramide;
N-(2-Amino-phenyl)-4-[(2-phenyl-butyrylamino-methyl]-benzamide;
N-(2-Amino-phenyl)-4-[(3-phenyl-butyrylamino-methyl]-benzamide;
N-hydroxy-4-(2-phenylbutyrylamino)-benzamide;
N-hydroxy-4-(3-phenylbutyrylamino)-benzamide;
N-[4-(2-Hydroxycarbamoyl-ethyl)-phenyl]-2-phenyl-butyramide;
N-[4-(2-Hydroxycarbamoyl-ethyl)-phenyl]-3-phenyl-butyramide;
N-hydroxy-4-[(2-phenyl-butyrylamino)-methyl]-benzamide;
N-hydroxy-4-[(3-phenyl-butyrylamino)-methyl]-benzamide;
4-Benzoylamino-N-hydroxy-benzamide;
4-(4-methyl)-Benzoylamino-N-hydroxy-benzamide;
4-(4-chloro)-Benzoylamino-N-hydroxy-benzamide;
4-(4-bromo)-Benzoylamino-N-hydroxy-benzamide;
4-(4-tert-butyl)-Benzoylamino-N-hydroxy-benzamide;
4-(4-phenyl)-Benzoylamino-N-hydroxy-benzamide;
4-(4-methoxyl)-Benzoylamino-N-hydroxy-benzamide;
4-(4-trifluoromethyl)-Benzoylamino-N-hydroxy-benzamide;
4-(4-nitro)-Benzoylamino-N-hydroxy-benzamide;
Pyridine-2-carboxylic acid (4-hydroxycarbamoyl-phenyl)-amide;
N-hydroxy-4-(2-methyl-2-phenyl-propionylamino)-benzamide;
N-hydroxy-4-(3-methyl-2-phenyl-butyrylamino)-benzamide;
N-hydroxy-4-(3-phenyl-propionylamino)-benzamide;
4-(2,2-Dimethyl-4-phenyl-butyrylamino)-N-hydroxy-benzamide;
N-hydroxy-4-[methyl-(4-phenyl-butyryl)-amino]-benzamide;
N-hydroxy-4-(2-phenyl-propionylamino)-benzamide;
N-hydroxy-4-(2-methoxy-2-phenyl-acetylamino)-benzamide;
4-Diphenylacetylamino-N-hydroxy-benzamide;
N-hydroxy-4-[2-(4-isobutyl-phenyl)-propionylamino]-benzamide;
N-(2-Amino-phenyl)-4-phenylacetylamino-benzamide;
N-(2-Amino-phenyl)-4-(5-phenyl-pentanoylamino)-benzamide;
N-(2-Amino-phenyl)-4-(2-phenyl-butyrylamino)-benzamide;
N-(2-Amino-phenyl)-4-(2,2-dimethyl-4-phenyl-butyrylamino)-benzamide;
N-(2-Amino-phenyl)-4-(3-phenyl-propionylamino)-benzamide;
N-(2-Amino-phenyl)-4-(4-phenyl-butyrylamino)-benzamide;
N-(2-Amino-phenyl)-4-(3-phenyl-butyrylamino)-benzamide;
N-(2-Amino-phenyl)-4-(3-methyl-2-phenyl-butyrylamino)-benzamide;
N-(2-Amino-phenyl)-4-(2-methyl-2-phenyl-propionylamino)-benzamide;
N-(2-Amino-phenyl)-4-[2-(4-isobutyl-phenyl)-propionylamino]-benzamide;
N-hydroxy-4-[2-(S)-phenylbutyrylamino]-benzamide;
N-hydroxy-4-[2-(R)-phenylbutyrylamino]-benzamide;
N-[4-(2-Hydroxycarbamoyl-ethyl)-phenyl]-2-(S)-phenyl-butyramide;
N-[4-(2-Hydroxycarbamoyl-ethyl)-phenyl]-2-(R)-phenyl-butyramide;
N-hydroxy-4-(3-(S)-phenylbutyrylamino)-benzamide;
N-hydroxy-4-(3-(R)-phenylbutyrylamino)-benzamide;
N-hydroxy-4-[3-(S)-phenylbutyrylamino]-benzamide; and
N-hydroxy-4-[3-(R)-phenylbutyrylamino]-benzamide.

The compounds of the invention may be racemates, or racemic mixtures. The term "racemic" as used herein means a mixture of the (R)- and (S)-enantiomers, or stereoisomers, of the compounds of the invention, in which neither enantiomer, or stereoisomer, is substantially purified from the other.

The term "enriched," as used herein to describe (R)- or (S)-stereoisomers of the invention, refers to a composition having a greater amount of the (R)-stereoisomer than (S)-stereoisomer, or vice versa. For example, the composition may contain greater than 50%, 55%, or at least about 60% of the (S)-stereoisomer of compound 42 by weight, based on the total weight of compound 42. In one embodiment, the amount of enriched (S)-compound 42 may be higher, for example, at least about 65%, 70%, 75%, 80%, 81%, 82%, 83%, 84%, 85%, 86%, 87%, 88%, 89%, 90%, 91%, 92%, 93%, 94%, 95%, 96%, 97%, 98%, 99%, or any fraction thereof (i.e., 90.1%, 90.2%, etc.), of (S)-compound 42 by weight, based on the total weight of compound 42. In a particular embodiment, the amount of enriched (S)-compound 42 may be greater than 99%, 99.1%, 99.2%, 99.3%, 99.4%, 99.5%, 99.6%, 99.7%, 99.8%, 99.9% or may be 100%, by weight, based on the total weight of compound 42. These terms also define the amount of any pharmaceutically acceptable salts of (S)-compound 42. These are non-limiting examples, and the same enrichments may be achieved for other racemic compounds of the invention.

The administration of enantiomerically enriched compositions of the invention may result in a desirable therapeutic effect. That is, administration of enantiomerically enriched compositions may produce a therapeutic effect at a lower total concentration, or may reduce side effects resulting from the presence of the less-desirable enantiomer. These advantages are specifically contemplated.

Any of the inventive compounds, employed in the methods of the invention, can be administered orally, parenterally (IV, IM, depot-IM, SQ, and depot-SQ), sublingually, intranasally (inhalation), intrathecally, topically, or rectally. Dosage forms known to those of skill in the art are suitable for delivery of the inventive compounds employed in the methods of the invention.

Compositions are provided that contain therapeutically effective amounts of the inventive compounds employed in the methods of the invention. The compounds can be formulated into suitable pharmaceutical preparations such as tablets, capsules, or elixirs for oral administration or in sterile solutions or suspensions for parenteral administration. The compounds described herein can be formulated into pharmaceutical compositions using techniques and procedures well known in the art.

About 0.1 to 1000 mg of an inventive compound or mixture of inventive compounds employed in the methods of the invention, or a physiologically acceptable salt or ester is compounded with a physiologically acceptable vehicle, carrier, excipient, binder, preservative, stabilizer, flavor, etc., in a unit dosage form as called for by accepted pharmaceutical practice. The amount of active substance in those compositions or preparations is such that a suitable dosage in the range indicated is obtained. The compositions can be formulated in a unit dosage form, each dosage containing from about 1 to about 500 mg, or about 10 to about 100 mg of the active ingredient. The term "unit dosage from" refers to physically discrete units suitable as unitary dosages for human subjects and other mammals, each unit containing a predetermined quantity of active material calculated to produce the desired therapeutic effect, in association with a suitable pharmaceutical excipient.

To prepare compositions, one or more inventive compounds employed in the methods of the invention are mixed with a suitable pharmaceutically acceptable carrier. Upon mixing or addition of the compound(s), the resulting mixture may be a solution, suspension, emulsion, or the like. Liposomal suspensions may also be used as pharmaceutically acceptable carriers. These may be prepared according to methods known to those skilled in the art. The form of the resulting mixture depends upon a number of factors, including the intended mode of administration and the solubility of the compound in the selected carrier or vehicle. The effective concentration is sufficient for lessening or ameliorating at least one symptom of the disease, disorder, or condition treated and may be empirically determined.

Pharmaceutical carriers or vehicles suitable for administration of the compounds provided herein include any such carriers suitable for the particular mode of administration. In addition, the active materials can also be mixed with other active materials that do not impair the desired action, or with materials that supplement the desired action, or have another action. The compounds may be formulated as the sole pharmaceutically active ingredient in the composition or may be combined with other active ingredients.

Where the compounds exhibit insufficient solubility, methods for solubilizing may be used. Such methods are known and include, but are not limited to, using co-solvents such as dimethylsulfoxide (DMSO), using surfactants such as TWEEN, and dissolution in aqueous sodium bicarbonate. Derivatives of the compounds, such as salts or prodrugs, may also be used in formulating effective pharmaceutical compositions.

The concentration of the compound is effective for delivery of an amount upon administration that lessens or ameliorates at least one symptom of the disorder for which the compound is administered. Typically, the compositions are formulated for single dosage administration.

The inventive compounds employed in the methods of the invention may be prepared with carriers that protect them against rapid elimination from the body, such as time-release formulations or coatings. Such carriers include controlled release formulations, such as, but not limited to, microencapsulated delivery systems. The active compound can be included in the pharmaceutically acceptable carrier in an amount sufficient to exert a therapeutically useful effect in the absence of undesirable side effects on the patient treated. The therapeutically effective concentration may be determined empirically by testing the compounds in known in vitro and in vivo model systems for the treated disorder.

The compounds and compositions of the invention can be enclosed in multiple or single dose containers. The enclosed compounds and compositions can be provided in kits, for example, including component parts that can be assembled for use. For example, an inventive compound in lyophilized form and a suitable diluent may be provided as separated components for combination prior to use. A kit may include an inventive compound and a second therapeutic agent for co-administration. The inventive compound and second therapeutic agent may be provided as separate component parts. A kit may include a plurality of containers, each container holding one or more unit dose of the inventive compound employed in the method of the invention. The containers can be adapted for the desired mode of administration, including, but not limited to tablets, gel capsules, sustained-release capsules, and the like for oral administration; depot products, pre-filled syringes, ampoules, vials, and the like for parenteral administration; and patches, medipads, creams, and the like for topical administration.

The concentration of active inventive compound in the drug composition will depend on absorption, inactivation, and excretion rates of the active compound, the dosage schedule, and amount administered as well as other factors known to those of skill in the art.

The active ingredient may be administered at once, or may be divided into a number of smaller doses to be administered at intervals of time. It is understood that the precise dosage and duration of treatment is a function of the disease being treated and may be determined empirically using known testing protocols or by extrapolation from in vivo or in vitro test data. It is to be noted that concentrations and dosage values may also vary with the severity of the condition to be alleviated. It is to be further understood that for any particular subject, specific dosage regimens should be adjusted over time according to the individual need and the professional judgment of the person administering or supervising the administration of the compositions, and that the concentration ranges set forth herein are exemplary only and are not intended to limit the scope or practice of the claimed compositions.

If oral administration is desired, the compound can be provided in a composition that protects it from the acidic environment of the stomach. For example, the composition can be formulated in an enteric coating that maintains its integrity in the stomach and releases the active compound in the intestine. The composition may also be formulated in combination with an antacid or other such ingredient.

Oral compositions will generally include an inert diluent or an edible carrier and may be compressed into tablets or enclosed in gelatin capsules. For the purpose of oral therapeutic administration, the active compound or compounds can be incorporated with excipients and used in the form of tablets, capsules, or troches. Pharmaceutically compatible binding agents and adjuvant materials can be included as part of the composition.

The tablets, pills, capsules, troches, and the like can contain any of the following ingredients or compounds of a similar nature: a binder such as, but not limited to, gum tragacanth, acacia, corn starch, or gelatin; an excipient such as microcrystalline cellulose, starch, or lactose; a disintegrating agent such as, but not limited to, alginic acid and corn starch; a lubricant such as, but not limited to, magnesium stearate; a glidant, such as, but not limited to, colloidal silicon dioxide; a sweetening agent such as sucrose or saccharin; and a flavoring agent such as peppermint, methyl salicylate, or fruit flavoring.

When the dosage unit form is a capsule, it can contain, in addition to material of the above type, a liquid carrier such as a fatty oil. In addition, dosage unit forms can contain various other materials, which modify the physical form of the dosage unit, for example, coatings of sugar and other enteric agents. The compounds can also be administered as a component of an elixir, suspension, syrup, wafer, chewing gum or the like.

A syrup may contain, in addition to the active compounds, sucrose as a sweetening agent and certain preservatives, dyes and colorings, and flavors.

The active materials can also be mixed with other active materials that do not impair the desired action, or with materials that supplement the desired action. The inventive compounds can be used, for example, in combination with an antitumor agent, a hormone, a steroid, or a retinoid. The antitumor agent may be one of numerous chemotherapy agents such as an alkylating agent, an antimetabolite, a hormonal agent, an antibiotic, colchicine, a vinca alkaloid, L-asparaginase, procarbazine, hydroxyurea, mitotane, nitrosoureas or an imidazole carboxamide. Suitable agents include those agents which promote depolarization of tubulin. Examples include colchicine and vinca alkaloids, including vinblastine and vincristine.

Solutions or suspensions used for parenteral, intradermal, subcutaneous, or topical application can include any of the following components: a sterile diluent such as water for injection, saline solution, fixed oil, a naturally occurring vegetable oil such as sesame oil, coconut oil, peanut oil, cottonseed oil, and the like, or a synthetic fatty vehicle such as ethyl oleate, and the like, polyethylene glycol, glycerin, propylene glycol, or other synthetic solvent; antimicrobial agents such as benzyl alcohol and methyl parabens; antioxidants such as ascorbic acid and sodium bisulfite; chelating agents such as ethylenediaminetetraacetic acid (EDTA); buffers such as acetates, citrates, and phosphates; and agents for the adjustment of tonicity such as sodium chloride and dextrose. Parenteral preparations can be enclosed in ampoules, disposable syringes, or multiple dose vials made of glass, plastic, or other suitable material. Buffers, preservatives, antioxidants, and the like can be incorporated as required.

Where administered intravenously, suitable carriers include, but are not limited to, physiological saline, phosphate buffered saline (PBS), and solutions containing thickening and solubilizing agents such as glucose, polyethylene glycol, polypropyleneglycol, and mixtures thereof. Liposomal suspensions including tissue-targeted liposomes may also be suitable as pharmaceutically acceptable carriers. These may be prepared according to methods known in the art.

The inventive compounds may be prepared with carriers that protect the compound against rapid elimination from the body, such as time-release formulations or coatings. Such carriers include controlled release formulations, such as, but not limited to, implants and microencapsulated delivery systems, and biodegradable, biocompatible polymers such as collagen, ethylene vinyl acetate, polyanhydrides, polyglycolic acid, polyorthoesters, polylactic acid, and the like. Methods for preparation of such formulations are known to those skilled in the art.

Compounds employed in the methods of the invention may be administered enterally or parenterally. When administered orally, compounds employed in the methods of the invention can be administered in usual dosage forms for oral administration as is well known to those skilled in the art. These dosage forms include the usual solid unit dosage forms of tablets and capsules as well as liquid dosage forms such as solutions, suspensions, and elixirs. When the solid dosage forms are used, they can be of the sustained release type so that the compounds employed in the methods of the invention need to be administered only once or twice daily.

The oral dosage forms can be administered to the patient 1, 2, 3, or 4 times daily. The inventive compounds employed in the methods of the invention can be administered either three or fewer times, or even once or twice daily. Hence, the inventive compounds employed in the methods of the invention be administered in oral dosage form. Whatever oral dosage form is used, they can be designed so as to protect the compounds employed in the methods of the invention from the acidic environment of the stomach. Enteric coated tablets are well known to those skilled in the art. In addition, capsules filled with small spheres each coated to protect from the acidic stomach, are also well known to those skilled in the art.

The inventive compounds employed in the methods of the invention may also be advantageously delivered in a nanocrystal dispersion formulations. Preparation of such formulations is described, for example, in U.S. Pat. No. 5,145,684, the entire contents of which is incorporated by reference. Nanocrystalline dispersions of HIV protease inhibitors and their method of use are described in U.S. Pat. No. 6,045,829, the entire contents of which is incorporated by reference. The nanocrystalline formulations typically afford greater bioavailability of drug compounds.

The inventive compounds and methods can be used to inhibit neoplastic cell proliferation in an animal. The methods comprise administering to an animal having at least one neoplastic cell present in its body a therapeutically effective amount of at least one of the inventive compounds, in compositions as described above. The animal can be a mammal, including a domesticated mammal. The animal can be a human.

The term "neoplastic cell" is used to denote a cell that shows aberrant cell growth. The aberrant cell growth of a neoplastic cell includes increased cell growth. A neoplastic cell may be, for example, a hyperplastic cell, a cell that shows a lack of contact inhibition of growth in vitro, a benign tumor cell that is incapable of metastasis in vivo, or a cancer cell that is capable of metastases in vivo and that may recur after attempted removal. The term "tumorigenesis" is used to denote the induction of cell proliferation that leads to the development of a neoplastic growth.

The terms "therapeutically effective amount" and "therapeutically effective period of time" are used to denote treatments at dosages and for periods of time effective to reduce neoplastic cell growth. As noted above, such administration can be parenteral, oral, sublingual, transdermal, topical, intranasal, or intrarectal. When administered systemically, the therapeutic composition can be administered at a sufficient dosage to attain a blood level of the inventive compounds of from about 0.1 µM to about 100 mM. For localized administration, much lower concentrations than this can be effective, and much higher concentrations may be tolerated. One of skill in the art will appreciate that such therapeutic effect resulting in a lower effective concentration of the histone deacetylase inhibitor may vary considerably depending on the tissue, organ, or the particular animal or patient to be treated according to the invention. It is also understood that while a patient may be started at one dose, that dose may be varied over time as the patient's condition changes.

The present invention provides compositions and methods for treating a cell proliferative disease or condition in an animal, comprising administering to an animal in need of such treatment a therapeutically effective amount of a histone deacetylase inhibitor of the invention. As noted, the animal can be a mammal, including a domesticated mammal. The animal can be a human.

The term "cell proliferative disease or condition" is meant to refer to any condition characterized by aberrant cell growth, preferably abnormally increased cellular proliferation. Examples of such cell proliferative diseases or conditions include, but are not limited to, cancer, restenosis, and psoriasis. In some embodiments, the invention provides a method for inhibiting neoplastic cell proliferation in an animal comprising administering to an animal having at least one neoplastic cell present in its body a therapeutically effective amount of a histone deacetylase inhibitor of the invention. Cancers treatable according to the invention include, but are not limited to, prostate cancer, lung cancer, acute leukemia, multiple myeloma, bladder carcinoma, renal carcinoma, breast carcinoma, colorectal carcinoma, neuroblastoma, or melanoma.

It is contemplated that some compounds of the invention have inhibitory activity against a histone deacetylase from a protozoal source. Thus, the invention also provides a method for treating or preventing a protozoal disease or infection, comprising administering to an animal in need of such treatment a therapeutically effective amount of a histone deacetylase inhibitor of the invention. Again, the animal can be a mammal, and can be a human. In some embodiments, the histone deacetylase inhibitor inhibits a protozoal histone deacetylase to a greater extent than it inhibits mammalian histone deacetylases, particularly human histone deacetylases.

The present invention further provides a method for treating a fungal disease or infection comprising administering to an animal in need of such treatment a therapeutically effective amount of a histone deacetylase inhibitor of the invention. The animal can be a mammal, including a human. The histone deacetylase inhibitor used according to this embodiment of the invention can inhibit fungal histone deacetylase to a greater extent than it inhibits mammalian histone deacetylases, particularly human histone deacetylases.

It should be apparent to one skilled in the art that the exact dosage and frequency of administration will depend on the particular compounds employed in the methods of the invention administered, the particular condition being treated, the severity of the condition being treated, the age, weight, general physical condition of the particular patient, and other medication the individual may be taking as is well known to administering physicians who are skilled in this art.

EXAMPLES

Experimental

Chemical reagents and organic solvents were purchased from Aldrich unless otherwise noted. Nuclear magnetic resonance spectra ($^1$H NMR) were measured on Bruker 250 MHz. Chemical shifts ($\delta$) are reported in parts per million (ppm) relative to TMS peak. Electrospray ionization (ESI) mass spectrometry analyses were performed with a 3-Tesla Finnigan FTMS-2000 Fourier Transform mass spectrometer. Elemental analyses were within ±0.4% of calculated values.

Flash column chromatography was performed with silica gel (230-400 mesh). The ω-amino acid methyl esters were prepared from the commercially available acids using methanol/TMSCl, and (2-amino-phenyl)carbamic acid benzyl ester was synthesized from o-phenylenediamine and benzyl chloride formate according to standard procedures. Rabbit anti-acetyl-Histone H3 and H4 polyclonal antibodies were purchased from Upstate Biotechnology (Lake Placid, N.Y.), Rabbit anti-p21 antibodies were from Santa Cruz Biotechnology (Santa Cruz, Calif.). Mouse monoclonal anti-actin was from ICN Biomedicals (Irvine, Calif.). HRP-conjugated goat anti-rabbit IgG and HRP-conjugated goat anti-mouse IgG were from Jackson ImmunoResearch (West Grove, Pa.).

Compounds 1-8 and 11-22 were synthesized according to methods a-e described as follows (Scheme 1A, FIG. 6), and compounds 9 and 10 were prepared from 3-[4-(2-propyl-pentanoylamino)-phenyl]-acrylic acid by methods f and g, respectively (Scheme 1B, FIG. 6), which are described separately under the title compounds.

Method a [1-(3-dimethylaminopropyl)-3-ethyl carbodiimide hydrochloride (EDC) coupling]. To a solution of individual short-chain fatty acids in dry THF (5-10 mmol/mL) under $N_2$ was added various ω-amino acid methyl ester (1 equiv.), followed by EDC (1.3 equiv.). After stirring overnight, THF was removed under reduced pressure, and the residue was dissolved in ethyl acetate (100 mL). The mixture was washed consecutively with water (50 mL) twice and saturated brine (50 mL). The organic layer was dried over $Na_2SO_4$, and concentrated under vacuum. The resulting residue was purified by silica gel flash chromatography.

Method b (ester cleavage). The resulting ester from Method a was dissolved in a 2M KOH/MeOH solution. The mixture was stirred at 80° C. for 1 h, cooled to 0° C., acidified with 2N HCl to pH 3, concentrated under vacuum, and ethyl acetate (100 mL) and $H_2O$ (50 mL) were added. The organic phase was separated, washed consecutively with water and saturated brine, 50 mL each, dried over $Na_2SO_4$, and concentrated under vacuum. The resulting residue was purified by silica gel flash chromatography.

Method c [bis(2-oxo-3-oxazolidinyl)phosphordiamidic chloride (BOP-Cl) coupling]. To a solution of the resulting acid from Method b in dry THF (5-10 mmol/mL) was added triethylamine (TEA, 1 equiv) under $N_2$. The mixture was stirred at room temperature for 10 min, and BOP-Cl (1.1 equiv), O-benzylhydroxylamine hydrochloride (1 equiv), and TEA (3 equiv) were added. After stirring at room temperature overnight, the solution was concentrated under vacuum, and ethyl acetate (100 mL) was added, followed by 3% $NaHCO_3$ (50 mL). The organic phase was separated, and washed consecutively with water and saturated brine, 50 mL each, dried over $Na_2SO_4$, and concentrated under vacuum. The resulting residue was purified by silica gel flash chromatography.

Method d (EDC coupling). To a solution of individual acids resulting from Method b in dry THF (5-10 mmol/mL) under N2 was added (2-aminophenyl)carbamic acid benzyl ester (1 equiv), followed by EDC (1.3 equiv). After stirring overnight, the mixture was concentrated under vacuum, and ethyl acetate (100 mL) was added. The organic phase was washed consecutively with water (50 mL) twice, followed by saturated brine (50 mL), dried over $Na_2SO_4$, and concentrated. The resulting residue was purified by silica gel flash chromatography.

Method e (hydrogenolysis). The N-benzyloxy or N-Cbz derivative, resulting from Method c or d, was dissolved in 1:1 methanol/THF (5-10 mmol/mL), and 10% palladium on charcoal (10% w/w) was added. The mixture was treated with hydrogen under atmospheric pressure for 2 h, and filtered. The solvent was evaporated and the residue was recrystallized with ethyl acetate.

N-(2-Amino-phenyl)-4-[(2-propyl-pentanoylamino)-methyl]-benzamide (1). $^1$H NMR (DMSO-$d_6$) $\delta$ 9.63 (s, 1 H), 8.45 (t, J=6.1 Hz, 1 H), 7.94 (d, J=7.8 Hz, 2 H), 7.36 (d, J=8.3 Hz, 2 H), 7.16 (d, J=7.6 Hz, 1 H), 6.98 (t, J=7.5 Hz, 1 H), 6.78 (d, J=7.7 Hz, 1 H), 6.60 (t, J=7.6 Hz, 1 H), 4.90 (s, 2 H), 4.35 (d, J=5.9 Hz, 2 H), 2.24 (m, 1 H), 1.6-1.1 (m, 8 H), 0.87 (t, 6 H); HRMS: exact mass of (M+Na)$^+$, 390.215195 amu; observed mass of (M+Na)$^+$, 390.21793 amu; anal. ($C_{22}H_{29}N_3O_2$) C, H, N.

N-Hydroxy-4-[(2-propyl-pentanoylamino)-methyl]-benzamide (2). $^1$H NMR (DMSO-$d_6$) $\delta$ 11.17 (s, 1 H), 9.00 (s, 1 H), 8.40 (t, J=5.9 Hz, 1 H), 7.70 (d, J=8.2 Hz, 2 H), 7.30 (d, J=8.2 Hz, 2 H), 4.31 (d, J=5.7 Hz, 2 H), 2.24 (m, 1 H), 1.6-1.1 (m, 8 H), 0.85 (t, 6 H); HRMS: exact mass of (M+Na)$^+$, 315.167911 amu; observed mass of (M+Na)⁺ 315.16755 amu; anal. ($C_{16}H_{24}N_2O_3$) C, H, N.

N-(2-Amino-phenyl)-4-(2-propyl-pentanoylamino)-benzamide (3). ¹H NMR (DMSO-$d_6$) δ 10.13 (s, 1 H), 9.57 (s, 1 H), 7.95 (d, J=8.7 Hz, 2 H), 7.74 (d, J=8.8 Hz, 2 H), 7.16 (d, J=7.8 Hz, 1 H), 6.98 (t, J=7.6 Hz, 1 H), 6.78 (d, J=8.0 Hz, 1 H), 6.60 (t, J=7.7 Hz, 1 H), 4.89 (s, 2 H), 2.44 (m, 1 H), 1.7-1.1 (m, 8 H), 0.89 (t, 6 H); HRMS: exact mass of (M+Na)⁺, 376.199545 amu; observed mass of (M+Na)⁺, 376.19762 amu; anal. ($C_{21}H_{27}N_3O_2$) C, H, N.

N-Hydroxy-4-(2-propyl-pentanoylamino)-benzamide (4). ¹H NMR (DMSO-$d_6$) δ 11.07 (s, 1 H), 10.13 (s, 1 H), 8.94 (s, 1 H), 7.65 (m, 4 H), 2.42 (m, 1 H), 1.7-1.1 (m, 8 H), 0.8 (t, 6 H); HRMS: exact mass of (M+Na)⁺, 301.152261 amu; observed mass of (M+Na)⁺, 301.15194 amu; anal. ($C_{15}H_{22}N_2O_3$) C, H, N.

2-Propyl-pentanoic acid {4-[(2-amino-phenylcarbamoyl)-methyl]-phenyl}-amide (5). ¹H NMR (DMSO-$d_6$) δ 9.84 (s, 1 H), 9.33 (s, 1 H), 7.56 (d, J=8.5 Hz, 2 H), 7.26 (d, J=8.5 Hz, 2 H), 7.14 (d, J=7.9 Hz, 1 H), 6.90 (t, J=7.8 Hz, 1 H), 6.72 (d, J=7.9 Hz, 1 H), 6.53 (t, J=7.7 Hz, 1 H), 4.83 (s, 2 H), 2.41 (m, 1 H), 1.7-1.1 (m, 8 H), 0.89 (t, 6 H); HRMS: exact mass of (M+Na)⁺ 390.215195 amu; observed mass of (M+Na)⁺, 390.21523 amu; anal. ($C_{22}H_{29}N_3O_2$) C, H, N.

2-Propyl-pentanoic acid (4-hydroxyphenylcarbamoylmethyl-phenyl)-amide (6). ¹H NMR (DMSO-$d_6$) δ 10.61 (s, 1 H), 9.82 (s, 1 H), 8.81 (s, 1 H), 7.52 (d, J=8.5 Hz, 2 H), 7.16 (d, J=8.5 Hz, 2 H), 3.22 (s, 2 H), 2.38 (m, 1 H), 1.7-1.1 (m, 8 H), 0.89 (t, 6 H); HRMS: exact mass of (M+Na)⁺, 315.167911 amu; observed mass of (M+Na)⁺, 315.16751 amu; anal. ($C_{16}H_{24}N_2O_3$) C, H, N.

2-Propyl-pentanoic acid {4-[2-(2-amino-phenylcarbamoyl)-ethyl]-phenyl}-amide (7). ¹H NMR (DMSO-$d_6$) δ 9.80 (s, 1 H), 9.15 (s, 1 H), 7.53 (d, J=8.4 Hz, 2 H), 7.17 (d, J=8.4 Hz, 2 H), 7.11 (d, J=7.8 Hz, 1 H), 6.89 (t, J=7.9 Hz, 1 H), 6.70 (d, J=7.9 Hz, 1 H), 6.53 (t, J=7.7 Hz, 1 H), 4.80 (s, 2 H), 2.86 (t, J=7.9 Hz, 2 H), 2.59 (t, J=8.1 Hz, 2 H), 2.38 (m, 1 H), 1.7-1.1 (m, 8 H), 0.87 (t, 6 H); HRMS: exact mass of (M+Na)⁺, 404.230845 amu; observed mass of (M+Na)⁺ 404.23043 amu; anal. ($C_{23}H_{31}N_3O_2$) C, H, N.

2-Propyl-pentanoic acid [4-(2-hydroxyphenylcarbamoyl)-ethyl)-phenyl]-amide (8). ¹H NMR (DMSO-$d_6$) δ 10.38 (s, 1 H), 9.78 (s, 1 H), 8.70 (s, 1 H), 7.50 (d, J=8.5 Hz, 2 H), 7.10 (d, J=8.5 Hz, 2 H), 2.75 (t, J=7.3 Hz, 2 H), 2.40 (m, 1H), 2.22 (t, J=7.4 Hz, 2 H), 1.7-1.1 (m, 8 H), 0.87 (t, 6 H); HRMS: exact mass of (M+Na)⁺, 329.183561 amu; observed mass of (M+Na)⁺ 329.18295 amu; anal. ($C_{17}H_{26}N_2O_3$) C, H, N.

3-[4-(2-propyl-pentanoyl)-phenyl]-acrylic acid. This compound, a precursor to compounds 9 and 10, was synthesized from 2-propyl-pentanoic acid (0.78 mL, 4.9 mmol) and 3-(4-amino-phenyl)-acrylic acid methyl ester (0.86 g, 4.9 mmol) according to Methods a and b aforementioned. Total yield, 1.05 g (70% for 2 steps); ¹H NMR (CDCl₃, 10% DMSO-$d_6$) δ 9.49 (s, 1 H), 7.71 (d, J=8.5 Hz, 2 H), 7.55 (d, J=15.9 Hz, 1 H), 7.45 (d, J=8.4 Hz, 2 H), 6.31 (d, J=15.9 Hz, 1 H), 2.40 (m, 1 H), 1.7-1.1 (m, 8 H), 0.87 (t, 6 H).

N-(2-Amino-phenyl)-3-[4-(2-propyl-pentanoylamino)-phenyl]-acrylamide (9). To a solution of 3-[4-(2-propyl-pentanoyl)-phenyl]-acrylic acid (200 mg, 0.7 mmol) in dry THF was added benzene-1,2-diamine (450 mg, 4.2 mmol) under N₂, followed by EDC (180 mg, 0.9 mmol). After stirring overnight, the mixture was concentrated under vacuum, ethyl acetate (50 mL) was added, and washed consecutively with water (30 mL) twice and saturated brine (30 mL). The organic layer was dried over Na₂SO₄, and concentrated under vacuum. The crude product was purified by flash chromatography (ethyl acetate-hexane, 1:1), giving compound 9 (200 mg, 76% yield) as white solid. ¹H NMR (DMSO-$d_6$) δ 10.07 (s, 1 H), 9.35 (s, 1 H), 7.71 (d, J=8.6 Hz, 2 H), 7.56 (d, J=8.5 Hz, 2 H), 7.51 (d, J=15.7 Hz, 1 H), 7.34 (d, J=6.6 Hz, 1 H), 6.92 (t, J=7.1 Hz, 1 H), 6.80 (d, J=15.5 Hz, 1 H), 6.75 (d, J=6.6 Hz, 1 H), 6.58 (t, J=7.3 Hz, 1 H), 4.96 (s, 2 H), 2.44 (m, 1 H), 1.7-1.1 (m, 8 H), 0.87 (t, 6 H); HRMS: exact mass of (M+Na)⁺, 402.215195 amu; observed mass of (M+Na)⁺, 402.21448 amu; anal. ($C_{23}H_{29}N_3O_2$) C, H, N.

N-Hydroxy-3-[4-(2-propyl-pentanoylamino)-phenyl]-acrylamide (10). To a solution of 3-[4-(2-propyl-pentanoylamino)-phenyl]-acrylic acid (100 mg, 0.35 mmol) in dry DMF (3 mL) was added EDC (79 mg, 0.53 mmol) and hydroxybenzotriazole hydrate (HOBT) (62 mg, 0.46 mmol) under nitrogen. The mixture was stirred for 1 h, hydroxylamine hydrochloride (27.4 mg, 0.39 mmol) and TEA (54 μL) were added, stirred for additional 12 h, concentrated under vacuum, and ethyl acetate (40 mL) and saturated NaHCO₃ solution (15 mL) were added. The organic phase was separated, and washed consecutively with water and saturated brine. 20 mL each. The organic layer was dried over Na₂SO₄, and concentrated under vacuum. The crude product was purified by flash chromatography [ethyl acetate-MeOH (9:1)], yielding compound 10 (45 mg, 40% yield) as white solid. ¹H NMR (DMSO-$d_6$) δ 10.69 (s, 1 H), 10.07 (s, 1 H), 9.00 (s, 1 H), 7.67 (d, J=7.9 Hz, 2 H), 7.53 (d, J=8.4 Hz, 2 H), 7.39 (d, J=15.6 Hz, 1 H), 6.39 (d, J=15.3 Hz, 1 H), 2.40 (m, 1 H), 1.7-1.1 (m, 8 H), 0.87 (t, 6 H); HRMS: exact mass of (M+Na)⁺, 327.167911 amu; observed mass of (M+Na)⁺, 327.16809 amu; anal. ($C_{17}H_{24}N_2O_3$) C, H, N.

N-(2-Amino-phenyl)-4-(butyrylamino-methyl)-benzamide (11). ¹H NMR (DMSO-$d_6$) δ 9.63 (s, 1 H), 8.41 (t, J=5.7 Hz, 1 H), 7.94 (d, J=8.1 Hz, 2 H), 7.36 (d, J=8.0 Hz, 2 H), 7.17 (d, J=7.6 Hz, 1 H), 6.98 (t, J=7.6 Hz, 1 H), 6.78 (d, J=8.1 Hz, 1H), 6.60 (t, J=7.7 Hz, 1 H), 4.90 (s, 2 H), 4.35 (d, J=5.8 Hz, 2 H), 2.15 (t, J=7.3 Hz, 2H), 1.60 (m, 2 H), 0.88 (t, J=7.3 Hz, 3 H); HRMS: exact mass of (M+Na)⁺, 334.152595 amu; observed mass of (M+Na)⁺, 334.15221 amu; anal. ($C_{18}H_{21}N_3O_2$) C, H, N.

N-(2-Amino-phenyl)-4-(phenylacetylamino-methyl)-benzamide (12). ¹H NMR (DMSO-$d_6$) δ 9.60 (s, 1 H), 8.66 (t, J=6.1 Hz, 1 H), 7.92 (d, J=8.2 Hz, 2 H), 7.31 (m, 7 H), 7.16 (d, J=7.0 Hz, 1 H), 6.98 (t, J=7.4 Hz, 1 H), 6.78 (d, J=6.6 Hz, 1 H), 6.60 (t, J=7.4 Hz, 1 H), 4.90 (s, 2 H), 4.35 (d, J=5.7 Hz, 2 H), 3.51 (s, 2 H); HRMS: exact mass of (M+Na)⁺, 382.152595 amu; observed mass of (M+Na)⁺, 382.15228 amu; anal. ($C_{22}H_{21}N_3O_2$) C, H, N.

N-(2-Amino-phenyl)-4-[(4-phenylbutyrylamino)-methyl]-benzamide (13). ¹H NMR (DMSO-$d_6$) δ 9.63 (s, 1 H), 8.43 (t, J=6.1 Hz, 1 H), 7.94 (d, J=8.3 Hz, 2H), 7.34 (d, J=8.3 Hz, 2 H), 7.21 (m, 6 H), 6.98 (t, J=7.2 Hz, 1 H), 6.78 (d, J=8.11 Hz, 2 H), 6.61 (t, J=6.5 Hz, 1 H), 4.90 (s, 2 H), 4.34 (d, J=6.1 Hz, 2 H), 2.59 (t, J=7.6 Hz, 2 H), 2.20 (t, J=7.7 Hz, 2 H), 1.84 (m, 2 H); HRMS: exact mass of (M+Na)⁺, 410.183895 amu; observed mass of (M+Na)⁺, 410.18232 amu; anal. ($C_{24}H_{25}N_3O_2$) C, H, N.

4-(Butyrylamino-methyl)-N-hydroxy-benzamide (14). ¹H NMR (DMSO-$d_6$) δ 11.15 (s, 1 H), 9.01 (s, 1 H), 8.36 (t, J=5.6 Hz, 1 H), 7.7 (d, J=8.1 Hz, 2 H), 7.32 (d, J=8.0 Hz, 2 H), 4.30 (d, J=5.7 Hz, 2 H), 2.15 (t, J=7.3 Hz, 2 H), 1.60 (m, 2 H), 0.88 (t, J=7.3 Hz, 3 H); HRMS: exact mass of (M+Na)⁺, 259.10569 amu; observed mass of (M+Na)⁺, 259.10569 amu; anal. ($C_{12}H_{16}N_2O_3$) C, H, N.

N-Hydroxy-4-(phenylacetylamino-methyl)-benzamide (15). ¹H NMR (DMSO-$d_6$) δ 11.2 (s, 1 H), 8.9 (s, 1 H), 8.6 (t, J=5.8 Hz, 1 H), 7.9 (d, J=8.3 Hz, 2 H), 7.28 (m, 7 H), 4.04 (d, J=5.7 Hz, 2 H), 3.5 (s, 2 H); HRMS: exact mass of (M+Na)⁺, 307.105311 amu; observed mass of (M+Na)+, 307.10512 amu; anal. ($C_{16}H_{16}N_2O_3$) C, H, N.

N-Hydroxy-4-[(4-phenylbutyrylamino)-methyl]-benzamide (16). $^1$H NMR (DMSO-$d_6$) δ 11.2 (s, 1 H), 9.0 (s, 1 H), 8.4 (t, J=5.8 Hz, 1 H), 7.7 (d, J=8.0 Hz, 2 H), 7.21 (m, 7 H), 4.3 (d, J=5.8 Hz, 2 H), 2.58 (t, J=7.3 Hz, 2 H), 2.18 (t, J=7.3 Hz, 2 H), 1.83 (m, 2 H); HRMS: exact mass of (M+Na)+, 335.136611 amu; observed mass of (M+Na)+, 335.13716 amu; anal. ($C_{18}H_{20}N_2O_3$) C, H, N.

4-Butyrylamino-N-hydroxy-benzamide (17). $^1$H NMR (DMSO-$d_6$) δ 11.08 (s, 1 H), 10.09 (s, 1 H), 8.94 (s, 1 H), 7.67 (m, 4 H), 2.31 (t, J=7.3 Hz, 2 H), 1.61 (m, 2 H), 0.92 (t, J=7.4 Hz, 3 H); HRMS: exact mass of (M+Na)+ 245.089661 amu, Observed Mass of (M+Na)+ 245.08971 amu, Difference <1.0 ppm. Anal. ($C_{11}H_{14}N_2O_3$) C, H, N.

N-Hydroxy-4-phenylacetylamino-benzamide (18). $^1$H NMR (DMSO-$d_6$) δ 11.1 (s, 1 H), 10.40 (s, 1 H), 8.94 (s, 1 H), 7.67 (m, 4 H), 7.33 (m, 5 H), 3.67 (s, 2 H); HRMS: exact mass of (M+Na)+, 293.089661 amu; observed mass of (M+Na)+, 293.08957 amu; anal. ($C_{15}H_{14}N_2O_3$) C, H, N.

N-Hydroxy-4-(4-phenylbutyrylamino)-benzamide (19). $^1$H NMR (DMSO-$d_6$) δ 11.02 (s, 1 H), 10.1 (s, 1 H), 8.94 (s, 1 H), 7.67 (m, 4 H), 7.27 (m, 5 H), 2.63 (t, J=7.5 Hz, 2 H), 2.35 (t, J=7.4 Hz, 2 H), 1.87 (m, 2 H); HRMS: exact mass of (M+Na)+, 321.120961 amu; observed mass of (M+Na)+, 321.11940 amu; anal. ($C_{17}H_{15}N_2O_3$) C, H, N.

N-[4-(2-Hydroxycarbamoyl-ethyl)-phenyl]-butyramide (20). $^1$H NMR (DMSO-$d_6$) δ10.4 (s, 1 H), 9.8 (s, 1 H), 8.70 (s, 1 H), 7.50 (d, J=8.4 Hz, 2 H), 7.10 (d, J=8.4 Hz, 2 H), 2.75 (t, J=7.3 Hz, 2 H), 2.24 (m, 4 H), 1.61 (m, 2 H), 0.92 (t, J=7.4 Hz, 3 H); HRMS: exact mass of (M+Na)+, 273.120961 amu; observed mass of (M+Na)+, 273.12080 amu; anal. ($C_{13}H_{18}N_2O_3$) C, H, N.

N-Hydroxy-3-(4-phenylacetylamino-phenyl)-propionamide (21). $^1$H NMR (DMSO-$d_6$) δ 10.36 (s, 1 H), 10.14 (s, 1 H), 8.70 (s, 1 H), 7.50 (d, J=8.3 Hz, 2 H), 7.2-7.4 (m, 5 H), 7.10 (d, J=8.3 Hz, 2 H), 3.62 (s, 2 H), 2.75 (t, J=7.5 Hz, 2 H), 2.22 (t, J=7.6 Hz, 2 H); HRMS: exact mass of (M+Na)+ 321.120961 amu; observed mass of (M+Na)+, 321.12040 amu; anal. ($C_{17}H_{18}N_2O_3$) C, H, N.

N-[4-(2-Hydroxycarbamoyl-ethyl)-phenyl]-4-phenyl-butyramide (22). $^1$H NMR (DMSO-$d_6$) δ 10.36 (s, 1 H), 9.80 (s, 1 H), 8.70 (s, 1 H), 7.52 (d, J=8.5 Hz, 2H), 7.2-7.4 (m, 5 H), 7.10 (d, J=8.4 Hz, 2 H), 2.75 (t, J=7.4 Hz, 2 H), 2.62 (t, J=7.5 Hz, 2 H), 2.15-2.4 (m, 4 H), 1.8-2.0 (m, 2 H); HRMS: exact mass of (M+Na)+, 349.152261 amu; observed mass of (M+Na)+, 349.15223 amu; anal. ($C_{19}H_{22}N_2O_3$) C, H, N.

A list of all compounds, including additional compounds 23-67, is shown in FIG. 6.

In vitro HDAC assay. HDAC activity was analyzed by using a histone deacetylase assay kit (Upstate Biotechnology, Lake Placid, N.Y.) by following the manufacturer's instruction with slight modifications. This assay was based on the ability of DU-145 nuclear extract, which is rich in histone deacetylase activity, to mediate the deacetylation of biotinylated [3H]-acetyl histone H4 peptide that was bound to streptavidin agarose beads. The release of [3H]-acetate into the supernatant was measured to calculate the HDAC activity. Sodium butyrate (0.25-1 mM) was used as a positive control.

Cell viability assay. The effect of HTPB on cell viability was assessed by the MTT {[3-(4,5-dimethylthiazol-2-yl)-2,5-diphenyl-2 H-tetrazolium bromide]} assay in 96-well, flat-bottomed plates, in which 4,000 DU-145 cells/well were seeded. Cells were exposed to HTPB at the indicated concentrations in 10% FBS-supplemented RPMI-1640 medium at 37° C. in 5% $CO_2$ for the indicated time. The medium was removed and replaced by 150 μl of 0.5 mg/ml of MTT in RPMI-1640 medium, and cells were incubated in the $CO_2$ incubator at 37° C. for 2 hours. Supernatants were removed from the wells, and the reduced MTT dye was solubilized with 200 μl/well DMSO. Absorbance was determined on a plate reader at 570 nm. Each treatment was repeated in six wells.

Apoptosis Detection by An Enzyme-Linked Immunosorbent Assay (ELISA). Induction of apoptosis was assessed by using a Cell Death ELISA (Roche Diagnostics, Mannheim, Germany) by following the manufacturer's instruction. This test is based on the quantitative determination of cytoplasmic histone-associated DNA fragments in the form of mononucleosomes and oligonucleosomes after induced apoptotic death. In brief, 1×10$^6$ DU-145 cells were cultured in a T-75 flask 24 h prior to the experiment. Cells were treated with HTPB at the indicated concentrations in 10% FBS-supplemented RPMI 1640 medium. Both floating and adherent cells were collected, cell lysates equivalent to 2×10$^3$ cells were used in the ELISA.

Western blot analysis. DU-145 cells (1×10$^6$) treated with HTPB at the indicated concentrations in 10% FBS-supplemented RPMI 1640 medium for 24 h were collected, and sonicated. Protein concentrations of the lysates were determined by using a Bradford protein assay kit (Bio-Rad, Hercules, Calif.); equivalent amounts of proteins from each lysate were resolved in 10% SDS-polyacrylamide gel, and then transferred onto Immobilon-nitrocellulose membranes (Millipore, Bellerica, Mass.) in a semi-dry transfer cell. The transblotted membrane was washed twice with Tris-buffered saline (TBS) containing 0.1% Tween 20 (TBST). After blocking with TBST containing 5% nonfat milk for 40 min, the membrane was incubated with the primary antibody (1:1000 dilution) in TBST-1% nonfat milk at 4° C. overnight. After treatment with the primary antibody, the membrane was washed three times with TBST for a total of 15 min, followed by goat anti-rabbit or anti-mouse IgG-horseradish peroxidase conjugates (diluted 1:3000) for 1 h at room temperature and wash three times with TBST for a total of 1 h. The immunoblots were visualized by enhanced chemiluminescence.

Results

For the first series of compounds, we employed valproic acid as lead to synthesize $Zn^{2+}$-tethered conjugates (FIG. 1) according to the procedures depicted in Scheme 1 (A, compounds 1-8; B, compounds 9 and 10). For compounds 1-8, valproic acid was coupled with four different ω-amino acid methyl ester spacers via EDC activation. The resulting esters were cleaved to acids via alkaline hydrolysis. Under typical peptide coupling conditions (BOPCl or EDC), the resulting acids were treated with Bn-protected hydroxylamine and Cbz-protected o-phenylenediamine to form, after hydrogenolysis, the respective anilides and hydroxamic acids (Scheme 1A). Compound 9 and 10 were synthesized by direct coupling of 3-[4-(2-propyl-pentanoyl)-phenyl]-acrylic acid with o-phenylenediamine and hydroxylamine, respectively, under typical EDC coupling condition (Scheme 1B).

Figure 2:
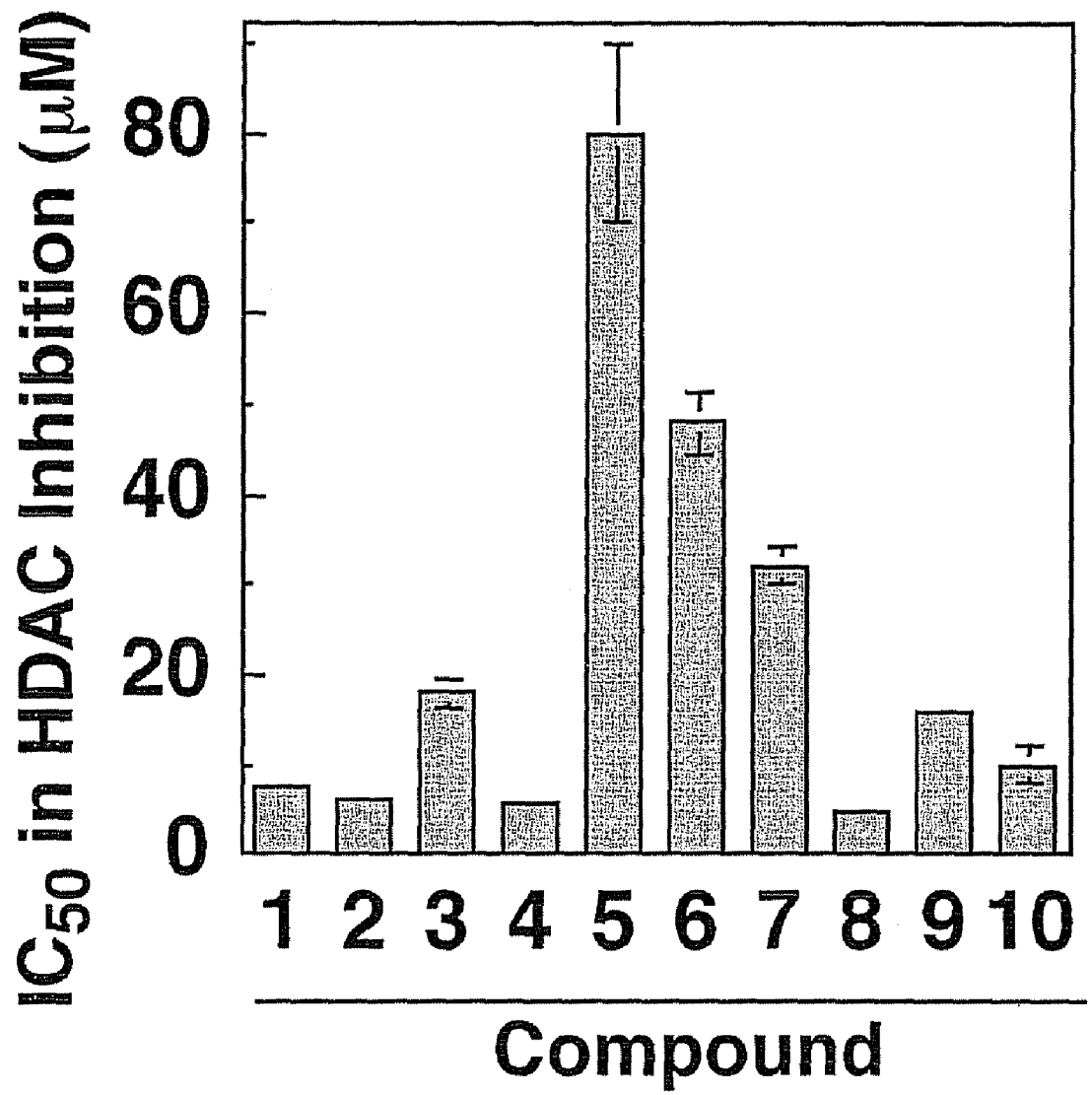
FIG. 2 shows HDAC inhibitory potency of compounds 1-10. In vitro HDAC assay was carried out by using a commercial enzyme assay kit as described herein. Data are the means±S.D. (n=3).

$Zn^{2+}$-chelating motif-tethered valproate derivatives. The divergent conjugation of valproic acid with five different aromatic linkers and subsequently two $Zn^{2+}$-binding motifs yielded compounds 1-10. These tethered conjugates displayed varying degree of HDAC inhibitory potency (FIG. 2), with $IC_{50}$ values ranging from 5 μM (compound 8) to 80 μM (compound 5). This potency was an eighty- to five-fold improvement over that of the parent molecule ($IC_{50}$, 0.4 mM). Removal of the valproyl moiety or the $Zn^{2+}$-chelating motif from any of these conjugates completely abolished the HDAC inhibitory activity (data not shown), indicating the importance of the acyl function and the $Zn^{2+}$-chelating motif in the protein-ligand interactions.

Among the ten tethered conjugates examined, compounds 1, 2, 4, and 8 represented the optimal derivatives ($IC_{50}$, 5-8 μM), followed by 3, 9, and 10 ($IC_{50}$, 10-20 μM). Relatively, the hydroxamates (compounds 2, 4, 6, 8, and 10) were generally more potent than their phenylenediamine counterparts (compounds 1, 3, 5, 7, and 9). Moreover, the aromatic linker exhibited a subtle effect on HDAC inhibitory activity. Among the five aromatic o-amino acids examined, (4-aminophenyl) acetate gave rise to conjugates with the least HDAC inhibitory potency (5 and 6), while 4-(aminomethyl)benzoate appeared to be optimal. For further structural modifications, compounds 1, 2, 4, and 8 were used as leads since all of them exhibited $IC_{50}$<10 μM.

Structural modification. The finding that removal of the valproyl group completely abrogated the inhibitory activity of the conjugate underscored the importance of the acyl moiety in interacting with the active-site pocket. We thus substituted the valproyl group in compounds 1, 2, 4, and 8 with a butyryl, phenylacetyl, or phenylbutyryl to enhance the stereoelectronic effect on HDAC inhibition (FIG. 3). All these derivatives showed an improved potency in HDAC inhibition as compared to the valproyl counterparts. Among various acyl functions examined, the relative potency was in the order of phenylbutyryl>phenylacetyl>butyryl>valproyl when conjugated to the same spacer and $Zn^{2+}$-chelating motif.

Of these twelve derivatives, compound 19 was especially noteworthy. This hydroxamate-tethered phenylbutyrate (HTPB), i.e., compound 19, exhibited $IC_{50}$ of 44 nM, a four-order-of-magnitude improvement over phenylbutyrate. This compound was used to examine its effect on HDAC activity in DU-145 prostate cancer cells.

Effect of HTPB on histone acetylation and $p21^{WAF/CIP1}$ expression in DU-145 prostate cancer cells. Histone hyperacetylation and increased expression of the cyclin-dependent kinase inhibitor $p21^{WAF/CIP1}$ represent two hallmark features in association with intracellular HDAC inhibition (Marks et al., Nat Rev Cancer 1: 194-202 (2001)). Consequently, we examined the effect of HTPB vis-à-vis TSA and phenylbutyrate on HDAC activity in DU-145 prostate cancer cells by characterizing the status of histone acetylation and $p21^{WAF/CIP1}$ expression.

Figure 4:
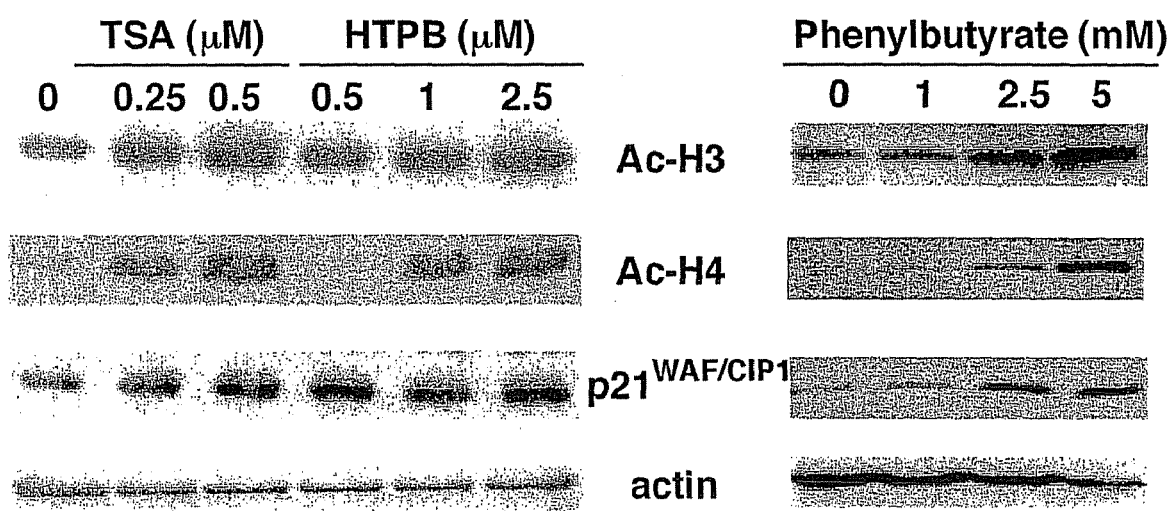
FIG. 4 shows the effect of HTPB, TSA, and phenylbutyrate on histone acetylation and $p21^{WAF/CIP1}$ expression in DU-145 cells. DU-145 cells were exposed to HTPB, TSA, and phenylbutyrate at the indicated concentrations in 10% FBS-supplemented RPMI 1640 medium for 24 h. An equivalent amount of protein from individual lysates was electrophoresed and probed by Western blot with respective antibodies. Actin was used as an internal reference protein.

DU-145 cells were exposed to HTPB at 0.5, 1, 2.5 μM, TSA at 0.25 and 0.5 μM, or phenylbutyrate at 1, 2.5, and 5 mM in 10% FBS-supplemented RPMI 1640 medium for 24 h. Western blot analysis of the cell lysates indicates that treatment of these agents gave rise to elevated levels of acetylated histones H3 and H4, and $p21^{WAF/CIP1}$ (FIG. 4). The effect of 1 μM HTPB on these biomarkers approximated that of 0.25 μM TSA, or 2.5 mM phenylbutyrate. DU-145 cells displayed small but significant amounts of intrinsic $p21^{WAF/CIP1}$, and the level increased substantially after exposure to HTPB as low as 0.5 μM. Together, these data confirmed that HTPB targeted HDAC activity in DU-145 cells.

Figure 5:
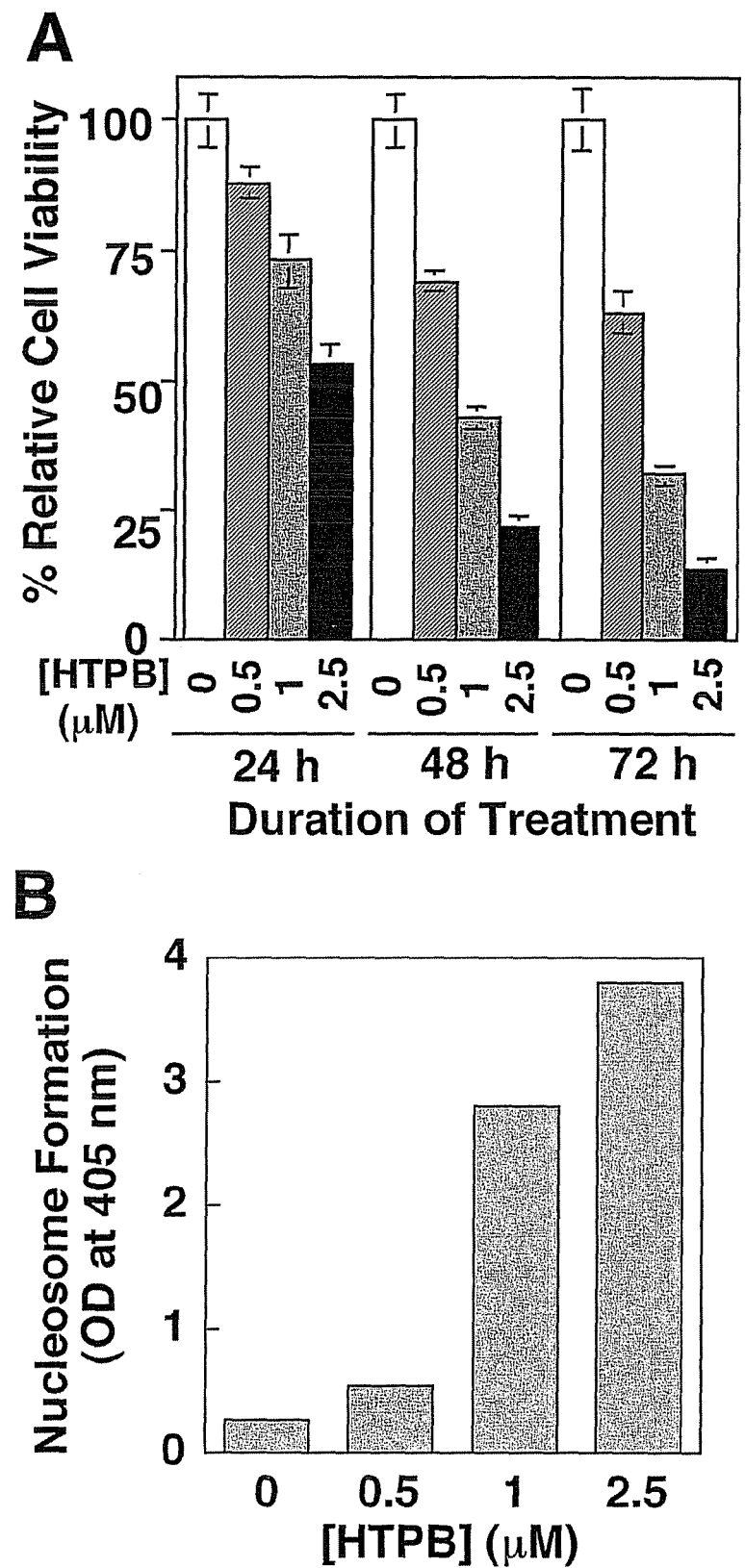
FIG. 5 shows the growth inhibitory effect of HTPB on DU-145 cells. (A) Time course of the dose-dependent effect of HTPB on cell viability. DU-145 cells were treated with 0-2.5 µM HTPB in 10% FBS-containing RPMI 1640 medium for the indicated times. Viable cells were examined by the MTT assay. Data are means±S.D. (n=6). (B) Dose-dependent effect of HTPB on the formation of nucleosomal DNA after 24-hr exposure. The formation of nucleosomes was quantitatively measured by Cell Death Detection ELISA with lysates equivalent to $2 \times 10^3$ cells for each assay. Data are the average of two independent determinations.

Effect of HTPB on DU-145 cell viability. Effect of HTPB on cancer cell viability was assessed in DU-145 cells in 10% FBS-supplemented RPMI-1640 medium. These cells displayed high degree of sensitivity to HTPB, with $IC_{50}$ in growth inhibition of approximately between 0.5 and 1 μM (FIG. 5A). As evidenced by DNA fragmentation, HTPB sensitized DU-145 cells to apoptosis in a dose-dependent manner (FIG. 5B). As shown, extensive apoptosis occurred at 24 h when the drug concentration exceeded 1 μM, indicating that this cytotoxic effect was, at least in part, attributable to the induction of apoptosis by HDAC inhibition. Other cell lines examined including AN3CA endometrial cancer cells, and SW-48 and HCT-15 colorectal cancer cells. These cancer cells were also susceptible to the cytotoxic effect of HTPB with similar potency (data not shown).

Discussion

Herein, we present the development of a novel class of HDAC inhibitors, in which short-chain fatty acids were tethered to a $Zn^{2+}$-chelating moiety through hydrophobic linkage. Our strategy in the development of these compounds was built on a working model provided by the unique mode of HDAC inhibition by TSA and SAHA (Finnin et al., Nature 401: 188-193 (1999)). Our novel tethering strategy led to the discovery of HTPB (or compound 19), which displays HDAC inhibitory and antiproliferative activities at sub-μm concentrations that are in line with that reported for SAHA (Richon et al., Proc Natl Acad Sci USA 95: 3003-3007 (1998)).

We obtained two lines of evidence that HTPB targeted HDAC activity in several cancer cell lines. Specifically, treatment of DU-145 prostate cancer cells with HTPB at as low as 0.5 μM caused the hyperacetylation of histones H-3 and H-4 in a dose-dependent manner. Likewise, $p21^{WAF/CIP1}$ expression was substantially upregulated in response to HTPB. In contrast, the parent molecule phenylbutyrate required at least 2.5 mM to achieve the same intracellular effects on histone acetylation and $p21^{WAF/CIP1}$ expression.

HTPB is structurally distinct from existing HDAC inhibitors, in many of which the cap groups consist of polar, planar structures. For example, the cap groups of TSA, SAHA, and MS-275 contain dimethylaminophenyl, phenylamino, and pyridin-3-yl-methoxycarbonyl groups, respectively. Thus, we have further concluded that the active-site pocket exhibits a high degree of flexibility in accommodating cap groups with different stereoelectronic properties. Our data indicate that phenylbutyryl and phenylacetyl were more effective than aliphatic acyl moieties in facilitating the binding of the conjugates to the active-site pocket. This discrepancy might, in part, be due to differences in electron density and/or steric hindrance imposed by the branched side chain. With regard to the aromatic linker, 4-aminobenzoate appeared to be optimal to tether phenylbutyryl with hydroxamate, of which the length was sufficient to make contacts at both ends of the pocket.

Design and synthesis of the generation HDAC inhibitors—Structure-based optimization of Compound 19. Compound 19 (HTPB) is structurally distinct from existing HDAC inhibitors, many of which have cap groups consisting of polar, planar structures, e.g., TSA, dimethylaminophenyl; SAHA, phenylamino; and MS-27-275, pyridin-3-yl-methoxycarbonyl. This finding suggests that the HDAC active-site pocket exhibits a high degree of flexibility in accommodating cap groups with different stereo-electronic properties.

Figure 9:
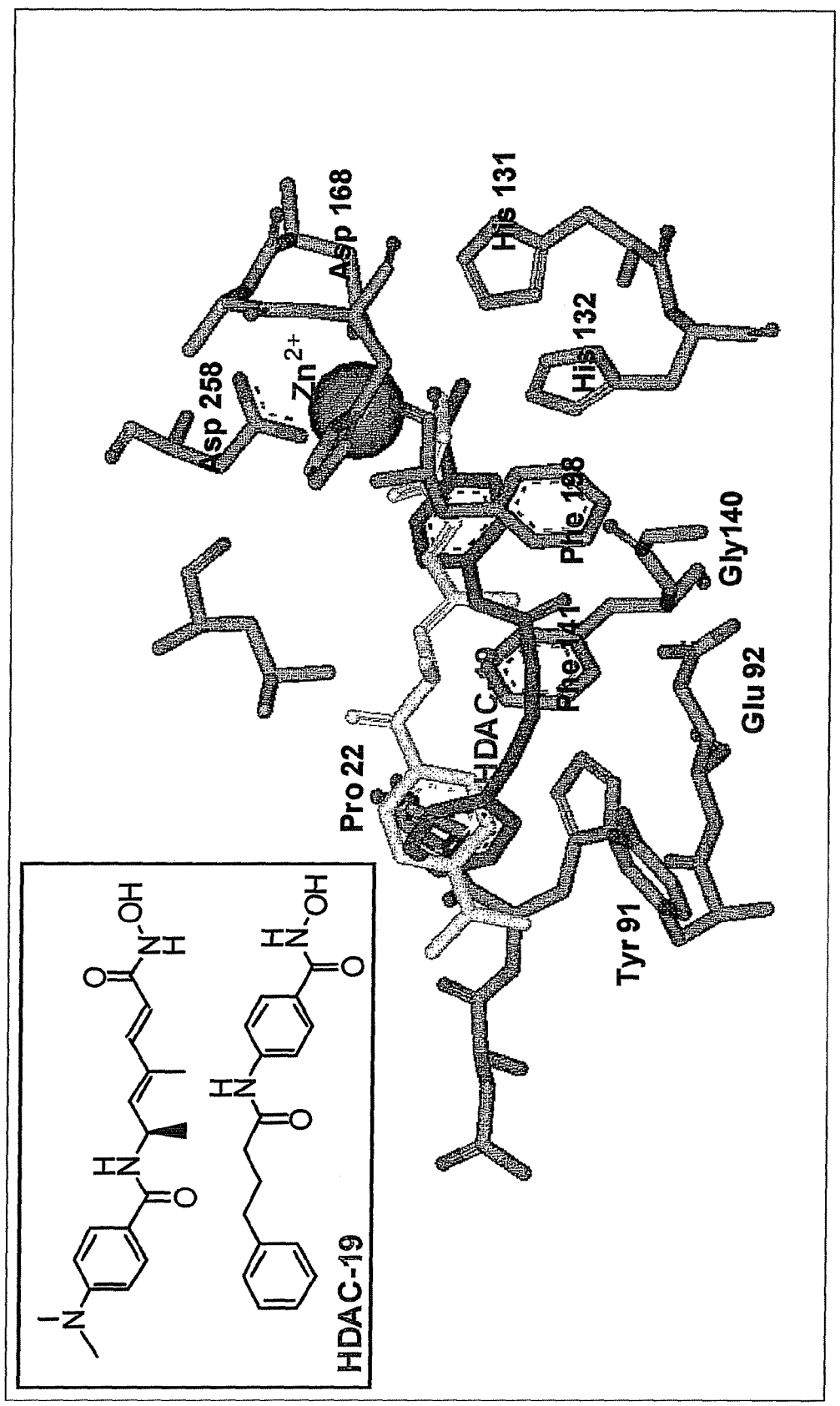
FIG. 9 is a molecular modeling study of the ligand docking of compound 19.

To envisage the ligand binding, we carried out molecular docking of compound 19 (FIG. 9, in red) and TSA (FIG. 9, in yellow) into the active-site pocket of HDLP following energy minimization to compare the mode of recognition of individual ligands. As shown in FIG. 9, both ligands adopt similar configurations in binding to the pocket. The aromatic linker of compound 19, 4-aminobenzoate, provides an optimal length to tether phenylbutyryl with hydroxamate, allowing both functions to make contacts at both ends of the pocket. It appears that the hydroxamic acid function [C(O)NH—OH] attributes to the four-orders-of-magnitude increase in the HDAC inhibitory potency of compound 19 over phenylbutyrate.

Figure 10:
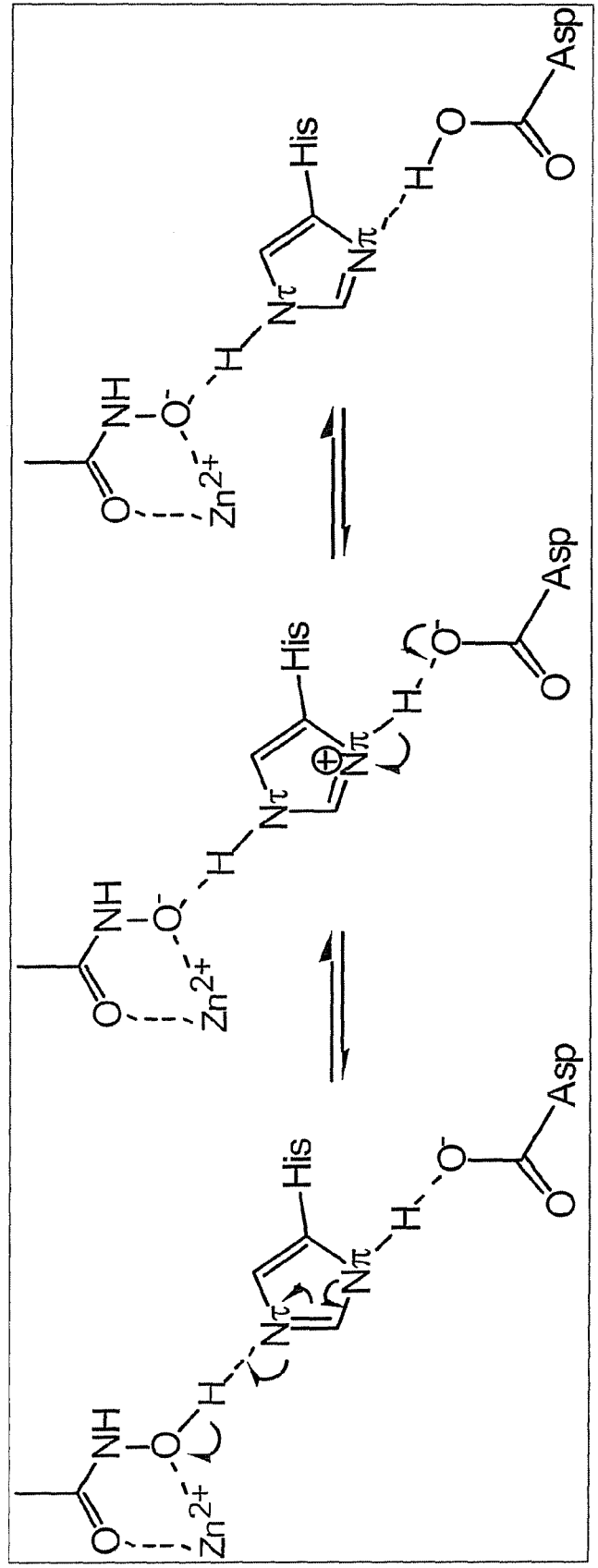
FIG. 10 diagrammatically illustrates the proton transfer that is believed to occur during the interaction of compound 19 and its binding site.

The modeling data in FIG. 9 suggest that the role of the hydroxamate in ligand binding is twofold. First, it chelates the Zn2+ cation. Second, it facilitates proton transfer from NH—OH to Nτ of His-131 with the aid of the His131-Asp173 charge relay system (FIG. 10). (See Vanommeslaeghe, K., Van Alsenoy, C., De Proft, F., Martins, J. C., Tourwe, D., and Geerlings, P. Ab initio study of the binding of Trichostatin A (TSA) in the active site of histone deacetylase like protein (HDLP). Org Biomol Chem, 1: 2951-2957, 2003, for ligand binding studies of TSA.)

As a consequence, binding of hydroxamate HDAC inhibitors, either TSA or compound 19, give rise to a transfer of negative charge from Asp to hydroxamate, resulting in a salt bridge formation between the negatively charged hydroxamate and the positive charges on $Zn^{2+}$ and the imidazole ring (central panel, FIG. 10). Mechanistically, this salt bridge represents a major force contributing to the binding of hydroxamate-based ligands to the active site pocket, and underlies the differential free energy change ($\Delta\Delta G^{\ddagger}=-5.4$ kcal/mol) required for the $10^4$-fold increase in HDAC inhibitory potency in association with the conversion of phenylbutyrate to compound 19 ($IC_{50}$, 0.4 mM versus 44 nM).

The role of this salt bridge in binding affinity is further underscored by a 10-fold drop in HDAC inhibitory potency when the hydroxamate moiety of compound 19 was replaced by a phenylenediamine function (compound 55), i.e., $IC_{50}$, 0.044 versus 0.4 µM. In contrast to hydroxamate, binding of the phenylenediamine group to the active site does not involve a proton transfer to Nτ of $His^{131}$. Instead, the electron-rich diamine only chelates with the $Zn^{2+}$ cation without forming charge-charge interactions with $His^{131}$. Consequently, the binding affinity with a phenylenediamine-based ligand, e.g., compound 55, is significantly diminished as compared to the hydroxamate counterpart.

This molecular docking also provided useful guidance for the subsequent modification of compound 19. As shown in FIG. 9, the cap groups of TSA and compound 19 are located near a groove surrounded by $Tyr^{91}$, $Glu^{92}$, $Gly^{140}$, and $Phe^{141}$. In principle, this groove could provide flexibility in accommodating cap groups with varying degrees of bulkiness, and could thus be exploited to enhance HDAC inhibitory potency.

Accordingly, we replaced the phenylbutyryl moiety of compound 19 with various α-branched aromatic fatty acyl groups, of which the rationale was twofold. First, the amide linkage between the phenylbutyryl group and the linker in compound 19 might be susceptible to proteolytic digestion. Increasing the bulkiness of the acyl function might enhance the metabolic stability by rendering the amide linkage more sterically hindered. Second, increase in the size of the acyl function might increase the hydrophobic bonding with the aforementioned groove, thereby enhancing the binding affinity.

This strategy led to a number of HDAC inhibitors with greater potency than compound 19 (i.e., HTPB). The structures and $IC_{50}$ values of some of the representative derivatives are summarized in Table 1.

TABLE 1

Representative phenylbutyrate-based HDAC inhibitors

| Designation | R | $IC_{50}$ (nM) |
| --- | --- | --- |
| 19 | (phenylbutyryl) | 44 |
| 42 | (α-isopropyl phenylacetyl) | 25 |
| 44 | (α,α-dimethyl phenylpropanoyl) | 32 |
| 61 | (α-ethyl phenylacetyl) | 38 |

Figure 11:
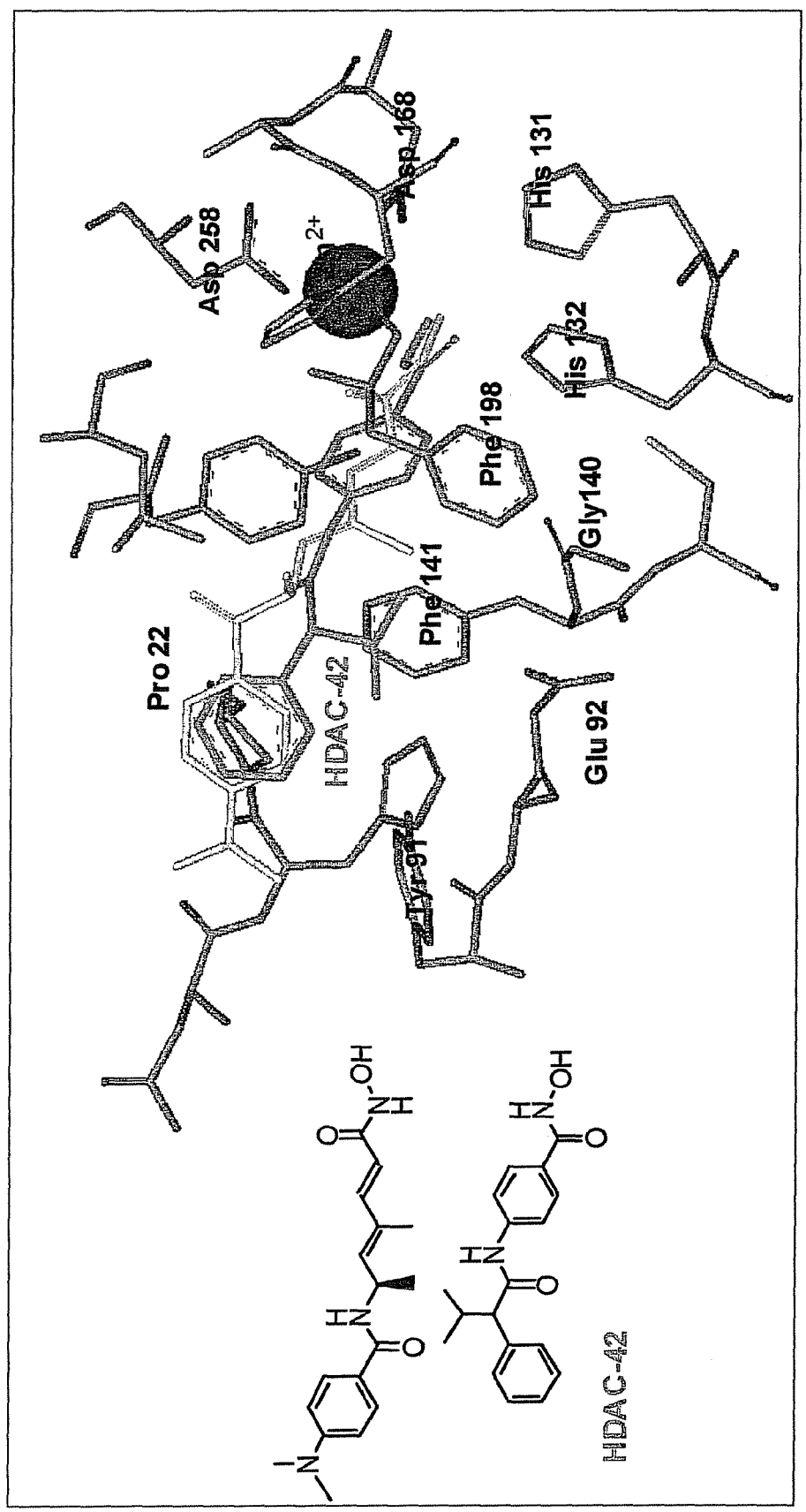
FIG. 11 is a molecular modeling study of the ligand docking of compound 42.

Among more than 80 derivatives that were synthesized, compound 42 represents the optimal agent with $IC_{50}$ comparable to that of TSA. Molecular modeling analysis indicates that compound 42 assumed a configuration that juxtaposed with that of TSA inside the active-site pocket. (See FIG. 11.) In addition, the isopropyl moiety resided inside the groove, and might interact with the nearby hydrophobic residues. Therefore, compound 42 was selected for further in vitro and in vivo characterizations.

Figure 12:
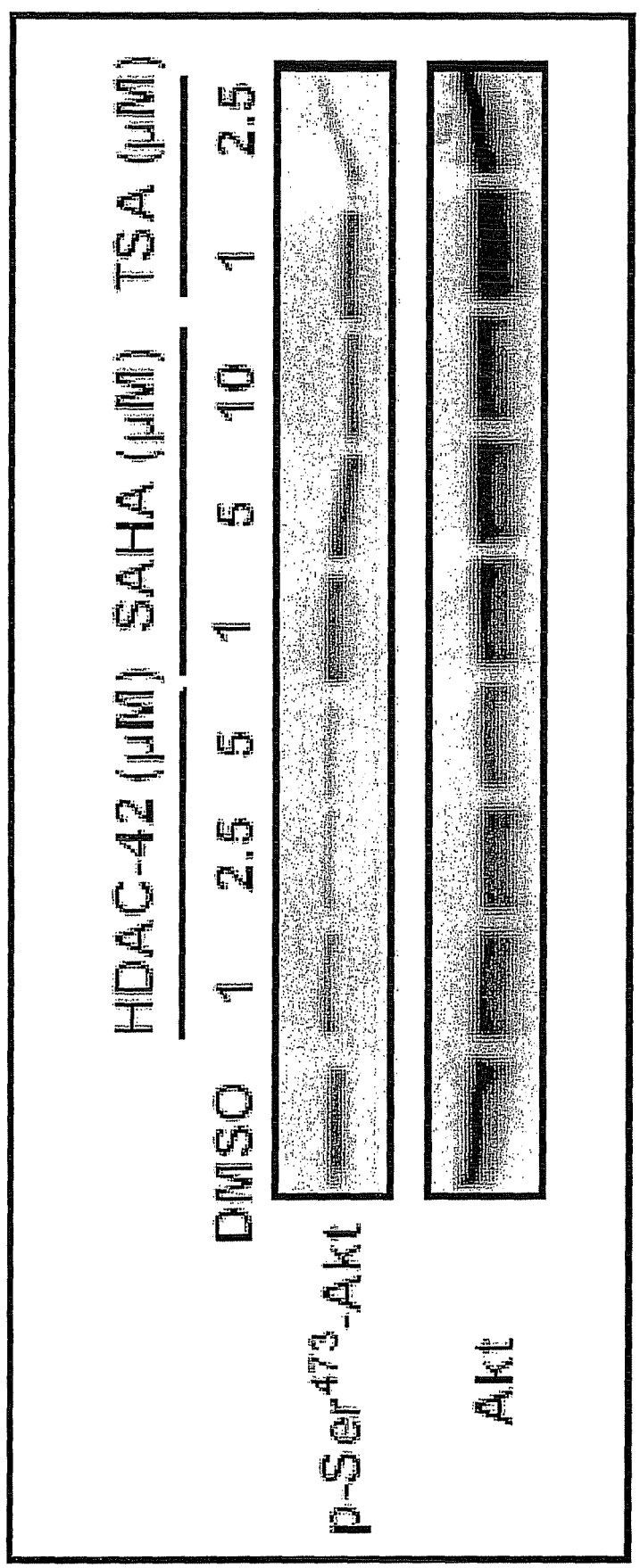
FIG. 12 shows the effect of compound 42, SAHA, and TSA on histone H-4 hyperacetylation and $p21^{WAF/CIP1}$ expression in PC-3 androgen-independent prostate cancer cells.

Compound 42 and TSA mediate antiproliferative effects at both epigenetic and cellular levels—Identification of novel cellular targets. Compound 42, SAHA, and TSA were subject to examinations of their effects on $p21^{WAF/CIP1}$ expression and histone H-4 hyperacetylation in PC-3 androgen-independent prostate cancer cells. FIG. 12 demonstrates that the potency of compound 42 in the induction of these biomarkers is comparable to that of TSA, and is about fivefold higher than that of SAHA.

Figure 13:
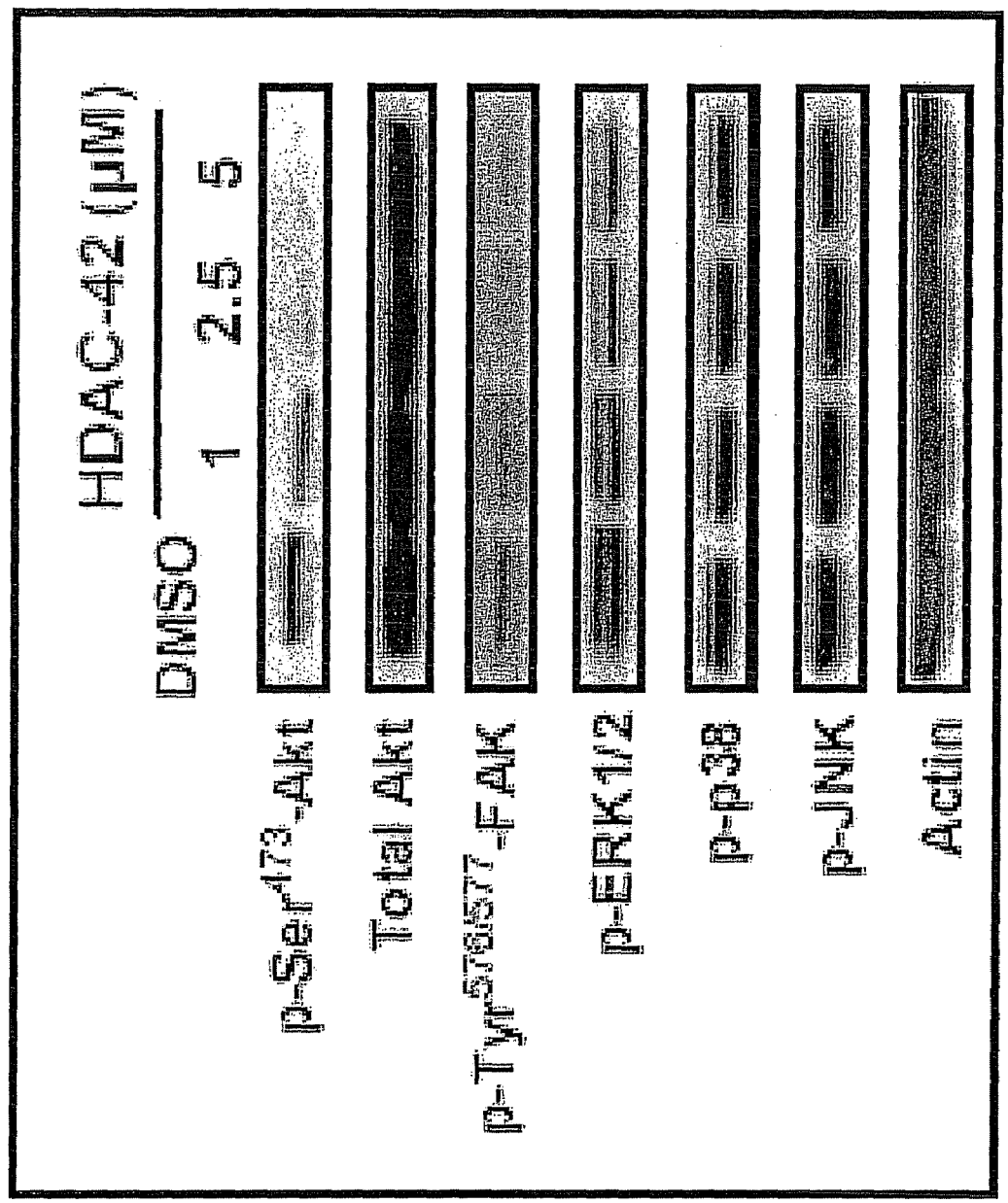
FIG. 13 shows the effect of compound 42, SAHA, and TSA on the activation status of Akt in PC-3 cells.

The effect of these agents on the activation status of Akt in PC-3 cells ($PTEN^{-/-}$) was also examined. Akt is constitutively activated in PC-3 cells due to lack of functional PTEN, which contributes to the androgen independency and chemotherapeutic resistance of these cells. It is noteworthy that both compound 42 and TSA caused significant Akt dephosphorylation at as low as 1 µM in PC-3 cells (FIG. 13). In contrast, no appreciable effect of SAHA on phospho-Akt was noted at comparable concentrations, suggesting subtle differences in the mode of action between SAHA and compound 42/TSA.

Figure 14:
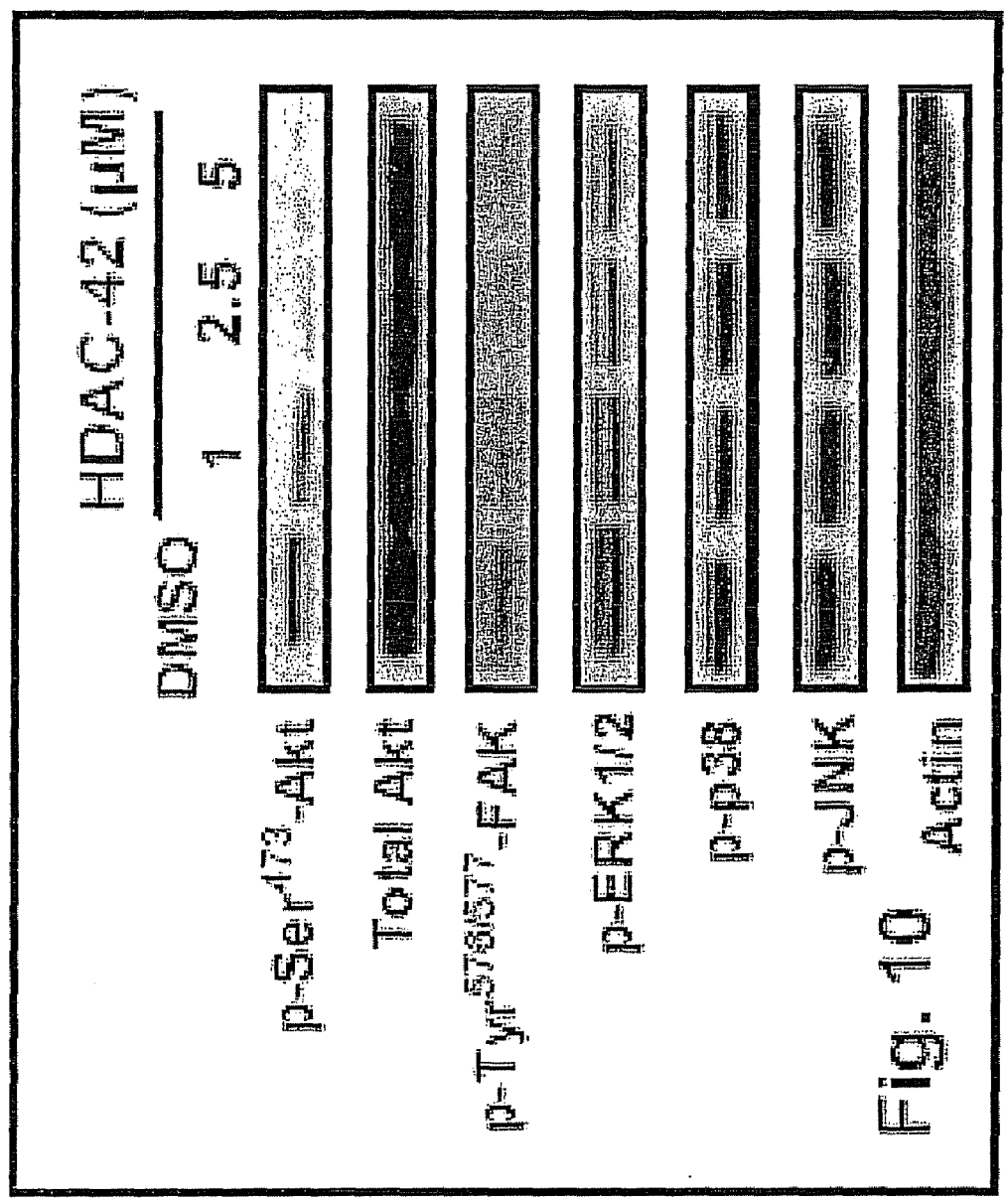
FIG. 14 shows the effect of compound 42 on several kinases.

The effect of compound 42 on phospho-Akt in PC-3 cells is noteworthy in light of the clinical application of this HDAC inhibitor in hormone-refractory prostate cancer cells, most of which exhibit PTEN mutations. This dephosphorylating effect, however, is kinase-specific. Among a series of other signaling kinases examined, the phosphorylation level of FAK (focal adhesion kinase) and ERKs was diminished in a dose-dependent manner, while that of p38 or JNK remained unaffected (FIG. 14).

We hypothesize that this dephosphorylation is mediated through protein phosphatase 1 (PP1) which has been reported to form complexes with HDAC isozymes to facilitate its nuclear localization. We propose that treatment of PC-3 cells with compound 42 or TSA results in the disruption of HDAC-PP1 complexes in the nucleus, which leads to the re-localization of PP1 into the cytoplasm to mediate the dephosphorylation of target kinases. Alternatively, this effect could be due to the acetylation of heat shock protein (HSP)-90, which results in diminished binding to Akt and its subsequent degradation (Fuino, L., Bali, P., Wittmann, S., Donapaty, S., Guo, F., Yamaguchi, H., Wang, H. G., Atadja, P., and Bhalla, K. Histone deacetylase inhibitor LAQ824 down-regulates Her-2 and sensitizes human breast cancer cells to trastuzumab, taxotere, gemcitabine, and epothilone B. Mol Cancer Ther, 2: 971-984, 2003).

Figure 15:
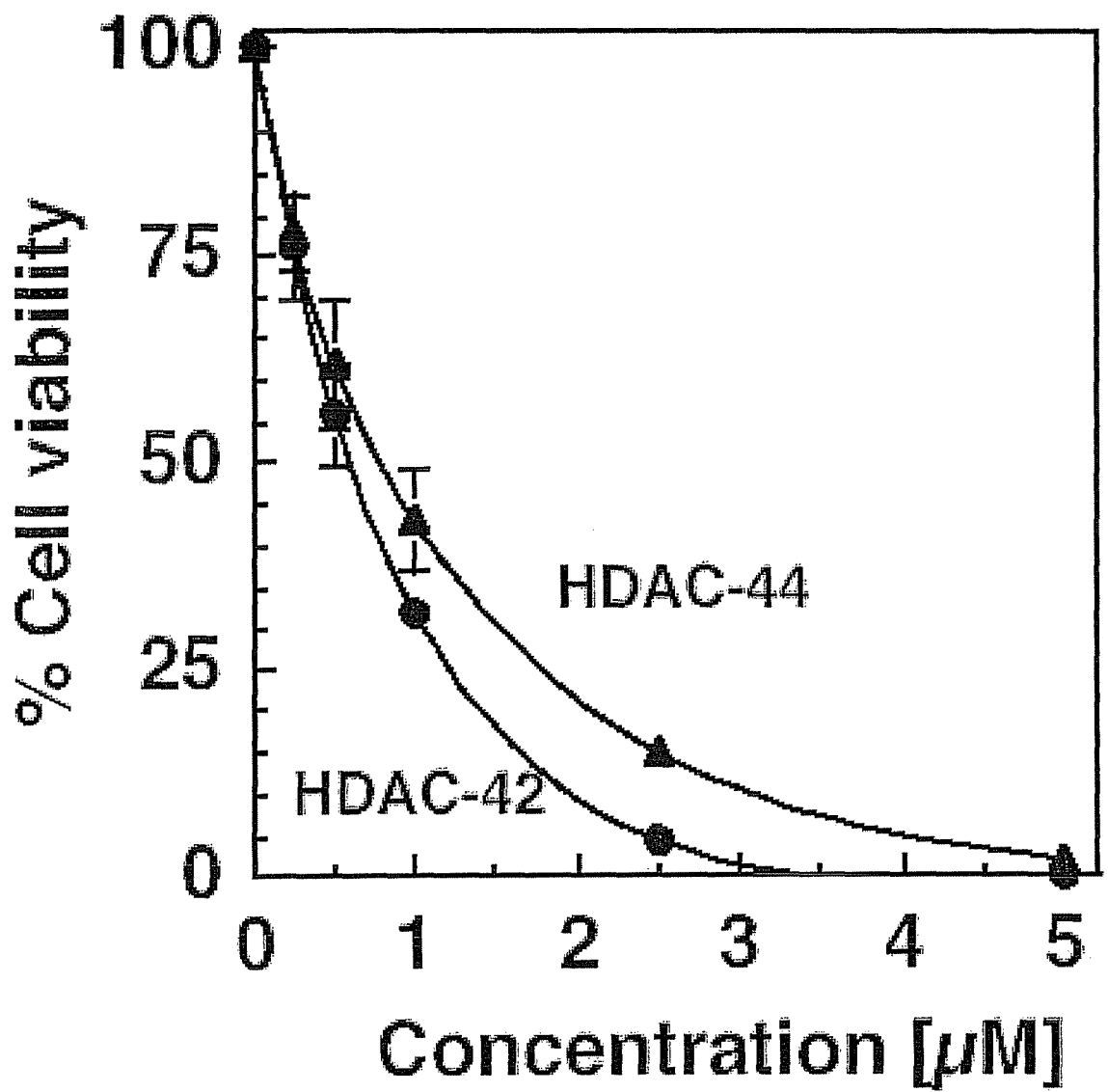
FIG. 15 shows the effect of orally administered compound 42 on the growth of established PC-3 xenograft tumors.

In vivo characterization of the antitumor effects of compound 42 on prostate cancer. The effect of orally administered compound 42 (50 and 100 mg/kg/day) vis-à-vis intraperitoneally injected SAHA (50 mg/kg/day) on the growth of established PC-3 xenograft tumors was examined. In addition, we also included compound 44 (50 and 100 mg/kg/day) in light of its comparable HDAC inhibitory potency to that of compound 42 ($IC_{50}$, 32 versus 25 nM). Both compounds 42 and 44 were effective in suppressing in vitro PC-3 cell proliferation in 10% FBS-containing medium in a dose-dependent manner, with $IC_{50}$ values of 0.6 and 0.8 µM, respectively (FIG. 15, 72-h treatment).

Figure 16:
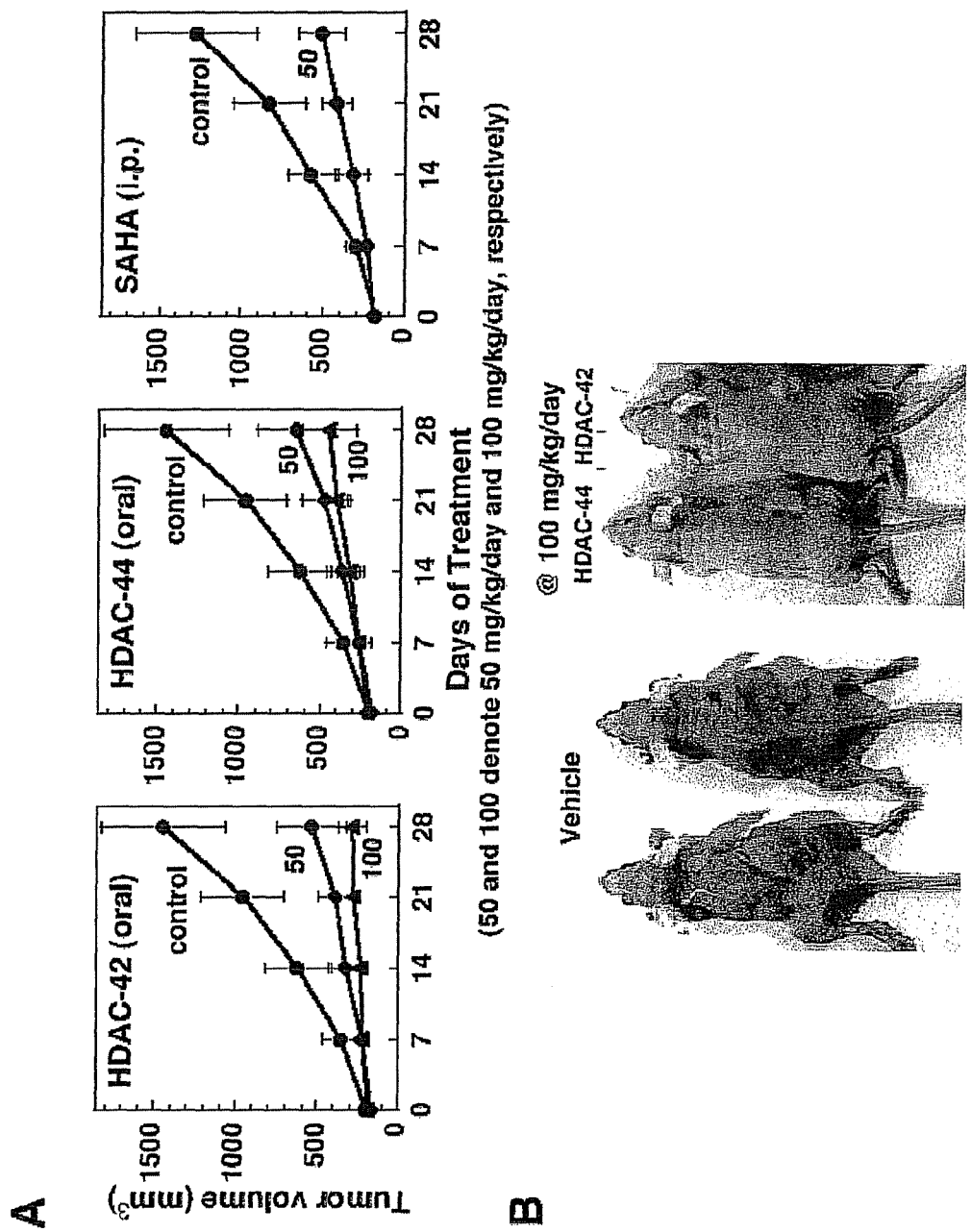
FIG. 16 shows the effect of compound 42, compound 44, and SAHA on the growth of subcutaneous PC-3 xenograft tumors in athymic mice.

FIG. 16 depicts the growth of subcutaneous PC-3 xenograft tumors in athymic mice treated with HDAC inhibitors as described above (Panel A, data presented as mean tumor volume ±SD; Panel B, photographs of representative mice from groups treated with vehicle, compound 44 and compound 42). As shown, both compounds 42 and 44 at either dose were effective in suppressing the growth of established PC-3 tumors via the oral route. The in vivo efficacy of oral compound 42 at 50 mg/kg/day was comparable to that of i.p. SAHA at the same dose, which caused reductions of 70.4% and 69.9%, respectively, in the growth of the tumors in comparison to the vehicle-treated control groups. At 100 mg/kg/day, compound 42 caused a nearly complete inhibition of PC-3 tumor growth (91.7% reduction) in the absence of overt toxicity as assessed by monitoring body weights and pathological examination.

At the conclusion of the study, complete pathological evaluation of one mouse from each treatment group was performed by board-certified veterinary pathologists at The Ohio State University College of Veterinary Medicine, which included clinical pathology (hematology, serum chemistries) and complete necropsy (gross and microscopic examination of at least 27 different tissues and organs). Gross pathologic abnormalities observed at necropsy were limited to small adhesions in the peritoneum of the SAHA-treated and DMSO-treated control mice, which were likely secondary to the daily i.p. injections. Hematological parameters were within normal limits except for a neutrophilia, which was observed only in mice from both vehicle-treated control groups and the SAHA- and compound 44 (50 mg/kg)-treated groups. Serum chemistry values were consistent with mild dehydration in the vehicle-treated mice, but were within normal limits for all other mice.

Figure 17:
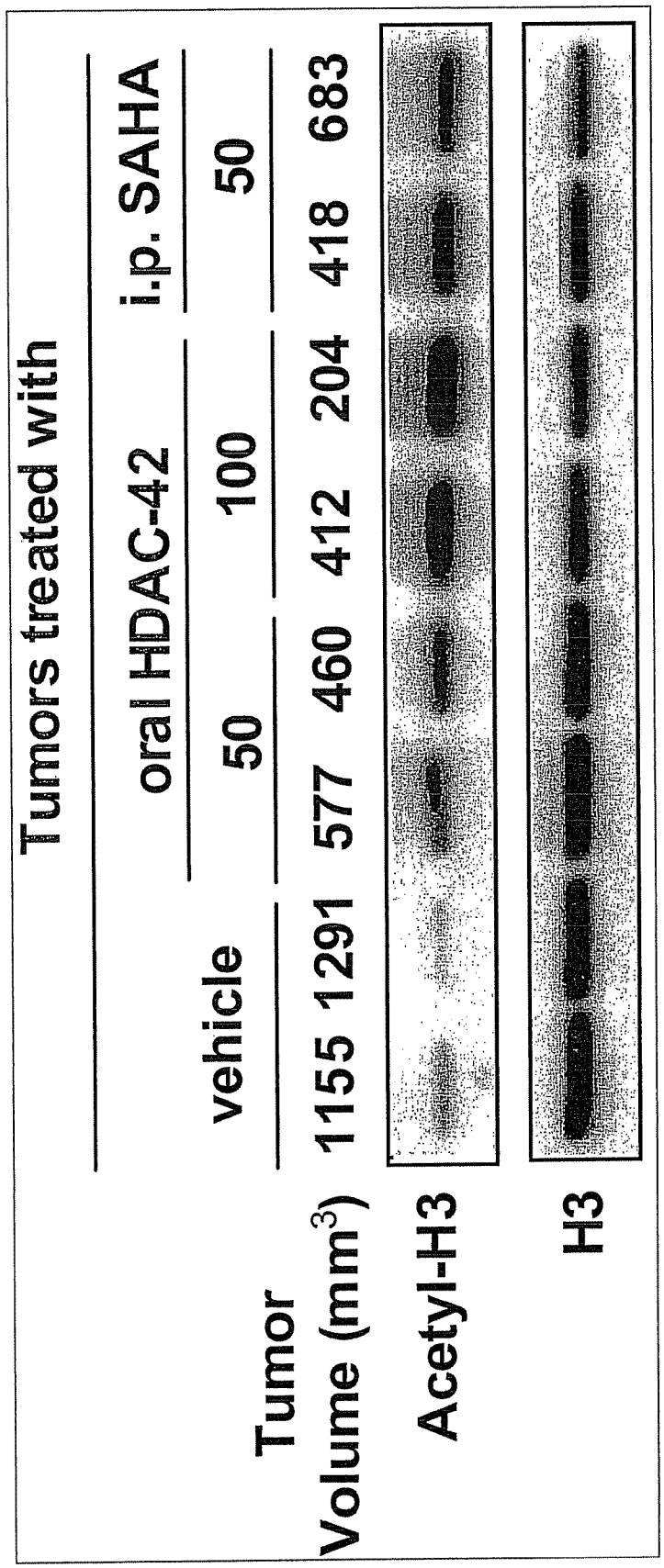
FIG. 17 shows Western blots of histone H3 and acetylated H3 in the homogenates of two representative PC-3 tumors treated with compound 42, SAHA, or control.

To correlate biological response with the proposed mechanism of action identified in vitro, the ability of orally administered compound 42 and i.p. SAHA to modulate the acetylation of histone H-3 in PC-3 xenograft tumors was assessed by immunoblotting. FIG. 17 depicts Western blots of histone H3 and acetylated H3 in the homogenates of two representative PC-3 tumors with different volumes from tumor-bearing mice treated with vehicle, oral compound 42 at 50 or 100 mg/kg/day, or i.p. SAHA at 50 mg/kg/day for 28 days. A significant increase in the acetylation level of histone H3 was noted in drug-treated groups, characteristic of in vivo HDAC inhibition.

In the in vivo experiment, PC-3 cells, suspended in equal volumes of serum-free medium and Matrigel basement membrane matrix, were injected subcutaneously into the flanks of 5-7 week old male NCr athymic nude mice (nu/nu) ($0.5 \times 10^6$ cells/0.1 ml/mouse). Daily treatment with compound 42 or 44 (50 and 100 mg/kg/day) by oral gavage or SAHA (50 mg/kg/day) by intraperitoneal injection (N=6 for each group) began when tumor volumes reached 170-200 mm$^3$. The control group received p.o. or i.p. vehicle only (0.1% methylcellulose/0.05% Tween 80 in water and DMSO, respectively). Treatments continued until the mean tumor volume of the control group reached approximately 1,500 mm$^3$. Tumors were measured every week using Vernier calipers and their volumes calculated using a standard formula: width$^2 \times$ length$\times 0.52$. Body weights were measured weekly and were stable throughout the study.

Figure 18:
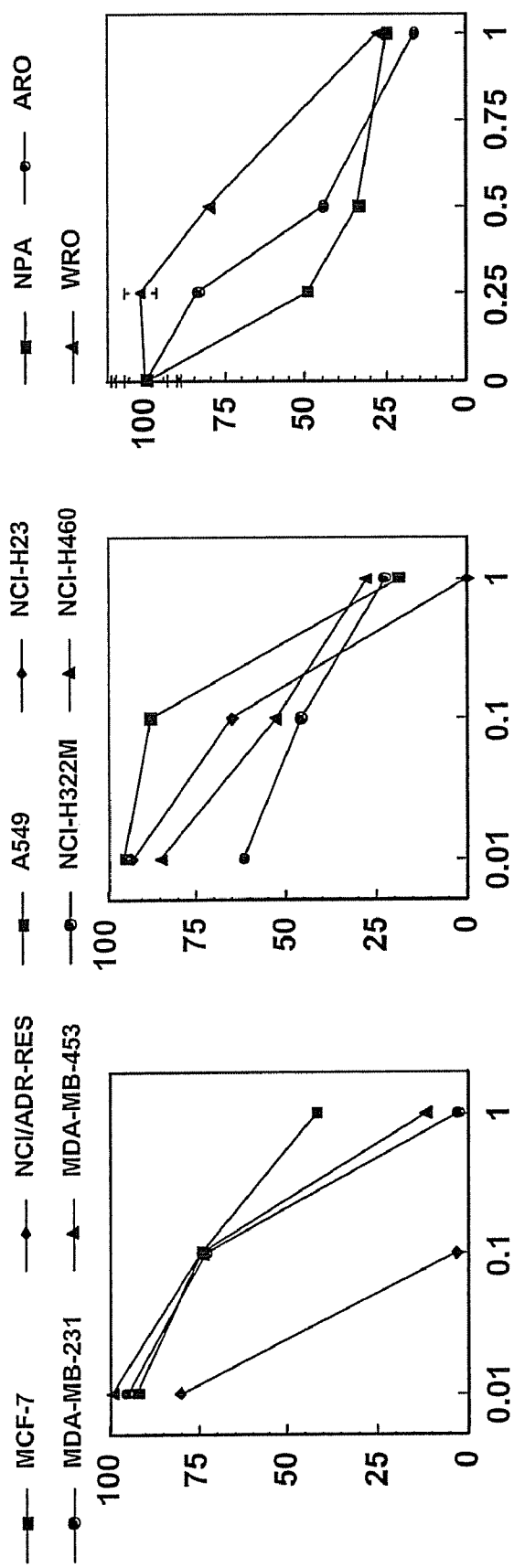
FIG. 18 shows the dose-dependent antiproliferative effects of compound 42 on representative breast, lung, and thyroid cancer cell lines.

In vitro antiproliferative effects of compound 42 in breast cancer cell lines, lung cancer cell lines, and thyroid cancer cell lines. According to the sixty-cell line screening by the NCI Developmental Therapeutics Program (DPT), compound 42 exhibited potent in vitro antiproliferative activities with an average GI50 (50% inhibition of cell growth) value of 0.2 µM against all 60 cell lines. In addition, we have tested compound 42 in thyroid cancer cell lines. The dose-dependent antiproliferative effects of compound 42 in representative breast, lung, and thyroid cancer cell lines are shown in FIG. 18.

Figure 19:
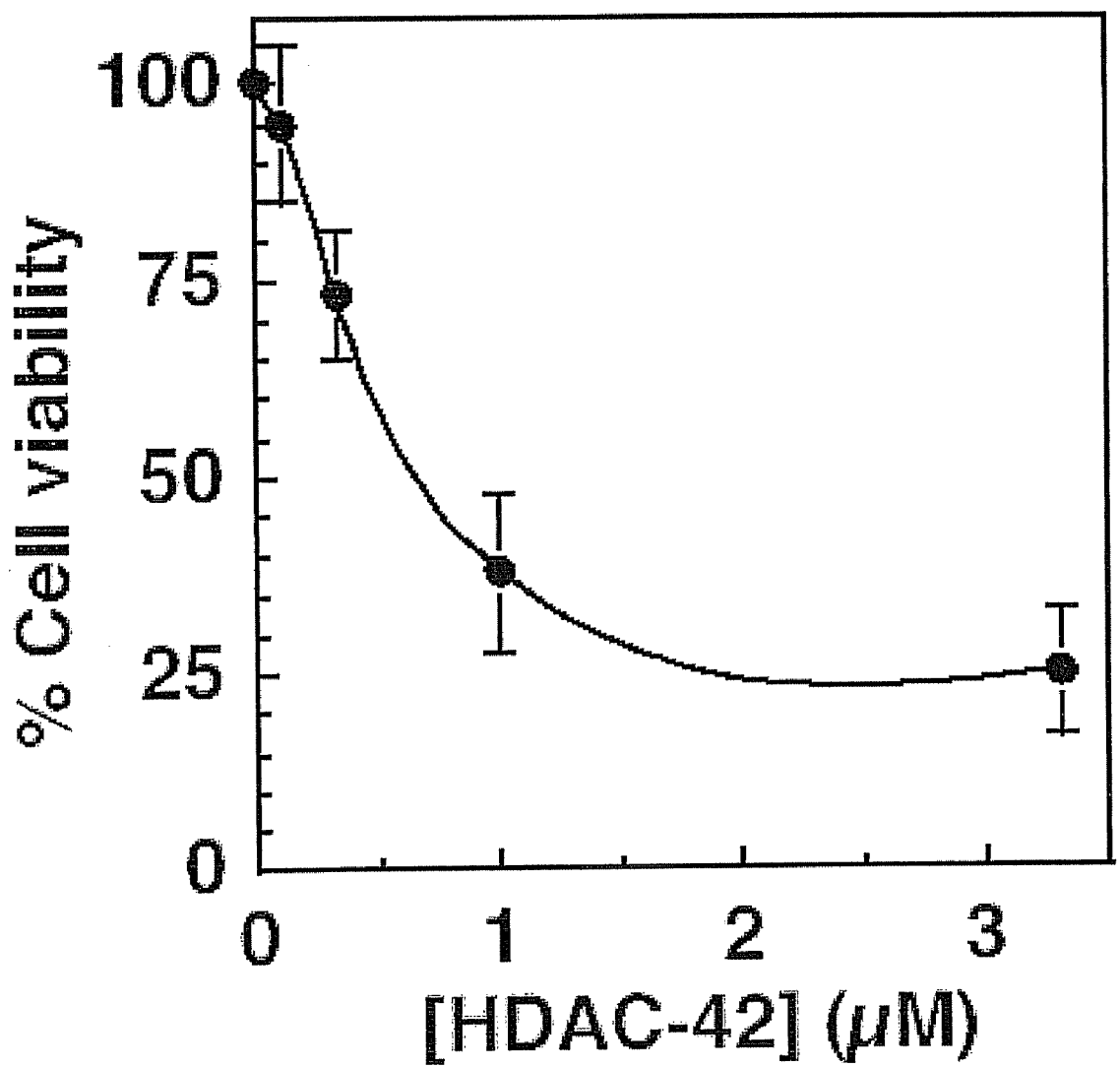
FIG. 19 shows the effect of compound 42 on primary CLL cells.

In vitro and in vivo antiproliferative effect of compound 42 in chronic lymphocytic leukemia (CLL). Compound 42 was tested in primary CLL cells for its ability to inhibit HDACs and promote cytotoxicity. As shown in FIG. 19, at the 1 µM and above concentration where HDACs are inhibited, significant cytotoxicity was observed (N=6). In addition, a pilot in vivo study using the TLC-1 transgenic mouse model indicates a trend toward improved survival and no notable toxicity with 100 mg/kg compound 42 by oral gavage for 5 days on/two days off for 4 weeks.

Stereoselectivity

It was surprisingly discovered that the HDAC-inhibitory activity of compound 42 is stereoselective, of which the (S)-isomer is more potent than the (R)-counterpart (IC50, 15 nM versus 80 nM).

In summary, by combining molecular modeling and combinatorial chemistry techniques, short-chain fatty acids were used as scaffolds to develop a novel class of potent HDAC inhibitors. The optimal agent, compound 42 (NSC-D-731438) inhibits HDAC activity with an $IC_{50}$ of 25 nM, a more than 10,000-fold increase over that of its parent compound phenylbutyrate. Compound 42 exhibits several unique features that make it a promising candidate to be brought into the clinic. First, compound 42 mediates in vitro antiproliferative effects through both epigenetic and cellular mechanisms, a feature that is similar to that of TSA, but is lacking in SAHA. Second, it is orally bioavailable with in vitro and/or in vivo potency superior to than that of MS-275 and SAHA. Third, it has no demonstrable toxicity in tumor-bearing mice after a 28-day course at the dose of 50 or 100 mg/kg/day, which offers the opportunity for chronic administration and combination with other targeted therapies. Finally, compound 42 has a simple structure, and is amenable to large-scale synthesis.

Production of Compound 42

Figure 20:
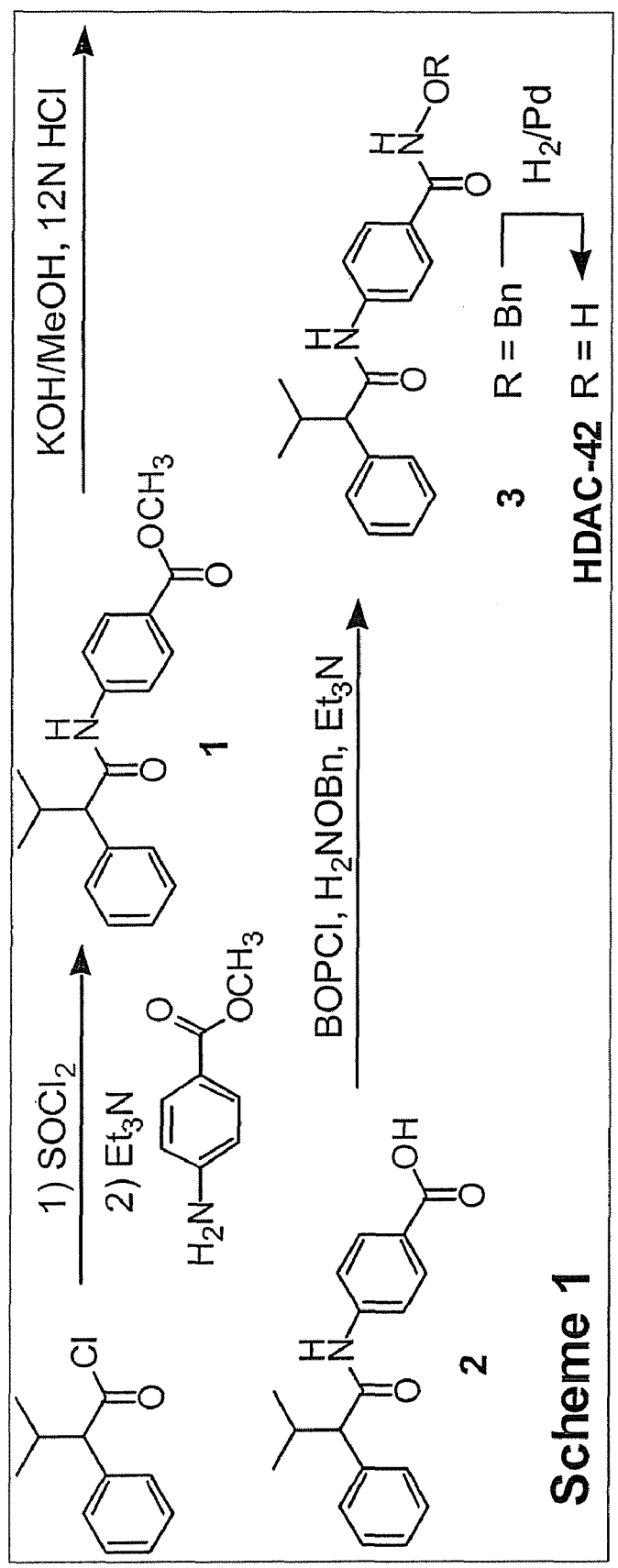
FIG. 20 diagrammatically illustrates a chemical synthesis scheme for compound 42.

The inventors have synthesized compound 42 numerous times in multi-gram scales. Basically, it has been prepared via a four-step synthesis with overall yield of 52% (FIG. 20). All starting materials are readily available, and the synthesis is amenable to scale-up to multi-hundred gram levels in a laboratory setting, of which the procedures are described as follows. The intermediates and final product could be isolated by crystallization from the reaction mixture with purity greater than 99% without using chromatographic separation. Overall, the synthesis and purification procedures are straightforward, and there is no special concern regarding the large-scale production of this compound.

N-(4-Acetyl-phenyl-3-methyl-2-phenyl-butyramide (1). (α-Isopropyl)-phenylacetic acid (4 g, 22.3 mmol) was dissolved in thionyl chloride (30 ml), and heated at 50° C. for 1 hr. After removing the solvent, the residue was dissolved in THF (50 ml), and p-aminobenzoic acid methyl ester (3.4 g, 22.5 mmol) and Et₃N (3.5 ml, 25 mmol) in THF (50 ml) were added with stirring at room temperature. After 4 hr, THF was removed under vacuum, dissolved in ethyl acetate (200 ml), and washed, in tandem, with water (100 ml) and brine (100 ml). The organic layer was dried over Na₂SO₄, and concentrated under vacuum, yielding compound 1 (5.6 g; yield 85%). The crude product was used for the next step without further purification.

4-(3-methyl-2-phenyl-butyrylamino)benzoic acid (2). Compound 1 (5.6 g; 20 mmol) was dissolved in methanol (150 ml) containing KOH (21 g). The mixture was refluxed for 2 hr, cooled to 0° C., and 30 ml of 12 N HCl (12N) was added dropwise to precipitate out the product. Solvent was removed under vacuum, and cold water (120 ml) was added. The precipitate was collected by filtration, washed with water, and dried, yielding compound 2 (5 g; yield 84%).

N-Benzyloxy-4-(3-methyl-2-phenyl-butyrylamino)-benzamide (3). To a solution of 2 (5 g; 16.8 mmol) in dry THF (120 ml) was added triethylamine (TEA, 2.5 ml; 16.8 mmol) under N₂. The mixture was stirred at room temperature for 10 min, and bis(2-oxo-3-oxazolidinyl)phosphordiamidic chloride (BOP-Cl) (4.7 g; 18.7 mmol), O-benzylhydroxylamine hydrochloride (2.7 g; 17 mmol), and TEA (7.5 ml) were added. After stirring at room temperature overnight, the solution was concentrated under vacuum, and ethyl acetate (200 ml) was added, followed by 3% NaHCO₃ (80 ml). The organic phase was separated, and washed consecutively with water and saturated brine, 100 ml each, dried over Na₂SO₄, and concentrated under vacuum. The residue (6.1 g, 90% yield) was used directly for hydrogenolysis without further purification.

N-Hydroxy-4-(3-methyl-2-phenyl-butyrylamino)-benzamide (4). Compound 3 (6.1 g; 15.2 mmol) was dissolved in 1:1 methanol/THF (120 ml), and 10% palladium on charcoal (0.6 g, 10% w/w) was added. The mixture was treated with hydrogen under atmospheric pressure for 2 h, and filtered. The solvent was evaporated and the residue was recrystallized with ethyl acetate, yielding 4.2 g (90% yield).

Figure 21:
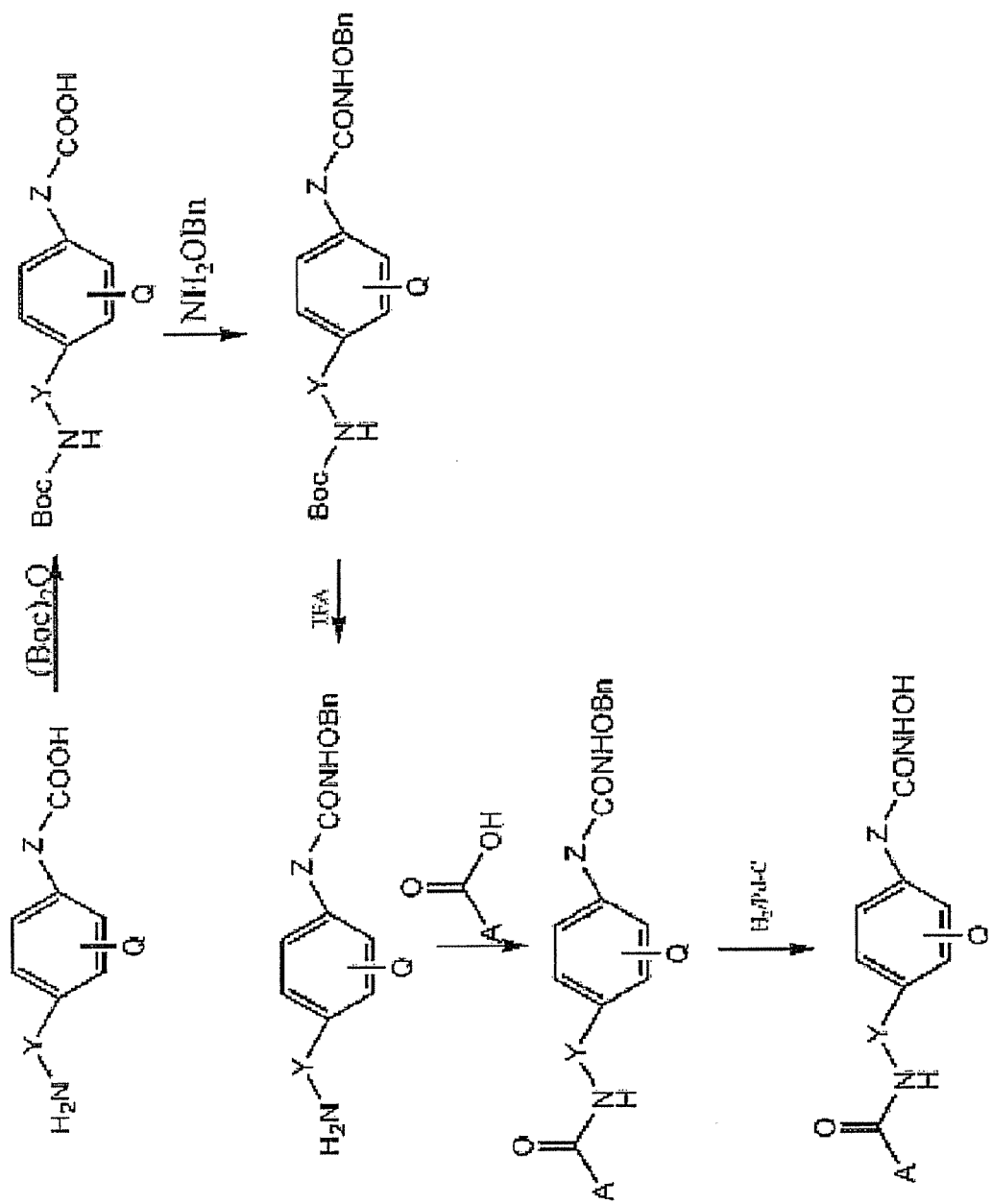
FIG. 21 diagrammatically illustrates a generic chemical synthesis scheme for compounds according to the invention.

An alternative scheme for synthesis of HDAC inhibitors according to the present invention is illustrated in FIG. 21.

Other embodiments of the invention will be apparent to those skilled in the art from consideration of the specification and practice of the invention disclosed herein.

It is intended that the specification and examples be considered as exemplary only, with a true scope and spirit of the invention being indicated by the following claims.

What is claimed is:

1. A method of treating a cancer in an animal comprising: administering to an animal having cancer a therapeutically effective amount of a compound having the formula:

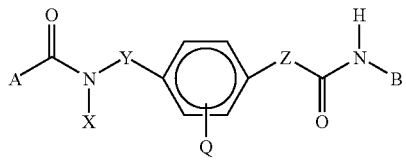

wherein:
X is chosen from H and CH₃;
Y is (CH₂)n wherein n is 0-2;
Z is chosen from (CH₂)ₘ wherein m is 0-3 and (CH)₂;
A is an aliphatic group having from 5 to 14 carbons;
B is o-aminophenyl or hydroxyl group; and
Q is a halogen, hydrogen, or methyl; and
wherein the cancer is selected from a group consisting of prostate cancer, lung cancer, acute leukemia, multiple myeloma, breast carcinoma, and melanoma.

2. The method according to claim 1, wherein the aliphatic group is branched.

3. A method of treating a cancer in an animal comprising: administering to an animal having cancer a therapeutically effective amount of a compound having the formula:

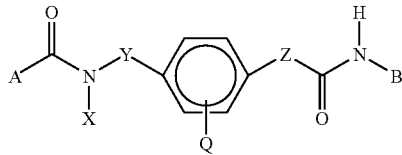

wherein:
X is chosen from H and CH₃;
Y is (CH₂)n wherein n is 0-2;
Z is chosen from (CH₂)ₘ wherein m is 0-3 and (CH)₂;
A is an aliphatic group having from 5 to 14 carbons;
B is a hydroxyl group; and
Q is a halogen, hydrogen, or methyl; and
wherein the cancer is selected from a group consisting of prostate cancer, lung cancer, acute leukemia, multiple myeloma, breast carcinoma, and melanoma.

4. A method of treating a cancer in an animal comprising administering to an animal having cancer a therapeutically effective amount of a compound chosen from N-hydroxy-4-(2-methyl-2-phenyl-propionylamino)-benzamide; N-hydroxy-4-(3-methyl-2-phenyl-butyrylamino)-benzamide; N-hydroxy-4-(3-phenyl-propionylamino)-benzamide; 4-(2,2-Dimethyl-4-phenyl-butyrylamino)-N-hydroxy-benzamide; N-hydroxy-4-[methyl-(4-phenyl-butyryl)-amino]-benzamide; N₇hydroxy-4-(2-phenyl-propionylamino)-benzamide; N-hydroxy-4-(2-methoxy-2-phenyl-acetylamino)-benzamide; 4-Diphenylacetylamino-N-hydroxy-benzamide; and N-hydroxy-4-[2-(4-isobutyl-phenyl)-propionylamino]-benzamide, wherein the cancer is selected from a group consisting of prostate cancer, lung cancer, acute leukemia, multiple myeloma, breast carcinoma, and melanoma.

5. A method of treating a cancer in an animal comprising: administering to an animal having cancer a therapeutically effective amount of a compound having the formula:

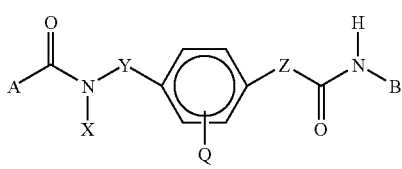

wherein:
X is chosen from H and CH$_3$;
Y is (CH$_2$)n wherein n is 0-2;
Z is chosen from (CH$_2$)$_m$ wherein m is 0-3 and (CH)$_2$;
A is an α- or β- branched aromatic fatty group having from 8 to 14 carbons;
B is hydroxyl, and Q is hydrogen; and
wherein the cancer is selected from a group consisting of prostate cancer, lung cancer, acute leukemia, multiple myeloma, breast carcinoma, and melanoma.

6. A method of treating a cancer in an animal comprising administering to an animal having cancer a therapeutically effective amount of the compound:

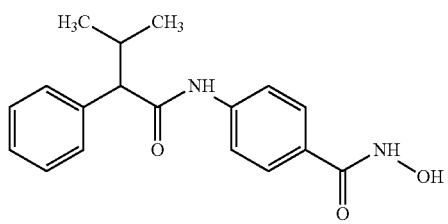

or a pharmaceutically acceptable salt thereof, wherein the cancer is selected from a group consisting of prostate cancer, lung cancer, acute leukemia, multiple myeloma, breast carcinoma, and melanoma.

7. The method of claim 1, wherein the animal is a human.

8. A method of inhibiting cancerous cell proliferation in an animal comprising:
administering a therapeutically effective amount of a compound having the formula:

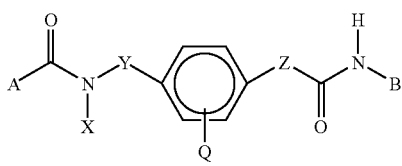

wherein:
X is chosen from H and CH$_3$;
Y is (CH$_2$)n wherein n is 0-2;
Z is chosen from (CH$_2$)$_m$ wherein m is 0-3 and (CH)$_2$;
A is an aliphatic group having from 5 to 14 carbons;
B is o-aminophenyl or hydroxyl group; and
Q is a halogen, hydrogen, or methyl, and
wherein the cancerous cell is selected from a group consisting of prostate cancer, lung cancer, acute leukemia, multiple myeloma, breast carcinoma, and melanoma.

9. The method according to claim 8, wherein the aliphatic group is branched.

10. The method according to claim 8, wherein B is hydroxyl.

11. A method of inhibiting cancerous cell proliferation in an animal comprising administering a therapeutically effective amount of a compound chosen from N-hydroxy-4-(2-methyl-2-phenyl-propionylamino)-benzamide; N-hydroxy-4-(3-methyl-2-phenyl-butyrylamino)-benzamide; N-hydroxy-4-(3-phenyl-propionylamino)-benzamide; 4-(2,2-Dimethyl-4-phenyl-butyrylamino)-N-hydroxy-benzamide; N-hydroxy-4-[methyl-(4-phenyl-butyryl)-amino]-benzamide; N-hydroxy-4-(2-phenyl-propionylamino)-benzamide; N-hydroxy-4-(2-methoxy-2-phenyl-acetylamino)-benzamide; 4-Diphenylacetylamino-N-hydroxy-benzamide; and N-hydroxy-4-[2-(4-isobutyl-phenyl)-propionylamino]-benzamide, wherein the cancer is selected from a group consisting of prostate cancer, lung cancer, acute leukemia, multiple myeloma, breast carcinoma, and melanoma.

12. A method of inhibiting cancerous cell proliferation in an animal comprising:
administering a therapeutically effective amount of a compound having the formula:

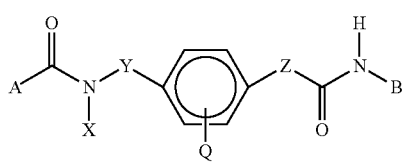

wherein:
X is chosen from H and CH$_3$;
Y is (CH$_2$)n wherein n is 0-2;
Z is chosen from (CH$_2$)$_m$ wherein m is 0-3 and (CH)$_2$;
A is an α-branched aromatic fatty group having from 8 to 14 carbons;
B is hydroxyl, and Q is hydrogen; and
wherein the cancerous cell is selected from a group consisting of prostate cancer, lung cancer, acute leukemia, multiple myeloma, breast carcinoma, and melanoma.

13. The method according to claim 12, wherein m=0 and X=H.

14. A method of inhibiting cancerous cell proliferation in an animal comprising administering a therapeutically effective amount of the compound:

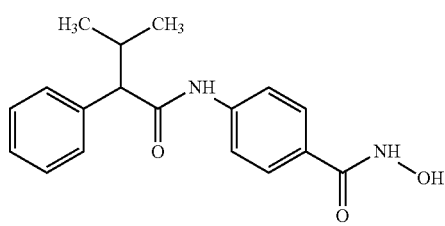

or a pharmaceutically acceptable salt thereof, wherein the cancerous cell is selected from a group consisting of prostate cancer, lung cancer, acute leukemia, multiple myeloma, breast carcinoma, and melanoma.

15. The method of claim 8, wherein the animal is a human.

16. A method of inducing apoptosis in cancerous cells comprising:
administering a therapeutically effective amount of a compound having the formula:

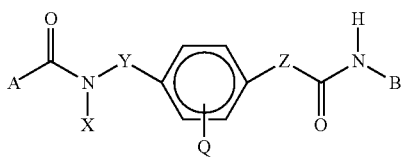

wherein:
X is chosen from H and CH$_3$;
Y is (CH$_2$)n wherein n is 0-2;
Z is chosen from (CH$_2$)$_m$ wherein m is 0-3 and (CH$_2$)$_2$;
A is an aliphatic group having from 5 to 14 carbons;
B is o-aminophenyl or hydroxyl group; and
Q is a halogen, hydrogen, or methyl; and
wherein the cancerous cell is selected from a group consisting of prostate cancer, lung cancer, acute leukemia, multiple myeloma, breast carcinoma, and melanoma.

17. The method according to claim 16, wherein the aliphatic group is branched.

18. The method according to claim 16, wherein B is hydroxyl.

19. A method of inducing apoptosis in cancerous cells comprising administering a therapeutically effective amount of a compound chosen from N-hydroxy-4-(2-methyl-2-phenyl-propionylamino)-benzamide; N-hydroxy-4-(3-methyl-2-phenyl-butyrylamino)-benzamide; N-hydroxy-4-(3-phenyl-propionylamino)-benzamide; 4-(2,2-Dimethyl-4-phenyl-butyrylamino)-N-hydroxy-benzamide; N-hydroxy-4-[methyl-(4-phenyl-butyryl)-amino]-benzamide; N-hydroxy-4-(2-phenyl-propionylamino)-benzamide; N-hydroxy-4-(2-methoxy-2-phenyl-acetylamino)-benzamide; 4-Diphenylacetylamino-N-hydroxy-benzamide; and N-hydroxy-4[2-(4-isobutyl-phenyl)-propionylamino]-benzamide, wherein the cancer is selected from a group consisting of prostate cancer, lung cancer, acute leukemia, multiple myeloma, breast carcinoma, and melanoma.

20. A method of inducing apoptosis in cancerous cells comprising:
administering a therapeutically effective amount of a compound having the formula:

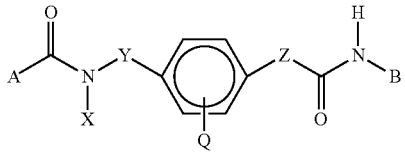

wherein:
X is chosen from H and CH$_3$;
Y is (CH$_2$)n wherein n is 0-2;
Z is chosen from. (CH$_2$)$_m$ wherein m is 0-3 and (CH$_2$)$_2$;
A is an α-branched aromatic fatty group having from 8 to 14 carbons;
B is hydroxyl, and Q is hydrogen; and
wherein the cancerous cell is selected from a group consisting of prostate cancer, lung cancer, acute leukemia, multiple myeloma, breast carcinoma, and melanoma.

21. The method according to claim 20, wherein m=0 and X=H.

22. A method of inducing apoptosis in cancerous cells comprising administering a therapeutically effective amount of the compound:

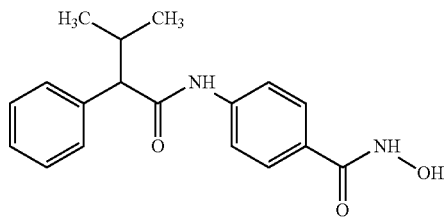

or a pharmaceutically acceptable salt thereof, wherein the cancerous cell is selected from a group consisting of prostate cancer, lung cancer, acute leukemia, multiple myeloma, breast carcinoma, and melanoma.

23. The method of claim 16, wherein the animal is a human.

24. A method of inhibiting the activity of histone deacetylases within a cancerous cell comprising:
administering a therapeutically effective amount of at least one histone deacetylase inhibitor having the formula:

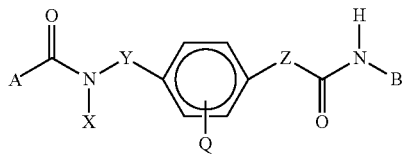

wherein:
X is chosen from H and CH$_3$;
Y is (CH$_2$)n wherein n is 0-2;
Z is chosen from (CH$_2$)$_m$ wherein m is 0-3 and (CH$_2$)$_2$;
A is an aliphatic group having from 5 to 14 carbons;
B is o-aminophenyl or hydroxyl group; and
Q is a halogen, hydrogen, or methyl; and
wherein the cancerous cell is selected from a group consisting of prostate cancer, lung cancer, acute leukemia, multiple myeloma, bladder carcinoma, renal carcinoma, breast carcinoma, colorectal carcinoma, neuroblastoma, and melanoma.

25. The method according to claim 24, wherein the aliphatic group is branched.

26. The method according to claim 24, wherein B is hydroxyl.

27. A method of inhibiting the activity of histone deacetylases within a cancerous cell comprising administering a therapeutically effective amount of at least one histone deacetylase inhibitor chosen from N-hydroxy-4-(2-methyl-2-phenyl-propionylamino)-benzamide; N-hydroxy-4-(3-methyl-2-phenyl-butyrylamino)-benzamide; N-hydroxy-4-(3-phenyl-propionylamino)-benzamide; 4-(2,2-Dimethyl-4-phenyl-butyrylamino)-N-hydroxy-benzamide; N-hydroxy-4-[methyl-(4-phenyl-butyryl)-amino]-benzamide; N-hydroxy-4-(2-phenyl-propionylamino)-benzamide; N-hydroxy-4-(2-methoxy-2-phenyl-acetylamino)-benzamide; 4-Diphenylacetylamino-N-hydroxy-benzamide; and N-hydroxy-4-[2-(4-isobutyl-phenyl)-propionylamino]-benzamide, wherein the cancer is selected from a group consisting of prostate cancer, lung cancer, acute leukemia, multiple myeloma, breast carcinoma, and melanoma.

28. A method of inhibiting the activity of histone deacetylases within a cancerous cell comprising:
administering a therapeutically effective amount of at least one histone deacetylase inhibitor having the formula:

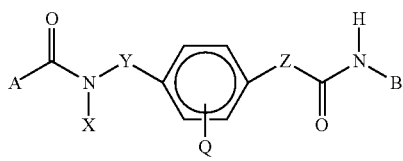

wherein:
X is chosen from H and $CH_3$;
Y is $(CH_2)n$ wherein n is 0-2;
Z is chosen from $(CH_2)_m$ wherein m is 0-3 and $(CH_2)_2$;
A is an α-branched aromatic fatty group having from 8 to 14 carbons;
B is hydroxyl, and Q is hydrogen; and
wherein the cancerous cell is selected from a group consisting of prostate cancer, lung cancer, acute leukemia, multiple myeloma, bladder carcinoma, renal carcinoma, breast carcinoma, colorectal carcinoma, neuroblastoma, and melanoma.

29. The method according to claim 28, wherein m=0 and X=H.

30. A method of inhibiting the activity of histone deacetylases within a cancerous cell comprising administering a therapeutically effective amount of the compound:

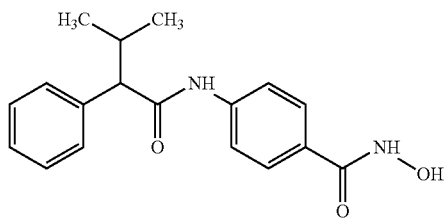

or a pharmaceutically acceptable salt thereof, wherein the cancerous cell is selected from a group consisting of prostate cancer, lung cancer, acute leukemia, multiple myeloma, bladder carcinoma, renal carcinoma, breast carcinoma, colorectal carcinoma, neuroblastoma, and melanoma.

31. The method of claim 24, wherein the animal is a human.

32. The method according to claim 5, wherein A is selected from the group consisting of

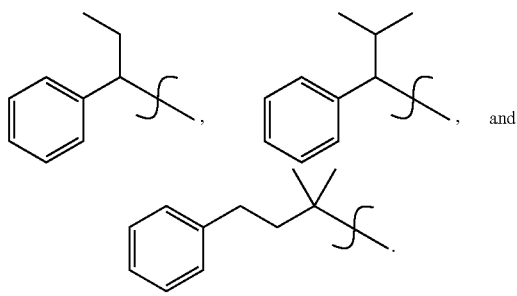

33. The method according to claim 12, wherein A is selected from the group consisting of

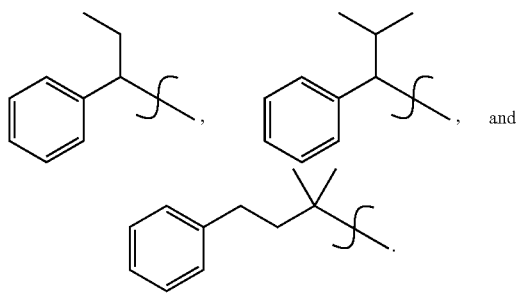

34. The method according to claim 20, wherein A is selected from the group consisting of

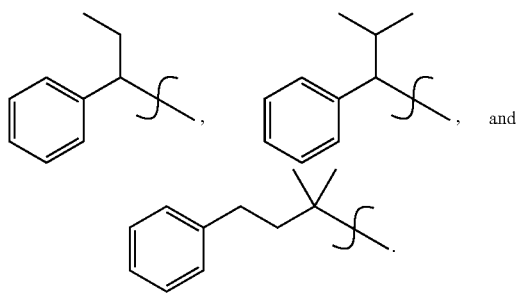

35. The method according to claim 28, wherein A is selected from the group consisting of

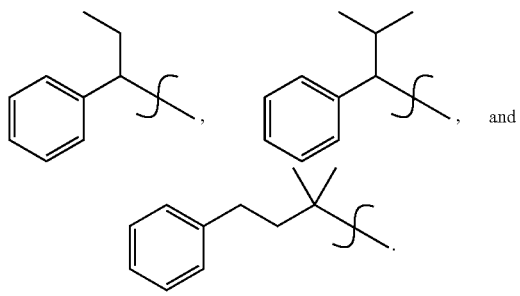

36. A method of treating a cancer in an animal comprising:
administering to an animal having cancer a therapeutically effective amount of a compound having the formula:

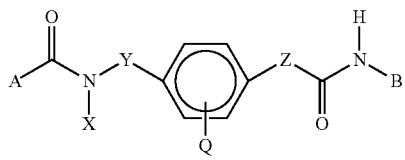

wherein:
X is chosen from H and $CH_3$;
Y is $(CH_2)n$ wherein n is 0-2;
Z is chosen from $(CH_2)_m$ wherein m is 0-3;
A is an aralkyl, or alkaryl group having from 8 to 14 carbons;
B is hydroxyl, and Q is hydrogen; and
wherein the cancer is selected from a group consisting of prostate cancer, lung cancer, acute leukemia, multiple myeloma, breast carcinoma, and melanoma.

37. The method according to claim 36, wherein m=0 and X=H.

38. The method according to claim 36, wherein the animal is human.

* * * * *